US011618899B2

(12) United States Patent
Studier

(10) Patent No.: US 11,618,899 B2
(45) Date of Patent: Apr. 4, 2023

(54) CLONING AND EXPRESSION VECTORS AND SYSTEMS

(71) Applicant: Brookhaven Science Associates, LLC, Upton, NY (US)

(72) Inventor: F. William Studier, Pleasanton, CA (US)

(73) Assignee: Brookhaven Science Associates, LLC, Upton, NY (US)

(*) Notice: Subject to any disclaimer, the term of this patent is extended or adjusted under 35 U.S.C. 154(b) by 1154 days.

(21) Appl. No.: 16/077,014

(22) PCT Filed: Feb. 8, 2017

(86) PCT No.: PCT/US2017/017061
§ 371 (c)(1),
(2) Date: Aug. 9, 2018

(87) PCT Pub. No.: WO2017/139412
PCT Pub. Date: Aug. 17, 2017

(65) Prior Publication Data
US 2019/0032048 A1    Jan. 31, 2019

Related U.S. Application Data

(60) Provisional application No. 62/293,089, filed on Feb. 9, 2016.

(51) Int. Cl.
| | | |
|---|---|---|
| C12N 15/11 | (2006.01) | |
| C12N 15/66 | (2006.01) | |
| C12N 15/67 | (2006.01) | |
| C12N 15/70 | (2006.01) | |
| C12N 15/63 | (2006.01) | |
| C12N 9/12 | (2006.01) | |

(52) U.S. Cl.
CPC ............ *C12N 15/11* (2013.01); *C12N 9/1247* (2013.01); *C12N 15/63* (2013.01); *C12N 15/66* (2013.01); *C12N 15/67* (2013.01); *C12N 15/70* (2013.01); *C12Y 207/07006* (2013.01)

(58) Field of Classification Search
CPC .................................................. C12N 15/63
See application file for complete search history.

(56) References Cited

U.S. PATENT DOCUMENTS

| | | |
|---|---|---|
| 5,910,438 A | 6/1999 | Bernard et al. |
| 6,180,407 B1 | 1/2001 | Bernard et al. |
| 6,248,569 B1 | 6/2001 | Dunn et al. |
| 6,537,779 B1 | 3/2003 | Kara et al. |
| 7,560,264 B2 | 7/2009 | Studier |
| 7,704,722 B2 | 4/2010 | Studier |
| 7,709,624 B2 | 5/2010 | Nakashima et al. |
| 7,759,109 B2 | 7/2010 | Studier |
| 8,241,887 B2 | 8/2012 | Studier |
| 8,399,217 B2 | 3/2013 | Studier |
| 2007/0072297 A1 | 3/2007 | Ji et al. |
| 2014/0186959 A1 | 7/2014 | Slater et al. |
| 2015/0126452 A1* | 5/2015 | Schiller .............. C12N 15/1031 510/501 |

FOREIGN PATENT DOCUMENTS

WO    WO1991/02077 A1    2/1991

OTHER PUBLICATIONS

Goffin, P. & Dehottay, P., "Complete Genome Sequence of *Escherichia coli* BLR(DE3), a recADeficient Derivative of *E. coli* BL21(DE3)", American Society for Microbiology, 2017, vol. 5, Issue 22, e00441-17. pp. 1-2.*
Kwon et al., "Comparative genomics and experimental evolution of *Escherichia coli* BL21(DE3) strains reveal the landscape of toxicity escape from membrane protein overproduction," Sci Rep, Nov. 4, 2015 (Apr. 11, 2015), vol. 5, No. 16076, pp. 1-13.
Studier et al., "Use of bacteriophage T7 RNA polymerase to direct selective high-level expression of cloned genes," J Viol Biol. May 5, 1986;189(1): pp. 113-130.
Rosenberg et al. "Vectors for selective expression of cloned DNAs by T7 RNA polymerase," (1987) Gene 56(1): pp. 125-135.
Studier et al. "Use of T7 RNA polymerase to direct expression of cloned genes," (1990) Met. Enzymology 185: pp. 60-89.
Studier "Protein production by auto-induction in high density shaking cultures," (2005) Protein Expr. Purif. 41: pp. 207-234.
Bolivar et al. "Construction and characterization of new cloning vehicles. II. A multipurpose cloning system," (1977) Gene 2: pp. 95-113.
Studier "Use of bacteriophage T7 lysozyme to improve an inducible T7 expression system," (1991) J. Mol. Biol. 219: pp. 37-44.
Giordano et al. "Regulation of coliphage T3 and T7 RNA polymerases by the lac repressor-operator system," (1989) Gene 84: pp. 209-219.
Dubendorff et al. "Controlling basal expression in an inducible T7 expression system by blocking the target T7 promoter with lac repressor," (1991) J. Mol. Biol. 219: pp. 45-59.
Miroux et al. "Over-production of proteins in *Escherichia coli*: mutant hosts that allow synthesis of some membrane proteins and globular proteins at high levels," (1996) J. Mol. Biol. 260: pp. 289-298.
Schlegel et al. "De-convoluting the Genetic Adaptations of *E. coli* C41(DE3) in Real Time Reveals How Alleviating Protein Production Stress Improves Yields," (2015) Cell Reports 10(10): pp. 1758-1766.

(Continued)

*Primary Examiner* — Suzanne M Noakes
(74) *Attorney, Agent, or Firm* — Dorene M. Price

(57) ABSTRACT

Vectors for cloning, maintaining and expressing a wide range of coding sequences in inducible T7 expression systems in *Escherichia coli* expression hosts are disclosed herein. Target genes that can be stably maintained and expressed include those that specify proteins that are highly toxic to the host cell. Different configurations of vectors and expression hosts provide different rates of transcription and translation of target genes and therefore different rates of accumulation of target proteins. Methods for cloning by asymmetric ligation and co-expression of more than one target protein in a single vector are also disclosed, as are variants of BL21(DE3) having lower basal transcription by T7 RNA polymerase.

8 Claims, 6 Drawing Sheets

Specification includes a Sequence Listing.

(56) References Cited

OTHER PUBLICATIONS

Dunn et al. "Complete nucleotide sequence of bacteriophage T7 DNA and the locations of T7 genetic elements," (1983) J. Mol. Biol. 166:pp. 477-535.
Bernard et al. "Positive-selection vectors using the F plasmid ccdB killer gene," (1994) Gene 148: pp. 71-74.
Reyrat et al., "Counterselectable Markers: Untapped Tools for Bacterial Genetics and Pathogenesis" Infection and Immunity, Sep. 1998, pp. 4011-4017.
Müller et al. "Repression of lac promoter as a function of distance, phase and quality of an auxiliary lac operator." (1996) J. Mol. Biol. 257:pp. 21-29.
Shore et al. "DNA flexibility studied by covalent closure of short fragments into circles," (1981) Proc. Natl. Acad. Sci. USA 78:pp. 4833-4837.
Wu et al. "Specificity of the nick-closing activity of bacteriophage T4 DNA ligase," (1989) Gene 76(2):pp. 245-254.
Studier "Stable expression clones and auto-induction for protein production in *E. coli.*," (2014) Methods in Molecular Biology 1091: pp. 17-32.
Van Leen, et al. "Production of human interieukin-3 using industrial microorganisms," (1991) Bio/Technology 9:pp. 47-52.
Srinivasan, et al. "A novel high-cell-density protein expression system based on Ralstonia eutropha," (2002) Appl. Environ. Microbiol. 68(12): pp. 5925-5932.
Belanger, et al. "Production of heterologous protein by Methylobacterium extorquens in high cell density fermentation," (2004) FEMS Microbiol Lett. 231(2):pp. 197-204.
Oddone, et al. "Dual inducible expression of recombinant GFP and targeted antisense RNA in Lactococcus actis," (2009) Plasmid 62(2): pp. 108-118.

* cited by examiner

```
Tr(CATG) SEQ ID NO. 3

BsiWI   BbsI    PciI    BsaI    NcoI   BsmBI    BspHI   AgeI
    5'-cgtacggaagacta|catg tggtctcc|catg gcgtctct|catg aaccggt-3'
    3'-gcatgccttctgat gtac|accagagg gtac|cgcagaga gtac|ttggcca-5'

Tr(TA)   SEQ ID NO. 4

EagI       BtsI    BseRI   BsgI       BsrDI      EciI BpmI    SacI
  5'-cggccgta ta|cactgccactcctcctgcac ta|cattgcgcatccgcctccagtgagctc-3'
  3'-gccggcat|at gtgacggtgaggaggacgtg|at gtaacgcgtaggcggaggtcactcgag-5'

Tr(TG)   SEQ ID NO. 5

EagI       BtsI    BseRI   BsgI       BsrDI      EciI BpmI    SacI
  5'-cggccgta tg|cactgccactcctcctgcac tg|cattgcgcatccgcctccagtgagctc-3'
  3'-gccggcat|ac gtgacggtgaggaggacgtg|ac gtaacgcgtaggcggaggtcactcgag-5'
```

Figure 2 pAL1, 2, 3, 4, 5, 11, 12

PCR ends for generating 4-nt 5' overhangs with T4 DNA polymerase + dCTP
upstream      5' ccat g--------c agtg 3'      downstream
               3' ggta c--------g tcac 5' bp matches in all 10 pairwise alignments
(0 is no bp; 1 is usual DNA bp; - is GT match)

|  | 5' | ccat | atgg | agtg | cact 3' |  |
|---|---|---|---|---|---|---|
| upstream aa linkers   RF | 3' tacc | 0000 |  |  |  | RF   downstream aa linkers |
| [not MQKEW] –his-VADEG   nnc | 3' ggta | 1111 | 0--0 |  |  | nnc [not MQKEW] –his-VADEG |
| SPTA-met   ncc | 3' gtga | 1001 | 0000 | 0--0 |  | nca SPTA-val |
| pro-CW-[not IMTNK]   cca | 3' tcac | 0000 | 1001 | 1111 | 0000 | cag gln-CW-[not IMTNK] |

Figure 5A pAL13, 14

PCR ends for generating 4-nt 5' overhangs with T4 DNA polymerase + dCTP
upstream      5' actc g--------c agtg 3'      downstream
               3' tgag c--------g tcac 5' bp matches in all 10 pairwise alignments
(0 is no bp; 1 is usual DNA bp; - is GT match)

|  | 5' | actc | gagt | agtg | cact 3' |  |
|---|---|---|---|---|---|---|
| upstream aa linkers   RF | 3' ctca | 0000 |  |  |  | RF   downstream aa linkers |
| [not FMYHNDCW] –leu-VADEG   nna | 3' tgag | 1111 | -00- |  |  | nnc [not MQKEW] –his-VADEG |
| YHND-ser   nac | 3' gtga | 0--0 | 1010 | 0--0 |  | nca SPTA-val |
| thr-arg   act | 3' tcac | 0100 | 000- | 1111 | 0000 | cag gln-CW-[not IMTNK] |

Figure 5B pAL21, 22, 23, 24

PCR ends for generating 4-nt 5' overhangs with T4 DNA polymerase + dTTP
upstream      5' ctgc a--------t agcg 3'      downstream
               3' gacg t--------a tcgc 5' bp matches in all 10 pairwise alignments
(0 is no bp; 1 is usual DNA bp; - is GT match)

|  | 5' | ctgc | gcag | agcg | cgct 3' |  |
|---|---|---|---|---|---|---|
| upstream aa linkers   RF | 3' cgtc | 0--0 |  |  |  | RF   downstream aa linkers |
| [not MQKEW] –cys-IMTNKSR   nnc | 3' gacg | 1111 | 0000 |  |  | nnt [not MQKEW] –ser-VADEG |
| YHND-ser   nct | 3' gcga | 0001 | 0000 | 0110 |  | nta LIV-gly |
| Leu-HQ   ctg | 3' tcgc | 0000 | 100- | 1111 | 0000 | tag stop codon |

Figure 5C

Cloning and co-expression of two coding sequences (CDS1 and CDS2, overhang sequences capitalized)

```
              upstream      SD     linker       downstream
              overhang             overhang     overhang
           5' CCATg-CDS1-taaggagacTATTAATg-CDS2-cAGTG 3'
                         - SEQ ID NO. 79 -
```
Three perfectly base-paired and 26 imperfectly paired overhangs:

```
                         us    usC    1>2      1>2C      ds    dsC
          overhangs      5' ccat atgg tattaat  attaata   agtg  cact 3'
    us    3' tacc 5'        0000
    usC   3' ggta 5'       (1111) 0--0
    1>2   3' taattat 5'     0000  100-  0010100
                       0000       110-
    1>2C  3' ataatta 5'     0011  00-0 (1111111) 0010100
                       0001       0000
    ds    3' gtga 5'        1001  0000 -1-1      00-0     0--0
                                       -101      01-0
    dsC   3' tcac 5'        0000  1001 0010      1010    (1111) 0000
                                       0000      1010
```
Figure 6A Cloning and co-expression of three coding sequences (CDS1, CDS2 and CDS3, overhang sequences capitalized)

```
              upstream      SD    linker        SD    linker       downstream
              overhang            overhang            overhang     overhang
           5' CCATg-CDS1-taaggagacTATTAATg-CDS2-taaggagacTTAATATg-CDS3-cAGTG 3'
                         - SEQ ID NO. 79 -             - SEQ ID NO. 80 -
```
Four ungapped, perfectly base-paired overhangs and 48 imperfectly paired overhangs:

```
                         us    usC    1>2      1>2C      2>3      2>3C     ds    dsC
          overhangs      5' ccat atgg tattaat  attaata   ttaatat  atattaa  agtg  cact 3'
    us    3' tacc 5'        0000
    usC   3' ggta 5'       (1111) 0--0
    1>2   3' taattat 5'     0000  100-  0010100
                       0000       110-
    1>2C  3' ataatta 5'     0011  00-0 (1111111) 0010100
                       0001       0000
    2>3   3' tataatt 5'     0010  01--  0001010  1100001  0110110
                       0011       11-0
    2>3C  3' aattata 5'     0011  11-0  1000011  0101000 (1111111) 0110110
                       0010       01--
    ds    3' gtga 5'        1001  0000  -1-1     00-0     -000     0001    0--0
                                        -101     01-0     0001     -000
    dsC   3' tcac 5'        0000  1001  0010     1010     0000     1000   (1111) 0000
                                        0000     1010     1000     0000
```
Figure 6B

CLONING AND EXPRESSION VECTORS AND SYSTEMS

CROSS-REFERENCE TO RELATED APPLICATIONS

This application is a US National Phase Application under 35 USC § 371 of International Patent Application No. PCT/US2017/017061, filed on Feb. 8, 2017, which claims the benefit of prior U.S. Provisional Application No. 62/293,089, filed Feb. 9, 2016, all of which are hereby incorporated by reference in their entirety.

STATEMENT OF GOVERNMENT RIGHTS

The present application was made with government support under contract number DE-SC0012704 awarded by the U.S. Department of Energy. The United States government has certain rights in the invention(s).

BACKGROUND

Transcription of cloned genes by T7 RNA polymerase and translation of the mRNA directed by the highly efficient translation initiation sequence upstream of the coding sequence for the T7 major capsid protein (referred to here as tg10), has been highly successful in producing a wide range of proteins in *E. coli* (Studier et al. (1986) J. Mol. Biol. 189:113-130; Rosenberg et al. (1987) Gene 56:125-135; Studier et al. (1990) Met. Enzymology 185:60-89; Studier (2005) Protein Expr. Purif. 41:207-234). T7 RNA polymerase selectively initiates transcription at a promoter sequence (referred to here as a T7 promoter) large enough to be unlikely to be found by chance in a bacterial genome. No sequences that appear likely to serve as promoters for T7 RNA polymerase are found in completely sequenced genomes of *E. coli* expression strains such as BL21(DE3). T7 RNA polymerase is highly active and processive, and is capable of producing mRNA for a wide range of coding sequences linked to a T7 promoter in cloning vectors such as the commonly used pET vectors. This highly selective transcription and efficient tg10-directed translation can commandeer the resources of the *E. coli* cell so efficiently that, in favorable cases, almost all of the protein produced shortly after T7 RNA polymerase is induced or delivered to the cell is that specified by the cloned gene (referred to here as the target protein), which can accumulate to become more than half of the total protein in the cell.

The original pET vectors and their many successors were derived from the multi-copy plasmid pBR322, which has the colE1-type replicon from pMB1 (Rosenberg et al (1987) and Bolivar et al. (1977) Gene 2:95-113). The cloning site in the tet gene is oriented so that transcription from the T7 promoter is opposite to that from the tet promoter. Basal transcription by *E. coli* RNA polymerase at this site is low enough that most coding sequences can be cloned and maintained in the absence of T7 RNA polymerase, even if the target protein is toxic to the host cell. A convenient way to produce target proteins is for the host to supply inducible T7 RNA polymerase which, upon induction, directs expression of the target gene from a T7 promoter. However, T7 RNA polymerase is so active and tg10 so efficient that basal expression in the uninduced cell can produce enough target protein to prevent establishment of an inducible expression strain if the target protein is sufficiently toxic to the host cell. This problem was encountered in the earliest attempts to use inducible T7 RNA polymerase to produce proteins from cloned genes, and several improvements have reduced basal levels of target protein in uninduced cells, thereby stabilizing expression strains and allowing a wider range of proteins to be produced.

One early improvement was to supply a small amount of T7 lysozyme, which binds to T7 RNA polymerase and inhibits transcription, thereby reducing basal production of target protein (Studier (1991) J. Mol. Biol. 219:37-44). Upon induction, more T7 RNA polymerase is made than can be inhibited by the T7 lysozyme and high levels of target protein can be produced.

Another solution was to place a binding site for lac repressor (referred to as an operator) immediately downstream of the start site for T7 RNA polymerase (Giordano et al. (1989) Gene 84:209-219; Dubendorff et al. (1991) J. Mol. Biol. 219:45-59; and U.S. Pat. No. 6,537,779 to Kara et al. (2003; published Feb. 4, 1999), the contents of which are incorporated herein by reference). One such construct, referred to as a T7lac promoter (Dubendorff, et al. (1991)) has found wide use in pET vectors. Bound lac repressor reduces transcription from a T7lac promoter, thereby reducing basal production of the target protein. Expression of T7 RNA polymerase in BL21(DE3) and several other expression hosts is also controlled by lac repressor, so that an inducer that reduces affinity of the lac repressor for its operators both turns on production of T7 RNA polymerase and unblocks the T7 promoter, allowing high-level production of target protein.

A third type of solution is to express T7 RNA polymerase from an inducible *E. coli* promoter that has lower basal expression than the L8, lacUV5 promoter used in BL21 (DE3) (Miroux et al. (1996) J. Mol. Biol. 260:289-298; Schlegel et al. (2015) Cell Reports 10:1758-1766 and the arabinose-inducible pBAD promoter in BL21-AI (Invitrogen, now Life Technologies, a Thermo Fisher Scientific Brand)). In BL21-AI, induction of the pBAD promoter by arabinose and unblocking the T7lac promoter by an inducer of the lac repressor would both be necessary for maximal production of target protein.

However, even with these improved vectors or expression strains, some target proteins are toxic enough that inducible strains for producing them are unstable and can be maintained only with special care, or are so toxic that inducible expression strains cannot be established at all. This problem was encountered in trying to maintain and express gene 5.3 of bacteriophage T7, which specifies a protein of unknown function that is predicted to contain 118 amino acids (Dunn et al. (1983) J. Mol. Biol. 166:477-535).

Therefore, there remains a need for improved cloning and expression vectors and systems that provide tighter control of expression and improved methods of cloning into the same.

SUMMARY OF THE INVENTION

The present invention provides vectors and methods for cloning, maintaining, and expressing coding sequences in inducible T7 expression systems.

In one embodiment, the present invention provides a T7 Promoter Control Region polynucleotide including SEQ ID NO. 17, 18, 19, 23, 24, 25, 29, 30, 31, 32, 33, 34, 35, 38, 39, 40, 41, 44, 45, 46, and 47.

In one embodiment, the present invention provides a Translation Initiation Efficiency Region polynucleotide including SEQ ID NO. 48, 49, 50, 51, 52, 53, 54, 55, 56, 57, 58, 87, 88, 89, 90, 91, 92, and 93.

In one embodiment, the present invention provides an Expression Control Region polynucleotide that includes a T7 Promoter Control Region polynucleotide and a Translation Initiation Efficiency Region polynucleotide.

In one embodiment, the present invention provides a vector that includes an Expression Control Region polynucleotide.

In one embodiment, the present invention provides a vector for directional cloning of at least one target DNA by asymmetric ligation. The vector includes a cloning site with upstream and downstream outward-facing asymmetric recognition sequences for at least one Type IIS restriction endonuclease that cuts outside of its recognition sequence to produce single-stranded overhangs of arbitrary nucleotide sequence. The recognition sequences are situated such that cutting said vector with said at least one Type IIS endonuclease produces two vector fragments: 1) a cloning-acceptor fragment having a different asymmetric overhang at each end; and 2) a counter-selection fragment containing both of said outward-facing recognition sequences and having asymmetric overhangs complementary to those of said cloning-acceptor fragment.

The nucleotide sequences of said 4 asymmetric overhangs are designed so that only 2 of the 10 possible pairwise alignments between said overhangs can form ungapped perfectly base-paired substrates for efficient joining by a DNA ligase to join either strand, thereby regenerating said vector and additionally so that the number of consecutive perfect base-pairs from either ungapped end of each of the remaining 8 said possible pairwise alignments is minimized, thereby minimizing potential joining of either DNA strand at any of said remaining 8 possible pairwise aligned overhangs by said DNA ligase, and so that the potential for base-pairing adjacent to any ungapped end in each of the remaining 8 possible pairwise alignments is minimized so as to decrease probability of being joined by said DNA ligase.

In one embodiment, the present invention provides a method for directional cloning of at least one target DNA in a cloning vector disclosed herein. The method includes: 1) cutting said vector with said at least one Type IIS restriction endonuclease to produce said cloning-acceptor fragment and said counter-selection fragment; 2) providing said at least one target DNA having asymmetric single-stranded overhangs designed such that the only pairwise alignments of said overhangs of said at least one target DNA and of said cloning-acceptor fragment that can form ungapped perfectly base-paired substrates for efficient joining by a DNA ligase are those whose sequential ligation generates a directional clone of said at least one target DNA in said vector cloning-acceptor fragment or those whose ligation rejoins said cloning-acceptor and said counter-selection fragments, whereas each of the greater number of other possible pairwise alignments of said overhangs has few if any complementary base pairs near its ends and therefore has a much lower probability of being joined by said DNA ligase; 3) assembling said cut vector or said cloning-acceptor fragment produced in step 1, said at least one target DNA having said asymmetric single-stranded overhangs, and said DNA ligase in a solution and incubating under conditions that promote ligation of ungapped perfectly base-paired substrates by said DNA ligase to provide ligation products; 4) transforming said ligation products into cells; and 5) selecting transformants that contain a directional clone of said at least one target DNA in said cloning-acceptor fragment of said vector.

In one embodiment, the invention provides a method for co-expression of a plurality of coding sequences from one expression vector. The method includes obtaining a clone in said vector by the methods disclosed herein, establishing said clone in a T7 expression host, inducing production of T7 RNA polymerase in said T7 expression host, producing target mRNA by transcription of target coding sequences from a T7 promoter in the Expression Control Region polynucleotide of said vector, and initiating production of target proteins from upstream translation initiation regions for each coding sequence.

In one embodiment, the present invention provides an engineered cell including a vector disclosed herein comprising an at least one target DNA encoding at least one target protein operationally linked to said Expression Control Region polynucleotide; and an inducible T7 RNA polymerase.

DESCRIPTION OF THE FIGURES

FIG. 2 depicts examples of coding sequences that include an upstream 5'-CATG single-stranded DNA overhand and a downstream TA-3' overhang.

FIGS. 5A-5C depicts base pairs (bp) in all 10 ungapped pairwise alignments of 4-nt 5' overhangs for cloning single coding sequences by asymmetric ligation in three sets of pAL vectors, showing potential upstream and downstream amino-acid linkers to fusion peptides or protein domains in three reading frames (RF).

Linker amino acids (aa) in sequential positions are separated by a dash; a single aa allowed at a position is in lower case three-letter code; multiple aa allowed at a position are in upper case single-letter code; multiple aa excluded at a position are enclosed in brackets where the majority of aa are allowed.

FIGS. 6A-6B depicts all pairwise matches of overhangs for cloning 2 or 3 coding sequences by asymmetric ligation in pAL1. Overhangs of coding sequences are designed to be generated by digestion with T4 DNA polymerase in the presence of dCTP Abbreviations; SD is Shine-Dalgarno; us is upstream; ds is downstream; C at the end means complement.

In each matrix, 0 is no bp; 1 is a usual DNA bp; - is a GT match; perfect matches are circled. The two matches given between overhangs of unequal lengths are the ungapped alignments at the left and right ends.

DETAILED DESCRIPTION

The present invention provides vectors and methods for cloning, maintaining, and expressing coding sequences in inducible T7 expression systems.

The coding sequences include polynucleotides that encode for a target protein.

Strategy for Improving Vectors

Part of the strategy for improving vectors is to include an Expression Control Region as described below.

Ideally, basal expression would be reduced to a level where intervals between stochastic bursts of transcription and translation of a target gene in an uninduced cell are appreciably longer than a division cycle. If so, and if the amount of target protein produced per burst is low enough, any expression clone could be maintained in a growing culture in an inducible state. Even if every cell in which a burst of target gene expression occurred were to be killed or prevented from dividing, continuing division of unaffected cells would increase the population of cells that remain capable of induction faster than dead cells would accumulate. The longer the average interval between stochastic bursts of target gene expression relative to division time, and the smaller the average burst of target protein produced, the greater the fraction of cells in the culture that will remain fully competent for inducible production of target protein. The amount of target protein produced upon induction of the culture will then depend primarily on the fraction of inducible cells in the culture and the effect (if any) of target protein on the ability of the induced cell to produce protein.

Figure 1:
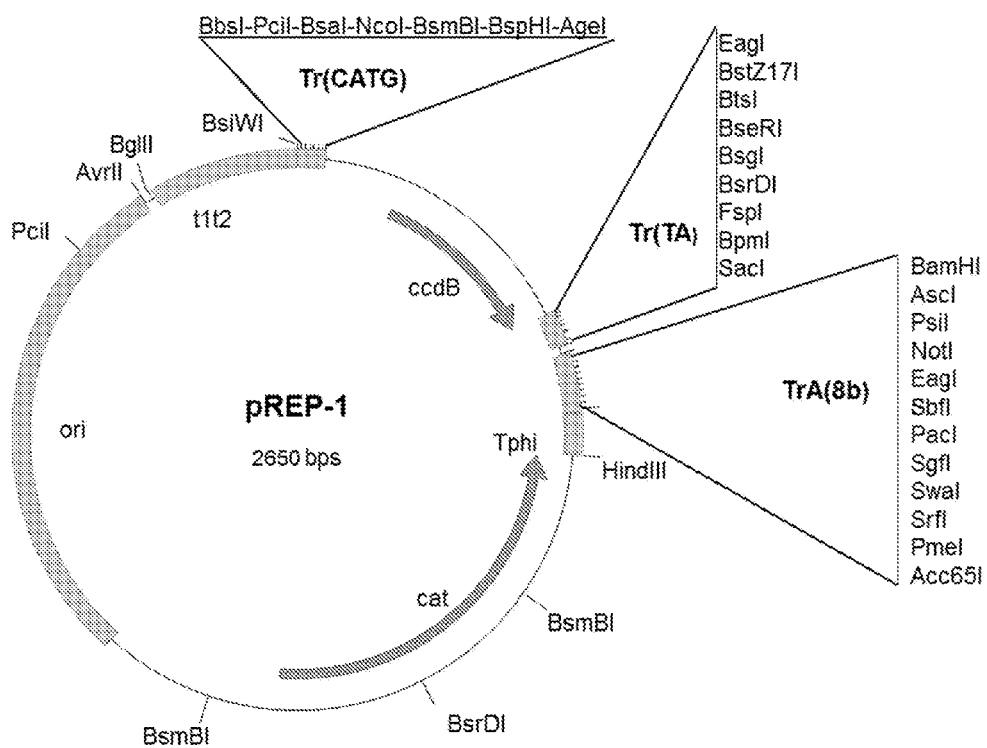
FIG. 1 depicts a plasmid map of pREP-1 vector, SEQ ID NO. 1.
Figure 3:
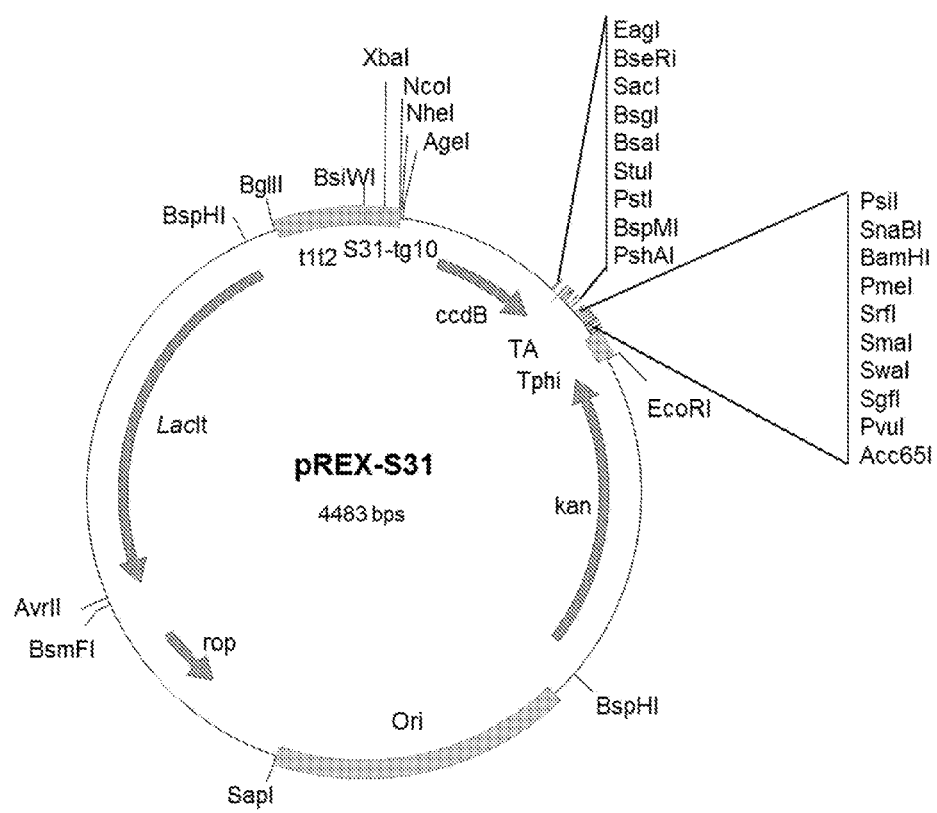
FIG. 3 depicts a plasmid map of pREX-S31 vector, SEQ ID NO. 62.

The strategy for obtaining vectors capable of producing virtually any target protein in an inducible T7 expression strain was to design, construct, test and improve two sets of vectors: 1) pREP vectors (FIGS. 1-2) having a cloning and retrieval site that can accept and maintain a coding sequence with the least possible expression, and 2) pREX vectors (FIG. 3) having an Expression Control Region that regulates and directs production of target protein in an inducible T7 expression strain, and an adjacent cloning site that accepts a coding sequence retrieved from a pREP clone and places it under control of the Expression Control Region. These new vectors were derived from pET vectors and were designed to eliminate superfluous DNA, minimize the potential for basal production of target protein, and to be modular, so that different components can be tested and exchanged easily through (mostly) unique restriction endonuclease cleavage sites. Several pREP vectors were designed but all of the coding sequences tested were easily cloned, maintained and retrieved from pREP-1 (SEQ ID NO. 1), which has been used almost exclusively. Many different pREX vectors have been constructed and tested, as disclosed herein.

In addition to using the T7 gene 5.3 coding sequence to test ability to maintain and express highly toxic target genes, the well-expressed T7 gene 10a coding sequence for the major T7 capsid protein has been used to test expression levels.

Construction of pREP and pREX Vectors

The pREX vectors contain approximately the minimal origin of replication of pET vectors, including the rop gene that ensures moderate copy numbers. However, the pREP-1 origin was further reduced to eliminate the rop gene, and pREP-1 has a considerably higher copy number characteristic of pUC vectors. The higher copy number of pREP-1 is meant to facilitate plasmid isolation for sequencing and retrieval of cloned coding sequences. The moderate copy number of pREX vectors is meant to make it easier to achieve lower levels of basal expression while retaining high levels of induced production of target protein typical of pET vectors.

To minimize the potential for synthesis of target mRNA by *E. coli* RNA polymerase (or RNA polymerases of any host cell), all known coding sequences in the cloning-acceptor fragment of both pREP-1 and pREX vectors plus the actively synthesized RNA I of the replication origin are oriented so that readthrough transcription that might reach a cloned target coding sequence will produce anti-sense RNA. RNA II, which primes replication of the plasmid in the opposite orientation of RNA I is the only known exception, and the t1t2 double transcription terminator of the rrnB ribosomal RNA operon placed immediately upstream of the cloning and retrieval site in pREP-1 and the Expression Control Region of pREX vectors (and the pAL vectors derived from them) is meant to minimize potential synthesis of target mRNA from possible readthrough transcription from RNA II or unknown or adventitious promoters for a host RNA polymerase.

A different selective agent together with a common counter-selection module facilitates cloning and transfer of coding sequences between pREP-1 and pREX vectors. The cat gene confers resistance to chloramphenicol in pREP-1 and the kan gene confers resistance to kanamycin in pREX vectors. Other genes have been contemplated and may be used herein. Examples of other genes that can be used for selection include the $amp^R$ gene which confers resistance ampicillin, and the $tet^R$ gene which confers resistance to tetracycline.

The counter-selection module (SEQ ID NO. 2) constitutively expresses the ccdB toxin of the *E. coli* F factor from the upstream expression signals for the ccdA anti-toxin gene, which has been deleted. The ccdB toxin kills cells used for cloning and expression by interrupting the action of DNA gyrase, thereby eliminating the background of unwanted colonies containing uncut or reconstituted vectors on transformation plates for selecting clones (Bernard et al. (1994) Gene 148:71-74; and U.S. Pat. Nos. 6,180,407 and 5,910,438 to Bernard et al., the contents of which are incorporated herein by reference). Recognition sites for several restriction endonucleases were eliminated from the counter-selection module to ensure that counter-selection would not be inactivated in cloning or retrieval processes involving pREP, pREX or pAL vectors. All three types of vectors must be maintained in and produced from a host that is resistant to the ccdB toxin. The gyrA462 mutation provides resistance and strain DB3.1™ (Invitrogen, *E. coli* RR1 gyrA462 endA recA) is a suitable host. However, the ccdB Survival™ strain that replaced DB3.1 in the Invitrogen/Life Technologies catalog, which attempts to counter ccdB toxin by producing ccdA anti-toxin, was found to be unsatisfactory because vectors maintained in this host frequently lost the ability to kill the usual transformation hosts.

Other counter selection genes have been contemplated and may be used in the vectors disclosed herein. Examples of other counter selection genes include sacB, rpsL, tetAR, pheS, thyA, lacY, and gata-1. See Reyrat et al., Infection and Immunity, September 1998, p. 4011-4017.

Figure 4:
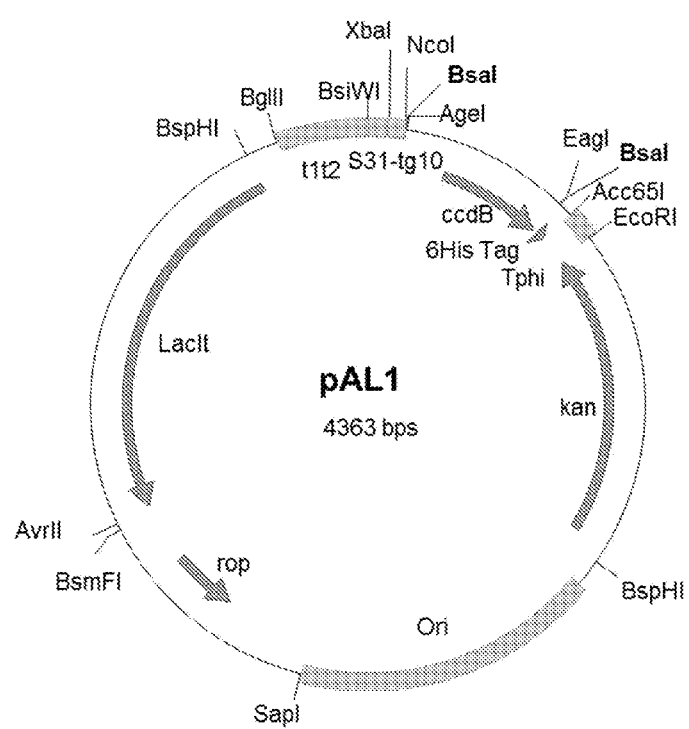
FIG. 4 depicts a plasmid map of pAL1 vector, SEQ ID NO. 66.

Both pREP and pREX vectors have clusters of recognition sites for other restriction endonucleases following the downstream acceptor site, in anticipation that they might be useful for cloning in special situations (FIGS. 1 and 3); however, they have not been used and are not included in pAL vectors (FIG. 4). The Tphi terminator of transcription by T7 RNA polymerase from T7 DNA follows these superfluous cloning sites in both pREP and pREX vectors. Besides limiting extensive readthrough transcription past the target mRNA in pREX after induction, Tphi provides a 3' stem-loop structure that makes target mRNA considerably more stable than most *E. coli* mRNAs.

Cloning and Retrieval Site in pREP-1 and Acceptor Site in pREX Vectors

Any coding sequence with an upstream 5'-CATG single-stranded DNA overhang and a downstream TA-3' overhang can be perfectly paired to complementary acceptor overhangs in the cloning and retrieval site of the cloning-acceptor fragment of pREP-1 to provide substrates for rapid ligation (FIG. 2 and SEQ ID NOs. 3 and 4). The resulting clone contains restriction endonuclease cleavage sites that allow retrieval of the coding sequence with the same overhangs. (Nucleotide sequences are given left to right in the 5' to 3' direction unless specified otherwise, using the DNA single-letter designations for both DNA and RNA.) The ATG in the upstream overhang of the coding sequence specifies the initiation codon and the downstream TA immediately follows the codon for the last amino acid of the coding sequence. The cloning-acceptor fragment of pREX vectors accepts the upstream 5'-CATG overhang at a complementary overhang produced by cleavage at a unique NcoI site that ends the Expression Control Region (SEQ ID NO. 6), and accepts the downstream TA-3' overhang at a complementary overhang produced by cleavage at a unique BseRI cleavage site (SEQ ID NO 7).

The downstream TA acceptor in pREX vectors is followed by an A nucleotide to create a TAA termination codon, thereby directing expression of the exact target coding sequence. Equivalent pairs of pREP and pREX vectors could also be constructed with TG instead of TA as the downstream overhang (FIG. 2 and SEQ ID NO. 5).

The CATG and TA overhangs were chosen for flexibility to produce target proteins fused to N- and/or C-terminal peptides or protein domains supplied by coding sequences in different pREX vectors through linkages as short as 0-3 amino acids. However, much more construction and modification of pREX vectors than anticipated was required to obtain the desired significant reductions in basal expression, and fusions to target proteins have instead been developed in the more convenient and versatile pAL vectors.

Various Type IIS restriction endonucleases have a non-palindromic (asymmetric) recognition sequence and cut at specific positions outside of the recognition site regardless of the sequence at the cut sites. Since the distance between recognition and cleavage sites can be appreciably different for different enzymes, two or more recognition sequences for different Type IIS and Type II restriction endonucleases can be placed so that each of the enzymes cuts to produce the same acceptor overhang for cloning. The upstream cloning and retrieval site in pREP-1, designated Tr(CATG) (FIG. 2 and SEQ ID NO. 3), contains 6-bp recognition sequences for three pairs for Type IIS and Type II restriction endonucleases, placed so that each member of a pair cuts to produce 5'CATG overhangs at the same position, so that an acceptor overhang can optionally be generated at any of three sites. In clockwise (left-to-right) order the three pairs of recognition sequences for this first set of restriction nucleases is BbsI-PciI, BsaI-NcoI and BsmBI-BspHI and they are preceded by a unique BsiWI site and followed by a unique AgeI site. Likewise, the downstream cloning and retrieval site, designated Tr(TA) (FIG. 2 and SEQ ID NO. 4), contains 6-bp recognition sequences for two triplets of Type IIS restriction endonucleases, placed so that each member of a triplet cuts to produce TA-3' overhangs at the same position, so that an acceptor overhang can optionally be generated at either of two sites. The clockwise order of the two triplets of recognition sequences for this second set of restriction endonucleases is BtsI-BseRI-BsgI and BsrDI-EciI-BpmI and they are preceded by an EagI site and followed by a unique SacI site. At least one recognition sequence in each pair or triplet is unique in pREP-1, so each of the three upstream and two downstream acceptor overhangs can be generated individually. As noted above, equivalent pairs of pREP and pREX vectors could also be constructed with TG instead of TA as the downstream acceptor overhang (FIG. 2 and SEQ ID NO. 5).

The vast majority of coding sequences will lack a 6-bp recognition site for at least one of the six restriction endonucleases in the upstream set and at least one of the six restriction endonucleases in the downstream set. Such coding sequences can be amplified by PCR using forward and reverse primers that each supply the recognition and cleavage sequence in the position and orientation such that cutting the PCR product with two restriction endonucleases that do not cut within the coding sequence will generate the upstream 5-CATG and downstream TA-3' (or TG-3') overhangs for cloning. The coding sequence can be retrieved from the pREP-1 clone for transfer to a pREX vector by cutting with the same two restriction endonucleases used to produce the DNA fragment cloned even if other cleavage sites are present elsewhere in the pREP vector, because the overhangs at outside sites will usually not compete significantly for cloning into the pREX acceptor overhangs. If necessary, coding sequences can be mutated or chemically synthesized to eliminate one or more internal cleavage sites for enzymes used in cloning and retrieval, but this was not necessary for any of the coding sequences tested.

Other Measures to Minimize Potential Expression of Active Target Protein in pREP-1

In addition to the previously discussed measures taken to prevent or reduce potential transcription of cloned coding sequences in pREP-1, the sequences ahead of the initiation codon for the cloned target protein in the three upstream cloning acceptors are designed, as much as possible, to be unfavorable for ribosome binding and initiation of target protein synthesis from any target mRNA that might happen to be made. Furthermore, the target coding sequence does not terminate at either of the two TA-3' downstream cloning acceptors in pREP-1 (SEQ ID NO. 1) but continues for 54 amino acids past the first acceptor site and 11 amino acids past the second acceptor site before terminating, thereby generating C-terminal fusions that may diminish the toxicity of any target protein that might happen to be produced. Every toxic T7 gene tested and every target coding sequence obtained from collaborators who were unable to obtain clones in pET vectors was easily cloned, maintained and retrieved from pREP-1.

Expression Control Region of pREX and pAL Vectors

The Expression Control Region of the invention includes a T7 Promoter Control Region and Translation Initiation Efficiency Region as described below.

The DNA sequence between the end of the t1t2 double transcription terminator sequence and the ATG initiation codon for the target protein in pREX and pAL vectors is referred to here as the Expression Control Region (ECR). As with many pET and other vectors, the ECRs of pREX and pAL vectors are derived from elements in T7 DNA that direct expression of the T7 gene 10 major capsid protein, the most highly expressed protein during T7 infection, combined with one or two binding sites for lac repressor (Rosenberg et al. (1987); Studier et al. (1990); Dubendorff et al. (1991); U.S. Pat. No. 6,537,779 (2003)). Expression Control Regions of pET-3a, pET-11d, ZA #11 and ZA #13 are aligned with the ECR of T7 gene 10 in Table 1 to highlight similarities and differences (SEQ ID NOs. 8-12).

Expression Control Regions of pREX and pAL vectors are here divided into a T7 Promoter Control Region (TPCR), which directs transcription of the target gene, and adjacent Translation Initiation Efficiency Region (TIER), which largely determines how well target mRNA competes for binding to ribosomes and initiation of translation to produce target protein. The TPCRs and TIERs that comprise the ECRs of different pREX and pAL vectors are also aligned with the ECRs of T7 gene 10 and previous vectors in Table 1. The TPCRs of pREX and pAL vectors disclosed herein are identified in Tables 1 and 3 and/or with SEQ ID NOs. 13-47, and TIERs disclosed herein are identified in Tables 1-3 and/or with SEQ ID NOs. 48-59.

In clockwise order (left to right in Table 1), the TPCRs in those pREX and pAL vectors that have a single lac operator comprise: a BsiWI site and overlapping six base pairs of T7 DNA ahead of the T7 gene 10 promoter sequence; the 17-bp upstream T7 promoter sequence; 1-4 G residues that initiate RNA from the T7 promoter; and a downstream minimal lac operator that is linked to the XbaI site that begins the TIER. The link between TPCR and TIER is 0-4 bp long or through a single base-pair overlap between the last base pair of the lac operator and first base pair of the XbaI site (Tables 1 and 3). A second lac operator upstream of the T7 promoter in some pREX and pAL vectors begins immediately after a SacII site and comprises a 37-bp lacO1 operator with its natural extended palindrome positioned ahead of the BsiWI site at or near the optimal distance from the downstream lac operator for repression of transcription, as determined by Muller et al. (1996) J. Mol. Biol. 257:21-29.

In certain embodiments, the cgtacgaaat sequence at the 5' terminus of the TPCR may be substituted with another restriction enzyme site, no restriction site, or a nucleic acid sequence of identical length that does not contain a restriction site.

Modifications to the terminal sequence of the TIER have been contemplated. For example, the XbaI sequence (TCTAGA) and NcoI sequence (CATG) of the TIER may be modified. In particular, the XbaI sequence can be replaced with another restriction enzyme site or no restriction enzyme site at all. However, in certain embodiments, it is important to maintain a sequence of six nucleic acid residues at the 5' terminal end of the TIER region polynucleotide.

Combinations of T7 Promoter Control Region and Translation Initiation Efficiency Region have been contemplated. Any T7 Promoter Control Region may be paired with any Translation Initiation Efficiency Region.

Different elements in the Expression Control Region and short linker sequences between them have been the primary focus of testing and modification to reduce basal expression and improve the capabilities of pREX vectors and the pAL vectors derived from them. Five types of variation were evaluated (Tables 1-3): 1) initiating target mRNA with 1, 2, 3 or 4 consecutive G residues ahead of a minimal lac operator; 2) the relative effectiveness of a downstream asymmetric lacO1 or perfectly symmetric lacS minimal operator; 3) different lengths and compositions of base pairs linking the downstream lac minimal operator with the Translation Initiation Efficiency Region; 4) different lengths and compositions of base pairs within the TIER; and 5) adding the 37-bp lacO1 and extended palindrome upstream of the T7 promoter at or near the optimal distance for repression. Effects of these targeted variations are disclosed in following sections.

The TIER in most pREX vectors disclosed herein is tg10 (Table 1 and SEQ ID NO. 48) and pREX vectors having tg10 may be identified simply by their TPCR designation, e.g. LS31 (designations are defined in Table 3). Other TIERs investigated are given in Table 2, and pREX vectors may be identified specifically by a compound TPCR-TIER designation to certify which TIER it contains, e.g. S31-tr5 or S31-tg10.

lacIt Gene in pREX and pAL Vectors

The lacI gene in pET vectors is meant to supply enough lac repressor to saturate all of the lac operators in an uninduced T7 expression strain such as BL21(DE3) in which bound lac repressor blocks expression of T7 RNA polymerase and the lac operon by E. coli RNA polymerase from different lac promoters in the chromosome and also blocks expression of target protein by T7 RNA polymerase from a T7lac promoter in the multi-copy vectors. However, transcription and translation-initiation signals for producing lac repressor from the lacI gene are known to be relatively weak, and it seemed likely that supplying a higher concentration of lac repressor in the cell might increase occupancy of the lac operators and thereby reduce basal expression of both T7 RNA polymerase and target protein with little effect on induced expression. Accordingly, two modifications to the sequence upstream of the lacI gene (SEQ ID NO. 60) were made in a pREX L44 vector, which has an Expression Control Region equivalent to that of pET-11d (Table 1 and SEQ ID NOs. 10 and 13): 1) introduction of the $lacI^q$ mutation in the promoter for expressing lacI, a single-bp change in the −35 region (GCGCAA to GtGCAA) that is known to increase transcription of lacI by E. coli RNA polymerase (Calos (1978) Nature 274:762-765); and 2) changing the initiation codon for lac repressor from GTG to ATG and exchanging the upstream 13 base pairs with an AT-rich sequence with an appropriately spaced Shine-Dalgarno (SD) sequence to increase translation of lacI mRNA, a modification designated lacIt (SEQ ID NO. 61). A pREX vector containing both modifications was found to be unstable, presumably because the concentration of lac repressor was high enough to stress the cell. However, lacIt without the $lacI^q$ mutation is well tolerated in pREX vectors and production of T7 10a protein after induction is comparable to that obtained in pET vectors. Therefore, lacIt has been included in pREX and pAL vectors rather than the natural sequence upstream of the lacI coding sequence, in the expectation that it generates a somewhat higher concentration of lac repressor and greater occupancy of lac operators in the uninduced cell, thereby reducing basal expression of both T7 RNA polymerase and the target protein more effectively.

During initial construction of pREX vectors, the lacIt gene was oriented so as to be transcribed in the same direction as the target gene. After changing the orientation, it was found that the unintended lacIt orientation by itself prevented establishment of a 5.3 clone that could be maintained in an otherwise identical vector having lacIt in the intended orientation. Apparently, a significant fraction of E. coli RNA polymerases that initiate transcription at the weak lacI promoter continue past the t1t2 double transcription terminator and through the uninduced Expression Control Region to produce functional target mRNA. The intended lacIt orientation (transcribed in the opposite direction from the target gene) is standard in pREX and pAL vectors. The t1t2 termination module has been retained but could possibly be eliminated with little consequence.

EXAMPLES

The present invention is illustrated in further details by the following non-limiting examples.

Testing and Improvement of pREX Vectors

The host strain used for initial cloning has been XL1Blue-MR, referred to here as XL1B (from Stratagene, now Agilent Technologies, Inc.), which lacks known DNA restriction systems, requires thiamine for growth, and has no gene to supply T7 RNA polymerase. The hosts used for expression under control of inducible T7 RNA polymerase are BL21(DE3) (from Novagen, now EMD Millipore) and BL21-AI (from Invitrogen, now Life Technologies, part of Thermo Fisher Scientific) as well as newly isolated variants of BL21(DE3) described in a later section The first pREX vector tested had the Expression Control Region L44-tg10, equivalent to that of pET-11d (Table 1). This vector produced high levels of T7 gene 10a capsid protein but was unable to maintain the gene 5.3 coding sequence received from pREP even in XL1B (Tables 2 and 3). Since XL1B does not supply T7 RNA polymerase, inability to establish a functional 5.3 clone implies that the target gene is somehow being transcribed by *E. coli* RNA polymerase, which can initiate transcription at a wide range of sequences. It seemed likely that one or more weak promoters for *E. coli* RNA polymerase upstream of the target coding sequence was directing production of enough of the highly toxic 5.3 protein that clones could not be tolerated.

Examination of the tg10 sequence identified two sequences, TAattT and TAactT (underlined in Table 2), that contain the most highly conserved base-pairs in the TAtaaT consensus sequence for the −10 region of promoters for *E. coli* RNA polymerase, either of which would direct transcription of target mRNA. Expecting that eliminating or altering one or both of these sequences might reduce basal expression sufficiently to allow stable maintenance of clones capable of producing functional 5.3 protein, deletions and alterations between the XbaI site and the Shine-Dalgarno (SD) sequence of pREX L44-tg10 were constructed and tested (Table 2). As a control, the entire Translation Initiation Efficiency Region between the XbaI and NcoI sites was replaced with the equivalent fragment from pREP-1, which had been designed to be unfavorable for binding ribosomes and initiating target protein synthesis (tr3 in Table 2).

As summarized in Table 2, the 5.3 coding sequence could be cloned in pREX L44-tr3 and maintained with little evidence of stress in XL1B and both T7 expression hosts BL21(DE3) and BL21-AI. Other alterations to tg10 in L44 also enabled 5.3 clones to be established in XL1B, although usually at lower efficiency and with smaller colony sizes than 10a clones, indicating that some basal expression directed by *E. coli* RNA polymerase remained in most or all of them. These clones could also be maintained in BL21-AI but were more stressful to varying degrees in BL21(DE3), consistent with a higher basal level of T7 RNA polymerase. Induction of clones in BL21-AI stopped the growth of the culture, indicating that active 5.3 protein was produced; however, not enough protein accumulated to be apparent in a stained gel after SDS-electrophoresis of whole-cell extracts.

Controlling Rates of Translation Initiation

Each of the above pREX L44 vectors having a variant TIER was also tested for ability to produce 10a protein in BL21(DE3). As expected, the tr3 replacement of essentially the entire tg10 TIER with a sequence that lacks recognizable translation initiation signals reduces production of 10a protein to a level barely if at all detectable in stained electrophoresis gels (Table 2). Unexpectedly, L44-tr1, which retains the entire Shine-Dalgarno (SD) sequence through the initiation codon but only 5 of the 28 base pairs of tg10 upstream of the SD sequence, produced only barely detectable amounts of 10a protein. Interestingly, production of 10a protein increases gradually with increasing retention of tg10 sequence upstream of the SD sequence and reaches levels typical of L44-tg10 when ~15 or more base pairs are retained (Table 2).

Natural T7 gene 10 mRNA begins with a 21-bp stem-loop structure that ends immediately ahead of the XbaI site that begins tg10 and continues with a 28-nucleotide (nt) largely unstructured AT-rich sequence ahead of the SD sequence AAGGAG (Table 1). Target mRNA from L44 vectors also begins with a large stem-loop structure that ends immediately ahead of the XbaI site, in this case a 29-bp interrupted palindrome that encompasses the lacO1 operator. A likely explanation for the reduction of protein production caused by deletions between the XbaI site and SD sequence of the tg10 TIER is that positioning a rather large and stable RNA structure too close to the SD sequence interferes with binding of the mRNA to the ribosome and reduces the frequency of initiation of synthesis of target protein. This apparent ability to control rate of translation simply by changing the distance between a relatively stable RNA structure and an intrinsically strong, relatively unstructured upstream protein-initiation sequence may prove useful, as the solubility of some target proteins has been reported to increase when rates of protein production are reduced. The same strategy should also be applicable to the 20-bp completely symmetrical palindrome in the lacS operator in T7lac promoters constructed subsequent to these experiments (Table 1).

Vectors that Reduce Basal Expression by T7 RNA Polymerase and *E. coli* RNA Polymerase Although deletions in tg10 allowed pREX clones of the coding sequence for the highly toxic 5.3 protein of T7 to be maintained and expressed in BL21-AI, most of these clones could be established only with considerable difficulty if at all in BL21(DE3) (Table 2). Therefore, changes to other elements in the Expression Control Region of pREX vectors were tested for ability to reduce basal transcription of the target gene by the somewhat higher basal levels of T7 RNA polymerase in BL21(DE3) and thereby increase the stability and range of clones that can be established and expressed in BL21(DE3) or any inducible T7 expression host. Surprisingly, some combinations of modifications that do not affect tg10 at all reduce basal transcription of target gene not only by T7 RNA polymerase but also by *E. coli* RNA polymerase to levels where pREX or pAL clones of the 5.3 coding sequence and every other coding sequence tested, many of which specify proteins highly toxic to the host, can be maintained and expressed in BL21(DE3).

The approach was to try to enhance the ability of bound lac repressor to block transcription of the target gene by T7 RNA polymerase. The frequency of T7 RNA polymerase transcription through an operator saturated with specifically bound lac repressor is known to increase with distance between the T7 promoter and operator (Dubendorff et al. (1991) and Giordano et al. (1989)), so decreasing the distance between T7 promoter and lac operator might be expected to decrease basal transcription of target gene by T7 RNA polymerase. The T7lac promoter in pET vectors initiates RNA chains 4 bp ahead of the AATT sequence that begins the 21-bp interrupted palindrome that constitutes the minimal natural lacO1 operator (pET-11d and pREX L44-tg10 in Table1). The RNA produced by T7 RNA polymerase begins GGGGAA, a sequence very similar to the conserved GGGAGA start of the RNAs from the six strongest T7 promoters in T7 DNA. Addition of CCCC residues at the other end of the T7lac operator extends the palindrome by 4 perfect base pairs, similar to extensions of the palindrome flanking the natural lacO1 operator (upstream 37-bp lacO1 in Table 1).

Three approaches to decreasing basal transcription of the target gene by T7 RNA polymerase were taken: 1) exploring effects on basal and induced expression of moving the lac operator closer to the RNA start position; 2) replacing the 21-bp natural lacO1 operator with a 20-bp operator that is a perfect palindrome (referred to here as lacS), which is known to bind lac repressor with a higher affinity (Muller et al. (1996) J. Mol. Biol. 257:21-29); and 3) adding a 37-bp lacO1 operator with its extended natural palindrome upstream of the T7 promoter-lacS sequence such that the center-to-center spacing between the two operators is 70.5 bp for T7 promoters that begin RNA with GGGAA, the spacing expected for maximum repression (Muller et al. (1996)). For convenience in vector construction, the spacing is 69.5 bp for T7 promoters that begin RNA with GGAA, which seems to have comparable effect. The names, nucleotide sequences and SEQ ID NOs. of different T7 Promoter Control Regions and Translation Initiation Efficiency Regions that comprise Expression Control Regions of pREX and pAL vectors are given in Tables 1-3, and results of cloning and expression tests are given in Tables 2 and 3.

Initial experiments to test the effect of moving the lacO1 operator closer to the T7 promoter by progressive shortening of the four consecutive G residues that begin the RNA produced from the T7lac promoter used in pET vectors also shortened the four consecutive C residues between the lac operator and tg10, so the observed improvements in ability to clone the 5.3 coding sequence were probably due primarily to shortening the linker between the operator and tg10, as discussed in more detail below (Table 3). Shortening the RNA start from GGGGAA to GGGAA had no apparent effect on levels of 10a protein produced after induction in either BL21(DE3) or BL21-AI; shortening to GGAA had little if any effect on level of 10a protein produced in BL21(DE3) but moderately reduced the level produced in BL21-AI; and shortening to GAA severely reduced 10a protein production in both hosts. All of the natural T7 promoters in T7 DNA begin RNA with at least two of the first three nucleotides being G, and apparently a GAA start is unfavorable. In one embodiment, the RNA start includes GGGGAA, GGGAA, GGAA, GGAGAA, GAGGAA, GAGAA, AGGAA, or AGGGAA. Examples of T7 Promoter Control Regions having the afore-mentioned RNA start sequences are disclosed herein and provided, for example, in SEQ ID NOS. 13-32 and 94-102.

T7lacS promoter-operator combinations appeared to be superior to T7lacO1combinations for maintaining and expressing 5.3 clones in all configurations in which they were compared, and expression levels of 10a protein after induction were comparable. Therefore, the symmetric lacS operator was used in most tests of effects of moving the lac operator closer to the T7 promoter and shortening the sequence between the AATT that ends the lacS operator and the XbaI recognition sequence TCTAGA that begins tg10 (Table 3). Substituting a G residue for one or both of the A residues that begin the minimal lac operator sequence decreased the ability to maintain and express 5.3 clones (not shown in Table 3), presumably due to weaker binding of lac repressor to the altered operator sequence.

The length of consecutive C residues separating the lac operator from tg10 was found to have a substantial effect on the level of basal expression of the target gene due to transcription by E. coli RNA polymerase. Vectors linking these two regions through CCCC were unable to clone the 5.3 coding sequence in XL1B regardless of changes in spacing between the T7 promoter and lac operator or the presence of a second operator upstream of the T7 promoter (Table 3). This configuration, also found in many pET vectors and in vectors described by Kara et al. (U.S. Pat. No. 6,537,779), is apparently unsuitable for cloning and expressing a considerable range of proteins that stress E. coli expression hosts. Changing the linker between lacS and tg10 to AGGG gave marginal improvement in some configurations but was generally unsatisfactory as well (not shown in Table 3). Shortening CCCC to CCC or CC without changing the number of G residues that begin the RNA improves ability to clone 5.3 in XL1B, although cells are obviously stressed in some configurations, and transfer to BL21(DE3) or BL21-AI for expression can remain problematic or impossible (Table 3). The best configurations for cloning 5.3 in XL1B and for transferring clones to and expressing them in hosts that supply T7 RNA polymerase are when the linkage between lacS and tg10 consists of a single C, no base-pair at all, or where the lacS operator and XbaI site overlap by a single T. Presumably, replacing the single C with an A, G, or T residue at this position would have a similar effect. Reducing basal expression due to transcription of the target gene by E. coli RNA polymerase in this way is superior to deleting potential promoter elements in tg10 (compare Tables 2 and 3).

Simply moving the lacS operator one or two bp closer to the T7 promoter than the 4-bp distance in the T7lac promoter appears to have had minimal effect on decreasing basal transcription by T7 RNA polymerase (Table 3). However, placing a lacO1 operator with its natural extended palindrome upstream of the T7 promoter sequence at a spacing between the lacO1 and lacS operators close to that reported to provide maximum repression (Muller et al. (1996) J. Mol. Biol. 257:21-29) substantially improves the ability to clone, maintain and express the 5.3 coding sequence. This enhancement could be due to the ability of tetramer lac repressor to bring the two operators together, forming a DNA loop that interferes with binding of T7 RNA polymerase, or an increase in occupancy of the lacS repressor-binding site, or both.

Controlling Rates of Target Protein Production

Induced levels of 10a protein in BL21(DE3) are comparably high for all vector configurations in which target mRNA begins with GG, GGG, or GGGG and whether or not an upstream operator is present (Table 3). However, at least three different levels of induced expression are apparent in BL21-AI, depending on these factors (Table 3). The lower levels of production in BL21-AI seem likely to be due to a lower induced level of T7 RNA polymerase in BL21-AI.

Controlling rates of production of target protein by combining different T7 Promoter Control Regions and Translation Initiation Affinity Regions characterized in Tables 1-3 in different vectors and hosts may be useful in producing functional proteins if significant numbers of proteins have increased solubility or are better able to fold correctly at lower rates of transcription or translation, as reported for some proteins. The ability to control basal and induced transcription by T7 RNA polymerase or other T7-like RNA polymerases, combined with cell-specific translation signals might also have application in producing proteins in other types of cells or for synthetic biology Asymmetric Ligation and Cloning in pAL Vectors Although the pREP-pREX system has been useful both for testing different vector configurations and for producing proteins, a simpler cloning system for efficient and high-throughput cloning of coding sequences in vectors that incorporate the improvements developed in pREX vectors has been designed and implemented. The method is referred to here as asymmetric ligation and the vectors for cloning by asymmetric ligation are called pAL vectors.

Many cloning vectors, including pREP and pREX vectors, have directional cloning sites generated by cutting with restriction endonucleases that produce a different symmetric (self-complementary) overhang at each end of the cloning-acceptor fragment. These cleavages produce 3' hydroxyl and 5' phosphate ends that are substrates for covalent joining by a DNA ligase such as T4 DNA ligase, which efficiently joins double-stranded DNAs that have the same symmetric overhang (such as 5'-CATG or TA-3' in pREP and pREX vectors) by sealing the nick at each end of perfectly base-paired overhangs. In a ligation reaction mixture, the equilibrium between base-paired and unpaired symmetric overhangs greatly favors unpaired overhangs, but the rate of ligation increases with ligase concentration and, under appropriate conditions, T4 DNA ligase can join both nicks in essentially all perfectly paired 4-nt overhangs in less than a minute at room temperature (Shore et al. (1981) Proc. Natl. Acad. Sci. USA 78:4833-4837).

Directional cloning by ligation of symmetric overhangs requires two steps: 1) an initial ligation to join one end of a cloning-acceptor fragment to the complementary end of a target fragment through perfectly paired symmetric overhangs, and 2) a subsequent ligation to join the other ends through their perfectly paired symmetric overhangs to complete the circular clone before either end can be joined through perfectly paired overhangs to another linear fragment. Ungapped perfectly paired symmetric overhangs direct efficient ligation between any linear molecules in the reaction mixture indiscriminately, and the many competing nonproductive reactions mean that the desired clone is typically a minor component of ligation products. Nevertheless, the desired pREP or pREX clone can usually be obtained simply by transformation of the ligation mixture, because strong selection for antibiotic resistance and counter-selection against the ccdB module will eliminate most of the unwanted clones.

Ligases have long been known to join double-stranded DNAs at ungapped perfectly base-paired overhangs much more rapidly than where imperfectly aligned overhangs have gaps or mismatches at or near the ends to be joined (e.g. Wu et al. (1989) Gene 76:245-254 for T4 DNA ligase). Asymmetric ligation takes advantage of this specificity to greatly increase the efficiency of directional cloning. Asymmetric overhangs of all DNAs in the ligase reaction mixture are designed so that the only ungapped perfectly base-paired overhang alignments are those whose ligation will produce the desired clone or regenerate the cloning vector and, crucially, such that all of the other possible overhang alignments have few if any aligned base pairs near their ends and therefore a much smaller probability of being ligated. In the pAL vectors constructed so far, overhangs in the cloning-acceptor fragment are generated by the Type IIS restriction endonuclease BsaI, which cuts to one side of an asymmetric recognition site to produce 4-nt 5' overhangs that can have any sequence. The only two BsaI recognition sites in these vectors flank the same ccdB counter-selection module used in pREP and pREX vectors and are oriented outward, so that cutting with BsaI produces a cloning-acceptor fragment with the desired asymmetric overhang at each end and a ccdB-containing fragment that contains both BsaI recognition sequences and has asymmetric overhangs complementary to those of the cloning-acceptor fragment (map of pAL1 in FIG. 4). Of course, any Type IIS restriction endonucleases that cut outside of their recognition sequence to produce 4-nt 5', 3-nt 5' or possibly even 2-nt 5' or 2-nt 3'overhangs of arbitrary sequence would also be suitable for generating asymmetric overhangs for cloning. For example, restriction endonucleases that provide a 4-nt 5' overhang include BsaI, BbvI, BcoDI, BsmFI, BsmBI, FokI, BfuAI, BbsI, and SfaNI; restriction endonucleases that provide 3-nt 5' overhang include SapI; 2-nt 5' overhang include FauI; and 2-nt 3' include BseRI.

To clone a single DNA in a pAL vector by asymmetric ligation, the target DNA must have the asymmetric 4-nt 5' overhang at each end that is perfectly complementary to the asymmetric 4-nt 5' overhang at the appropriate end of the cloning-acceptor fragment of the vector. The overhangs in a target DNA are routinely generated in a 5-minute reaction at room temperature in which the 3' exonuclease activity of T4 DNA polymerase removes the first four nucleotides at each 3' end of the double-stranded target DNA but stops at the fifth nucleotide because the only deoxynucleotide triphosphate (dNTP) present in the reaction mixture can be incorporated at this position by the polymerase activity, thereby preventing removal of additional nucleotides. The target DNA being digested has typically been amplified by PCR with a high-fidelity polymerase that produces blunt ends, using two PCR primers that have the appropriate five-nucleotide sequence at each 5' end, and the T4 DNase polymerase reaction mixture also contains T4 polynucleotide kinase to phosphorylate the 5' ends of the overhangs to make them substrates for ligation. Any target DNA that can be amplified by PCR can be cloned in this way regardless of whether it contains (or lacks) a site for cleavage by certain restriction endonucleases. Fragments suitable for cloning could also be produced by Type IIS cleavages at the ends of PCR amplified DNA, but only if the enzyme does not also cut within the sequence to be cloned.

A limitation in the use of T4 DNA polymerase in the presence of a single dNTP to generate overhangs for cloning is that none of the four nucleotides in an overhang should be the same as the fifth nucleotide from the 5' end. However, control tests of 5-minute reactions at room temperature with T4 DNA polymerase in the absence of any dNTP but in the presence of T4 polynucleotide kinase (to phosphorylate the 5' ends of overhangs) found that ligation of DNA treated in this way to BsaI-cut pAL1 produced ~20-50% as many clones as obtained when the target DNA had been digested in the presence of the appropriate single dNTP. These few control tests suggest that the limitation on composition of the overhang and requirement for a specific nucleotide at the fifth position from the 5' end could probably be bypassed if necessary or desirable in selecting pairs of 4-nt overhangs for cloning by asymmetric ligation, and perhaps other exonucleases could also be used to generate overhangs. However, so many different pairs of asymmetric 4-nt 5' overhangs are suitable for cloning by asymmetric ligation that the limitations of digestion by T4 DNA polymerase are relatively insignificant and these additional possibilities were not pursued. Chemical synthesis of DNA is becoming progressively cheaper and more accessible so that simply purchasing double-stranded DNA with a codon-optimized coding sequence and any specified overhang sequences is a feasible alternative.

The initial pAL vectors were designed to produce the target protein itself or fused to an N- and/or C-terminal peptide or protein domain, and a variety of Expression Control Regions and fusion partners are represented among pAL vectors already constructed and tested (Table 4 and SEQ ID NOs. 66-78). Three pairs of upstream and downstream overhangs of target DNA generated by T4 DNA polymerase are cloned by asymmetric ligation in different subsets of these vectors: CCATg-cAGTG and ACTCg-cAGTG are generated in the presence of dCTP, and CTGCa-tAGCG are generated in the presence of dTTP. Sequences are given in the 5' to 3'orientation left to right with the four overhang nucleotides capitalized; consequently, the 5' end of the upstream PCR primer for amplifying a target coding sequence is the five-nucleotide sequence given, and the 5' end of the downstream PCR primer is the complement of the five-nucleotide sequence given.

The pattern of base pairing in each of the 10 possible ungapped pairwise alignments between the four different 4-nt overhangs present in an asymmetric ligation reaction for cloning a single coding sequence are shown in FIGS. 5A-5C as a base pair matrix for each of the three pairs of overhangs. The two pairs of complementary overhangs that produce the desired clone each have a standard complementary DNA base-pair at all four positions of the alignment, the best substrate for ligation (represented as 1111 in the three base-pairing matrices illustrated in FIGS. 5A-5C). The remaining eight pairwise alignments have at most two of the four positions being either a standard base-pair (1001, 1010, or 0110) or the presumably much weaker G-T base-pair (indicated by a dash in FIGS. 5A-5C, i.e., 0-0 or -00-), which makes these eight overhang pairs much worse substrates for ligation. None of the imperfectly matched pairs of overhangs has more than 1 consecutive standard base-pair at either end. Also shown in FIGS. 5A-5C are the possible combinations of two or three amino acids to link upstream and downstream peptides or protein domains to the target protein in each of the three reading frames.

Cloning by asymmetric ligation in these pAL vectors is so efficient that transformation of 1 μl of a 5-minute room-temperature ligation reaction mixture typically produces tens of thousands of clones in XL1B or thousands in BL21(DE3) or BL21-AI, almost all of which are the desired clone. This is ~1-2 orders of magnitude more colonies than were typical in cloning by ligation of the symmetric overhangs in pREP or pREX vectors. Long coding sequences are also cloned efficiently by asymmetric ligation; the 4239-bp coding sequence for a 1413 amino-acid transporter cloned in pAL1 produced too many transformed colonies to count, and the six clones analyzed each contained the entire coding sequence. The presence of the ccdB counter-selection module in pAL vectors allows efficient cloning directly in BsaI-cut pAL vectors without having to purify the cloning-acceptor fragment. In typical ligation reactions, the cut vector and the fragment to be cloned are at equi-molar concentration. The overhangs of the cloning-acceptor fragment will pair perfectly for ligation only to the overhangs of the target fragment that produce the desired clone or to the overhangs of the ccdB fragment to regenerate the vector. Since the ccdB toxin prevents growth of cells containing incompletely cut or reconstituted vector, the vast majority of transformed colonies that grow in the presence of kanamycin (the selective antibiotic for pAL vectors) contain the desired clone. As with pREP and pREX vectors, pAL vectors must be maintained in a host such as DB3.1, which is resistant to the effects of the ccdB toxin.

Deriving pAL Vectors from pREX Vectors

The modular construction of pREX vectors made it relatively easy to derive the first pAL vectors from pREX S31-tg10 (FIG. 3 and SEQ ID NO. 62) to produce pAL1, 5, 11-14 and 21-24 (Table 4, which includes SEQ ID NOs.). The DNA fragments between the XbaI-AgeI and EagI-Acc65I sites flanking the ccdB counter-selection module were replaced with synthetic oligonucleotides or appropriately processed PCR products to: 1) introduce unique outward facing BsaI sites flanking the ccdB module (FIG. 4); 2) provide asymmetric overhangs to link target coding sequences to Expression Control Regions containing either the tg10 or tr5 Translation Initiation Efficiency Region, which provide different rates of translation (Table 2); and 3) specify N-terminal and/or C-terminal fusions to the target protein (Table 4). In these pAL vectors, direct linkage of the target coding sequence to the ATG initiation codon at the end of the Expression Control Region is through the CCATg overhang, which allows complete flexibility for all remaining codons that specify the target protein (Tables 1 and 4). The ATG initiation codon for N-terminal fusions to the target protein is in a CATATG NdeI site at the end of the Expression Control Region, as in T7 DNA (Tables 1 and 4).

N-terminal fusions are inflexible in an individual vector but C-terminal fusions are optional because the coding sequence to be cloned can either include a termination codon ahead of the overhang that joins it to the vector or can link in-frame through the overhang to the sequence encoding a C-terminal fusion. Examples of N-terminal and C-terminal fusions have been contemplated and include affinity tag (HIS, FLAG, Myc, or HA), fluorescent tag (GFP and CFP); targeting peptide (pelB or dsbA); and dimerization domain (dsbC).

The N-terminal fusions represented in the vectors listed in Table 4 are a Met-Ala-Ser-6His-Ser affinity tag and pelB or dsbA leader sequences that target proteins to the periplasm by the Sec or SRP pathway respectively. The optional C-terminal fusions represented are a Ser-Gly-6His affinity tag and a 73-amino-acid dimerization domain of the *E. coli* dsbC protein (a periplasmic disulfide isomerase) with or without an additional Gly-Ser-6His affinity tag.

The collection of pREX vectors already tested for ability to maintain and express target coding sequences is a valuable resource for constructing useful pAL vectors. Modular construction makes it easy to convert any pREX vector to a pAL vector simply by replacing the XbaI-Acc65I or NcoI-Acc65I fragment that contains the ccdB counter-selection module with the comparable fragment from any pAL vector (see, for example, FIGS. 3 and 4, and Tables 1-4). The pAL1 vector derived from pREX S31-tg10 has proved to be highly versatile for cloning and testing expression of a variety of coding sequences with or without a C-terminal 6His affinity tag. Anticipating that the somewhat lower basal and induced expression levels accessible with the Expression Control Regions of the S21-tg10 (SEQ ID NO. 63), LS31-tg10 (SEQ ID NO. 64) and LS21-tg10 (SEQ ID NO. 65) pREX vectors will be advantageous for some target proteins, the pAL2

(SEQ ID NO. 67), pAL3 (SEQ ID NO. 68) and pAL4 (SEQ ID NO. 69) vectors (Table 4) were derived from these pREX vectors by replacing the NcoI-Acc65I fragments of the pREX vectors with the comparable fragment of pAL1. Exchange of Translation Initiation Efficiency Regions or introduction of specific N- or C-terminal fusions into pAL vectors is easily done by taking advantage of the unique SacII, BsiWI, XbaI, NcoI, AgeI, EagI, and Acc65I sites in pAL vectors (Table 1 and FIG. 4).

Cloning and Co-Expressing More than One Coding Sequence in pAL Vectors

Ability to co-express more than one coding sequence from a single vector promises to be useful for producing functional protein complexes that contain more than one protein, especially when individual proteins are unstable or insoluble in the absence of their interacting partner(s).

Two or three coding sequences having appropriate overhangs can be directionally cloned routinely in a single asymmetric ligation reaction for co-expression in a pAL vector. Four coding sequences for co-expression and four fragments linked to make a single coding sequence have also been cloned in pAL1, but with some difficulty.

Coding sequences for T7 late proteins transcribed by T7 RNA polymerase during infection are translated efficiently from relatively stable mRNAs that contain several different coding sequences in tandem (Dunn et al. (1983) J. Mol. Biol. 166:477-535). The relative stability of T7 mRNAs is attributed primarily to stable stem-loop structures at their 3' ends, one of which is generated by termination at the Tphi transcription terminator in T7 DNA, which terminates transcription of target DNA in pAL vectors (and in pREX and many pET vectors). Each of the coding sequences in these multi-gene T7 mRNAs almost always has its own translation-initiation region with a strong SD sequence such as GGAG, GAGG or GGAGG separated from an ATG initiation codon by an AT-rich sequence ~5-9 nucleotides long containing few G residues. Therefore, sequences that link coding sequences for co-expression in pAL vectors have been designed to have these features.

To test cloning efficiency and co-expression as a function of length of the AT-rich region, coding sequences for the T7 gene 9 and 10a proteins were joined to each other through asymmetric overhangs of length 4 to 10 nucleotides containing only A and T residues and directionally cloned in single asymmetric ligation reactions for co-expression in pAL1. The (A,T) overhangs were designed to minimize complementary base pairs at or near the ends of all eight or more possible pairwise alignments outside of the three perfectly complementary alignments that produce the desired clone. Overhangs for joining the two coding sequences as well as overhangs for joining them to the pAL1 cloning-acceptor fragment were generated by treatment of the two PCR products with T4 DNA polymerase in the presence of dCTP. The sequences taaggagc (A, T)$_n$ and the complement of $_n$(A, T) gatg were joined by ligation to form the junction taaggagc$_n$(A, T)$_n$gatg, where the underlined taa is the termination codon of the first coding sequence, the underlined atg is the initiation codon of the second coding sequence, and $_n$(A, T)$_n$ represents the complementary asymmetric overhangs of different lengths at the 5' end of one PCR primer for amplifying each coding sequence (with the overhang for ligation to the cloning-acceptor fragment of pAL1 being generated at the other end). Each asymmetric ligation reaction produced hundreds of clones in XL1B, almost all of them correct, and auto-induction in BL21(DE3) produced comparable amounts of the two proteins in each of the seven clones. Therefore, a strategy of supplying a strong SD sequence joined to an ATG initiation codon through AT-rich overhangs between 4 and 10 nt long appears to work well for cloning and co-expression if nonproductive ligations are sufficiently minimized.

Cloning two or three coding sequences by asymmetric ligation for co-expression from pAL1 typically yields hundreds of colonies, almost all of which are correct. The usual junction between two coding sequences has been taaggagacTATTAATg (SEQ ID NO. 79), where the termination codon of the first coding sequence and the initiation codon of the second coding sequence are underlined. The 7-nt asymmetric sequence capitalized and its complement are the linker 5' overhangs generated by T4 DNA polymerase in the presence of dCTP from the PCR products to be joined. The junction between the second and third coding sequences has usually been taaggagacTTAATATg (SEQ ID NO. 80). The base-pairing patterns for all possible pairwise alignments of the overhangs present in cloning two or three coding sequences in pAL1 by asymmetric ligation using these overhangs are shown in FIGS. 6A-6B. The three or four ungapped, perfectly base- paired overhangs that can be efficiently ligated to produce the desired clone are represented as 1111, 1111111, and 1111 for cloning two coding sequences and 1111, 1111111, 1111111, and 1111 for cloning three coding sequences; and are circled in FIGS. 6A-6B. The 26 or 48 mismatched aligned pairs apparently are poor enough substrates for ligation that undesired ligation products do not significantly interfere with ability to obtain the desired clone.

To test possible position effects on expression levels, the T7 gene 8, 9, and 10a proteins were cloned for co-expression in pAL1 in all six possible gene orders, using the above two junction sequences. The three proteins in each of the gene orders were readily apparent in a stained gel after SDS-electrophoresis of whole-cell extracts of auto-induced cultures. In general, each protein was produced at a distinctly higher level when its coding sequence was in the first position to be transcribed relative to the second position, with perhaps a further slight decrease in the third position.

In attempts to extend simultaneous cloning by asymmetric ligation to four DNA fragments in pAL1, cloning efficiency was greatly reduced and only a small fraction of the clones were correct. This drastic reduction in success rate probably results from a combination of the increasing ratio of imperfectly to perfectly aligned overhangs and an unavoidable increase in lengths of perfectly paired bases at the ungapped ends of imperfectly aligned overhangs as the total number of overhangs increases. Nevertheless, one set of four coding sequences was cloned by asymmetric ligation for co-expression and another set of four DNA fragments was correctly linked to produce a single coding sequence for a multi-domain protein of 4832 amino acids. It may be possible to increase efficiency sufficiently to support routine cloning and co-expression of four or more coding sequences by using all four nucleotides in the overhangs that join coding sequences (for example, by using de novo synthesized DNAs) or by increasing the stringency of ligase for perfectly paired bases. Increasing the salt concentration to 200 mM or adding 5 mM spermidine to the ligation reaction mixture was reported by Wu et al. (1989) Gene 76:245-254 to increase the specificity of T4 ligase for perfectly-paired nicks relative to imperfectly paired sequences by 10-fold or more. Other ligases might also have greater specificity. These potential simple remedies have yet to be explored.

Variants of BL21(DE3) with Reduced Basal Expression

In the course of testing the ability of different pREX vectors to maintain and express clones of T7 gene 5.3 in BL21(DE3), several different 5.3 mutants were isolated from larger colonies that arose on plates used to titer populations stressed by basal expression. Analysis of large colonies from a set of plates that had mistakenly lacked the selective antibiotic found that a significant fraction had lost the plasmid, some retained expression clones having mutations that reduced expression or produced impaired 5.3 protein, and some retained apparently unaffected expression plasmid and therefore seemed likely to be variants of BL21(DE3) that could better tolerate 5.3 expression clones. Some white sectors of growth in colonies that were dying on LB plates because of unintended induction at saturation also gave rise to such variants. Potential variants of BL21(DE3) were readily isolated free of their expression plasmid simply by growing colonies on plates that lack the selective antibiotic and contain the inducer IPTG. Candidates were then tested for ability to support plaque formation by the T7 deletion mutant 4107, which lacks the entire gene for T7 RNA polymerase and cannot form a plaque unless active T7 RNA polymerase is provided by the host cell (Studier et al. (1986)). Plaque formation and size in the absence or presence of inducer are indicators of relative amounts of basal and induced T7 RNA polymerase supplied by the host cell. BL21(DE3) itself gave small plaques in the absence of inducer and large plaques in its presence. This plaque assay identified variants of BL21(DE3) that gave even smaller plaques or no detectable plaques in the absence of inducer and a range of plaque sizes in the presence of inducer, from no detectable plaques to large plaques comparable to those obtained with BL21(DE3) itself.

The upstream region controlling expression of T7 RNA polymerase from the chromosome of BL21(DE3) extends from the end of the lacI gene to the beginning of the coding sequence for T7 RNA polymerase (SEQ ID NO. 81) and contains: the L8 mutation, a G to A transition in the binding site for the cAMP receptor protein (CRP); the GT to AA double mutation that converts the −10 region of the lac promoter from the wild-type TATgtT to the stronger −10 consensus sequence TATAAT of the lacUV5 promoter; the lacO1 operator; the coding sequence for an N-terminal fragment of lacZ; and 26 base pairs of T7 DNA ahead of the ATG initiation codon for T7 RNA polymerase. The only sequence difference between E. coli K12, the source of this control region in BL21(DE3), and the same region of the lac operon in BL21(DE3) is the last base pair ahead of the minimal lacO1 operator (the sixth base pair downstream of the −10 sequence of the lac promoter), where K12 has a G and BL21(DE3) an A. It seemed likely that at least some of the BL21(DE3) variants would have changes in this upstream control region, in the coding sequence for T7 RNA polymerase, or both.

The entire sequence of the upstream control region between the end of lacI and the beginning of T7 RNA polymerase was sequenced in a set of 22 of the BL21(DE3) variants identified as large-colony variants that arose under stress by a 5.3 clone and categorized by T7 deletion mutant 4107 plaque test. The only sequence differences found in 15 of the 22 variants are conversion of the L8 and UV5 mutations to the wild-type sequence and conversion of the base pair ahead of lacO1 from the G of K12 to the A of BL21(DE3), a strong indication that these changes were due to gene conversion from the lac operon elsewhere in the BL21(DE3) genome. The same explanation holds for another 3 variants, which differ from these 15 only in retaining the L8 mutation in the CRP binding site, the same variant isolated and studied by Miroux et al. (1996) J. Mol. Biol. 260:289-298 and Schlegel et al. (2015) Cell Reports 10:17581766. The remaining 4 variants are identical to BL21(DE3) in this region. Three of these variants are the only ones that failed to show detectable plaques in the presence of inducer, and the fourth gave the smallest plaques observed in the presence of inducer, suggesting that these variants may have mutations in T7 RNA polymerase that decrease its activity or inactivate it.

The entire coding sequence for T7 RNA polymerase was determined for 8 of the 22 variants of BL21(DE3), selected to represent the types distinguishable by the combination of plaque assay and the sequence determined for the upstream control sequence. Four variants that increase the repertoire of useful T7 expression hosts are here referred to as BL21 (DE3)v1, v2, v3, and v4. The v1 variant (SEQ ID NO. 82) has a detectable but reduced level of basal expression relative to BL21(DE3) but retains full induced expression, as indicated by plaque size in the absence and presence of inducer and by the levels of T7 10a protein produced from a pREX LS31 clone by auto-induction. This variant is representative of 13 of the 15 variants that converted the upstream control region to the wild-type lac promoter. It has no changes in the T7 RNA polymerase sequence. The v2 variant (SEQ ID NO. 83) has no basal expression detectable by the plaque assay and a somewhat lower induced expression relative to BL21(DE3), as indicated by a somewhat smaller plaque size in the presence of inducer and lower 10a expression levels by auto-induction. This variant is representative of the 3 variants that converted all but the L8 mutation in the CRP binding site in the upstream control region to wild type. It likewise has no changes in the T7 RNA polymerase sequence. The v3 variant (SEQ ID NO. 84) has no basal activity detectable by the plaque assay and an induced activity comparable to that of v2. Sequencing found that this variant is identical to v1 in the upstream control region but has acquired a mutation of alanine-102 of T7 RNA polymerase to threonine. Another of the 8 fully sequenced variants is identical to this one. The v4 variant (SEQ ID NO. 85) has no basal activity detectable by the plaque assay and a somewhat lower induced activity than v2 and v3. This variant is identical to BL21(DE3) in the upstream control region and has acquired a mutation of proline-818 of T7 RNA polymerase to glutamine. The relative activity of the alanine-102 and proline-818 mutant RNA polymerases is difficult to assess from these results, because v3 should have a higher level of induced expression than v4. The 3 remaining sequence variants have no basal or induced activity detectable by the plaque assay: two of them have an amber termination mutation at glutamine-36 and the third has an 8-bp duplication at leucine-706, which changes the reading frame.

Variants that reduce basal expression of target protein increase the range of target proteins that can be stably maintained and produced in inducible T7 expression strains. Hosts that supply mutant but functional T7 RNA polymerases, such as the two isolated here or others that could be isolated and characterized by the methods disclosed here, may have unique advantages for adjusting rates of transcription to enhance the production of properly folded or secreted and functional target proteins.

The present disclosure contemplates T7 expression strains that contain the coding sequence for T7 RNA polymerase discussed above. Examples of T7 expression strains include BL21 CodonPlus and Lemo21(DE3).

General Methods for Cloning into pAL Vectors

Commonly used growth media can be suitable for growing *E. coli* hosts for cloning, transformation, preparation of freezer stocks, isolation of plasmids and maintenance of clones for expressing most target proteins in pREX and pAL vectors. However, variability in complex components in most media can cause unintended induction and instability (Studier, 2005). To avoid or minimize such problems, fully defined growth media made entirely from purified components are used routinely (Studier (2014) *Methods in Molecular Biology* (Clifton, N.J.) 1091:17-32; and Studier, U.S. Pat. Nos. 8,241,887 and 7,704,722). For induction of expression, the auto-induction media and methods of Studier (2014) and Studier, U.S. Pat. Nos. 7,560,264; 7,759,109; and 8,399,217 are useful, the contents of which are incorporated herein by reference.

Studier (2014) describes non-inducing growth media MDAG-135+B1 (B1=1 μM thiamine) and MDAG-11+B 1. MDAG-135+B1 is suitable for growth to high density of well-aerated cultures of DB3.1, XL1B, BL21 and strains derived from BL21, such as BL21(DE3) and BL21-AI. Kanamycin at a concentration of 100 μg/ml is routinely used for selection and maintenance of pREX and pAL clones in these media, where little if any unintended induction should occur. Indeed, no target protein has been found to be so toxic to the host that an expressible gene could not readily be cloned in an appropriate pREX or pAL vector in XL1B and transferred to BL21(DE3) and BL21-AI in these media. Even strains showing signs of stress could often be grown to high density with good yields of plasmid. MDAG-135+B1 is also good for preparation of chemically competent DB3.1 for transformation (currently not commercially available).

MDAG-11+B1 has a lower concentration of glucose, which limits acid production at saturation in less well aerated conditions. This medium (plus selective antibiotic) is suitable for selection of transformants on 1% agar plates, and colonies typically remain viable on these plates for weeks in the refrigerator. Plates can be stored refrigerated before use but should be well equilibrated to room temperature for several hours before placing in a 37° C. incubator, to prevent formation of small air bubbles in the agar. This medium is also used for 0.7% agar stabs for mailing cultures or for poorly aerated or standing cultures.

Freezer stocks for long-term storage are made by mixing 1 ml of culture with 0.1 ml of 80% glycerol in a 2-ml plastic freezer tube and placing directly in a −70° C. freezer. Cultures of most clones are grown to saturation before freezing but should not be allowed to grow beyond mid-log phase before freezing if the clone is highly toxic to the host. Cultures are inoculated from freezer stocks by scraping some frozen culture from the surface without thawing the rest of the tube.

Standard procedures are used for isolating plasmids, high-fidelity PCR amplifications of DNA, enzyme treatments, purification of amplified or enzymatically treated DNA and transformation of chemically competent cells. Quality and concentration of purified DNA are routinely determined by Nanodrop Spectrometry and agarose gel electrophoresis. Typical commercial products include: Wizard Plus SV Miniprep DNA Purification System for purifying plasmids (Promega); Accuprime Pfx SuperMix for high-fidelity PCR (Invitrogen/Life Technologies); synthetic DNA primers (Integrated DNA Technologies); illustra GFX PCR DNA and Gel Band Purification Kit (GE Healthcare Life Sciences); DNA Clean & Concentrator-5 Kit (Zymogen); BsaI-HF, other restriction enzymes, T4 DNA polymerase, T4 ligase, T4 polynucleotide kinase, NTPs, dNTPs and reaction buffers (New England Biolabs); XL1B-MR Chemically Competent cells (Agilent); BL21(DE3) Chemically Competent cells (Novagen); and BL21-AI Chemically Competent cells (Invitrogen/Life Technologies). In a five-minute reaction at room temperature, purified PCR product (or blunt-end synthetic DNA) is treated with T4 DNA polymerase in the presence of the appropriate dNTP to generate the overhangs for cloning into pAL vectors and, in the same reaction mixture, with T4 Polynucleotide Kinase and ATP to phosphorylate the 5' ends of the overhangs. For convenience, the reaction volume is usually 50 μl and contains ~10 nM DNA, 0.2 mM dNTP, 1 unit of T4 DNA polymerase, 1 unit of T4 polynucleotide kinase and BSA at a concentration of 100 μg/ml in New England Biolabs T4 DNA Ligase Reaction Buffer (50 mM Tris-HCl, 10 mM $MgCl_2$, 10 mM DTT, 1 mM ATP, pH 7.8). The reaction has also been scaled to 20 μl volume when the amount of synthetic DNA was limiting. The reaction is stopped by adding 3 μl of 0.5 M EDTA per 50 μl of reaction mixture and the treated DNA is purified by the GFX process, eluting the microspin column with a volume of low TE (1 mM Tris, 0.1 mM EDTA, pH 8) equal to the reaction volume.

Purified pAL plasmid is digested with BsaI-HF, which is then heat-inactivated for 20 minutes at 65° C. The cut DNA is ethanol-precipitated for at least 1 hour at −70° C., washed, dried and dissolved in low TE. This DNA can be used immediately for cloning but, for convenience, we usually make a larger batch, analyze a sample by agarose gel electrophoresis to verify BsaI cutting and nanodrop concentration, and store aliquots at −20° C. for future cloning. In limited testing, purification of the acceptor fragment seemed to offer little if any advantage.

In another five-minute reaction at room temperature, the DNA to be cloned, whether overhangs were generated by T4 DNA polymerase or in the design of synthetic DNA, is ligated to the BsaI-cut pAL vector. A reaction volume of 20 μl contains 1 nM concentration each of the cut vector and the DNA to be cloned and 400 units of T4 DNA ligase in New England Biolabs T4 DNA Ligase Reaction Buffer (50 mM Tris-HCl, 10 mM $MgCl_2$, 10 mM DTT, 1 mM ATP, pH 7.8). Typically, 1 μl of the reaction mixture is used immediately for transformation of 25 μl of chemically competent cells and the remainder is stored at −20° C. for further use, if needed.

Definitions

As used herein, a "host cell" includes any cell capable of proliferating the DNA vectors disclosed herein. In one embodiment, the host cell is a prokaryotic cell. Examples of suitable host cells include BL21 (DE3) and derivatives thereof.

As used herein, "prokaryote" and "prokaryotic cell" refer to cells which do not contain a nucleus and whose chromosomal material is thus not separated from the cytoplasm. Prokaryotes include, for example, bacteria. Prokaryotic host cells particularly embraced by the present invention include those amenable to genetic manipulation and growth in culture. Exemplary prokaryotes routinely used in recombinant protein expression include, but are not limited to, *E. coli*, *Bacillus licheniformis* (van Leen, et al. (1991) Bio/

Technology 9:47-52), *Ralstonia eutropha* (Srinivasan, et al. (2002) Appl. Environ. Microbiol. 68:5925-5932), *Methylobacterium extorquens* (Belanger, et al. (2004) FEMS Microbiol Lett. 231(2):197-204), *Lactococcus lactis* (Oddone, et al. (2009) Plasmid 62(2):108-18) and *Pseudomonas* sp. (e.g., *P. aerugenosa, P. fluorescens* and *P. syringae*). Prokaryotic host cells can be obtained from commercial sources (e.g., Clontech, Invitrogen, Stratagene and the like) or repositories such as American Type Culture Collection (Manassas, Va.). In particular embodiments, the prokaryotic host cell is *E. coli*.

As used herein, a "vector" is a DNA molecule to which heterologous DNA may be operatively linked so as to bring about replication of the heterologous DNA. Vectors are conventionally used to deliver DNA molecules to cells, including *E. coli* cells that are typically used in a majority of cloning or protein expression applications. Examples of vectors include plasmid, cosmid, and phages.

Type II restriction endonucleases are enzymes that cleave DNA at different positions close to or within their recognition sequences. Examples include XbaI, NcoI, and NotI.

Type IIS restriction endonucleases are enzymes that cleave DNA outside of their recognition sequences, to one side. Examples of type IIS restriction endonucleases include FokI, AlwI, and BsaI.

As used herein, a "target DNA" includes a polynucleotide. The term "polynucleotide" as used herein is defined as a chain of nucleotides. Polynucleotide includes DNA and RNA.

Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can be included in a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, and fusion proteins, among others. The polypeptides include natural peptides, recombinant peptides, synthetic peptides, or a combination thereof.

A "heterologous" peptide or polypeptide means a peptide or polypeptide encoded by a non-host DNA molecule. The heterologous peptide or polypeptide may be toxic to the host cell when expressed by way of an expression vector.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

While there have been described what are presently believed to be the preferred embodiments of the present invention, those skilled in the art will realize that other and further changes and modifications may be made thereto without departing from the spirit of the invention, and it is intended to claim all such modifications and changes as come within the true scope of the invention.

TABLE 1

Sequences of Expression control Region (ECR) in T7 DNA; pET, pREX, pAL vectors; ZA#11, ZA#13 in US 6,537,779

| SEQ ID NO. | | | Expression Control Region (ECR) | | | | | | |
|---|---|---|---|---|---|---|---|---|---|
| | | | T7 promoter | T7 RNA start and palindrome | | | | XbaI | tg10 | ndeI |
| 8 | T7 DNA | | ACTTCG AAAT TAATACGACTCACTATA GGGAGACC ACAAC GGTTTCCCC | | | | TCTAGA AATAATTTGTTTAACTTTAAGAAGGAGATATACATATG |
| 9 | pBT-3a | | cccgCG AAAT TAATACGACTCACTATA GGGAGACC ACAAC GGTTTCCCC | | | | TCTAGA AATAATTTGTTTAACTTTAAGAAGGAGATATACATATG |
| | | | | | RNA | lacO1 palindrome | link | | | |
| 10 | pET-11d | | cccgCG AAAT TAATACGACTCACTATA GGGG AATTGTGAGCGGATAACAATT CCCC | | | | TCTAGA AATAATTTGTTTAACTTTAAGAAGGAAGTATACATATG |
| 11 | ZA#11 | | attcCG AAAT TAATACGACTCACTATA GGGG AATTGTGAGCGGATAACAATT CCCC | | | | TCTAGA AATAATTTGTTTAACTTTAAGAAGGAAGTATACATATG |
| | | | | | | lacS palindrome | | | | |
| 12 | ZA#13 | | attcCG AAAT TAATACGACTCACTATA GGGG AATTGTGAGCGCTCACAATT CCCC | | | | TCTAGA AATAATTTGTTTAACTTTAAGAAGGAGTATACATATG |
| | pREX | | attcCG AAAT TAATACGACTCACTATA GGGG AATTGTGAGCGCTCACAATT CCCC | | | | TCTAGA AATAATTTGTTTAACTTTAAGAAGGAGTATACATATG |
| | | | T7 Promoter Control Region (TPCR) | | | | Translation Initiation Efficiency Region (TIER) |
| | | | T7 promoter | | RNA | lacO1 palindrome | link | XbaI | tg10, SEQ ID NO: 48 | NcoI |
| 13 | TPCR | EsiWI | cgtacg AAAT TAATACGACTCACTATA GGGG AATTGTGAGC GCTCACAATT CCCC | | | | TCTAGA AATAATTTGTTTAACTTTAAGAAGGAGATATAC CATG |
| 14 | L44 | | cgtacg AAAT TAATACGACTCACTATA GGG AATTGTGAGC GCTCACAATT CCC | | | | TCTAGA AATAATTTGTTTAACTTTAAGAAGGAGATATAC CATG |
| 15 | L33 | | cgtacg AAAT TAATACGACTCACTATA GG AATTGTGAGC GCTCACAATT CC | | | | TCTAGA AATAATTTGTTTAACTTTAAGAAGGAGATATAC CATG |
| 16 | L22 | | cgtacg AAAT TAATACGACTCACTATA GG AATTGTGAGC GCTCACAATT C | | | | TCTAGA AATAATTTGTTTAACTTTAAGAAGGAGATATAC CATG |
| | L1m | | cgtacg AAAT TAATACGACTCACTATA G AATTGTGAGC GCTCACAATT | | | | TCTAGA AATAATTTGTTTAACTTTAAGAAGGAGATATAC CATG |
| | | | | | | lacS palindrome | | | | |
| 20 | S34 | | cgtacg AAAT TAATACGACTCACTATA GGGG AATTGTGAGC GCTCACAATT CCCC | | | | TCTAGA AATAATTTGTTTAACTTTAAGAAGGAGATATAC CATG |
| 21 | S33 | | cgtacg AAAT TAATACGACTCACTATA GGG AATTGTGAGC GCTCACAATT CCC | | | | TCTAGA AATAATTTGTTTAACTTTAAGAAGGAGATATAC CATG |
| 22 | S32 | | cgtacg AAAT TAATACGACTCACTATA GGG AATTGTGAGC GCTCACAATT CC | | | | TCTAGA AATAATTTGTTTAACTTTAAGAAGGAGATATAC CATG |
| 23 | S31 | pAL1 | cgtacg AAAT TAATACGACTCACTATA GGG AATTGTGAGC GCTCACAATT C | | | | TCTAGA AATAATTTGTTTAACTTTAAGAAGGAGATATAC CATG |
| 24 | S30 | | cgtacg AAAT TAATACGACTCACTATA GGG AATTGTGAGC GCTCACAATT | | | | TCTAGA AATAATTTGTTTAACTTTAAGAAGGAGATATAC CATG |
| 25 | S3m | | cgtacg AAAT TAATACGACTCACTATA GGG AATTGTGAGC GCTCACAATT | | | | CTAGA AATAATTTGTTTAACTTTAAGAAGGAGATATAC CATG |
| 26 | S24 | | cgtacg AAAT TAATACGACTCACTATA GG AATTGTGAGC GCTCACAATT CCCC | | | | TCTAGA AATAATTTGTTTAACTTTAAGAAGGAGATATAC CATG |
| 27 | S23 | | cgtacg AAAT TAATACGACTCACTATA GG AATTGTGAGC GCTCACAATT CCC | | | | TCTAGA AATAATTTGTTTAACTTTAAGAAGGAGATATAC CATG |
| 28 | S22 | | cgtacg AAAT TAATACGACTCACTATA GG AATTGTGAGC GCTCACAATT CC | | | | TCTAGA AATAATTTGTTTAACTTTAAGAAGGAGATATAC CATG |
| 29 | S21 | pAL2 | cgtacg AAAT TAATACGACTCACTATA GG AATTGTGAGC GCTCACAATT C | | | | TCTAGA AATAATTTGTTTAACTTTAAGAAGGAGATATAC CATG |
| 30 | S20 | | cgtacg AAAT TAATACGACTCACTATA GG AATTGTGAGC GCTCACAATT | | | | TCTAGA AATAATTTGTTTAACTTTAAGAAGGAGATATAC CATG |
| 31 | S2m | | cgtacg AAAT TAATACGACTCACTATA GG AATTGTGAGC GCTCACAATT | | | | CTAGA AATAATTTGTTTAACTTTAAGAAGGAGATATAC CATG |
| 32 | S1m | | cgtacg AAAT TAATACGACTCACTATA G AATTGTGAGC GCTCACAATT | | | | CTAGA AATAATTTGTTTAACTTTAAGAAGGAGATATAC CATG |

TABLE 1-continued

Sequences of Expression control Region (ECR) in T7 DNA: pET, pREX, pAL vectors; ZA#11, ZA#13 in US 6,537,779

Upstream 37-bp lacO1 with extended natural palindrome (and spacer sequence) in pREX-Ls vectors, pAL3 and pAL4

| SEQ ID NO. | SacII | lacO1 | spacer | BsiWI | T7 promoter | RNA |
|---|---|---|---|---|---|---|
| 86 | CGTA CCGCGG | TTGTGTGG AATTGTGAGCGGATAACAATT TCACACAG | AAACAGCTCCCT | cgtaCG | AAAT TAATACGACTCACTATA | GG |

Bases in the 37-bp extended natural palindrome of lacO1 are underlined
lacO1 operators are in the same orientation as in the lac operon and in pET vectors
Center-to-center spacing between the lacO1 operators is 70.5 bp in pAL3 and pREX-LS3 vectors and is 69.5 bp in pAL4 and pREX-LS2 vectors

TABLE 2

Deletions and sequence changes between the Thai site and Shine-Dalgarno (SD) sequence of the tg10 Translation Initiation Efficiency Region (TIER) affect ability to clone T7 gene 5.3 and to produce T7 gene 10a protein in pREX L44.

| | | | Translation Initiation Efficiency Region (TIER) | | | | T7 lac-5.3 transformants | | | T7 lac-10a BL21 (DE3) |
|---|---|---|---|---|---|---|---|---|---|---|
| SEQ ID NO. | TIER | XbaI <SD bp | XbaI site | Shine-Dalgarno sequence | | Start codon | XL1B | BL21 (DE3) | BL21 A1 | induced protein |
| 48 | tg10 | 28 | TCTAGA | AAT<u>AATTTT</u>GTT<u>TAACTTT</u>AAG | AAGGAG ATATACC | ATG | 0 | 0 | 0 | +++ |
| 49 | tr4 | 24 | TCTAGA AAT | TTC TT<u>TAACTTT</u>AAG | AAGGAG ATATACC | ATG | sm | (tiny) | + | +++ |
| 50 | tr11 | 16 | TCTAGA | <u>TAACTTT</u>AAG | AAGGAG ATATACC | ATG | + | (tiny) | + | +++ |
| 51 | tr10 | 15 | TCTAGA | AACTTTAAG | AAGGAG ATATACC | ATG | | | | +++ |
| 52 | tr9 | 14 | TCTAG | AACTTTAAG | AAGGAG ATATACC | ATG | + | (tiny) | + | (+++) |
| 53 | tr8 | 14 | TCTAGA AA | TTTAAG | AAGGAG ATATACC | ATG | + | (sm) | + | (+++) |
| 54 | tr2 | 13 | TCT<u>AG</u> | <u>AC</u>TTTAAG | AAGGAG ATATACC | ATG | + | sm | + | ++ |
| 55 | tr7 | 12 | TCTAGA AA | TAAG | AAGGAG ATATACC | ATG | + | tiny | + | (++) |
| 56 | tr6 | 10 | TCTAGA | TAAG | AAGGAG ATATACC | ATG | + | tiny | + | + |
| 57 | tr5 | 8 | TCTAG | AAG | AAGGAG ATATACC | ATG | + | sm | + | + |
| 58 | tr1 | 5 | TCT | AG | AAGGAG ATATACC | ATG | + | med | + | (+) |
| 59 | tr3 | 12 | TCTAGA | AGACTA | CATGTG GTCTCCC | ATG | + | + | + | 0? |

XbaI→SD column gives the number of base pairs ahead of the Shine-Dalgarno (SD) sequence in the Translation Initiation Efficiency Region (or a comparable number for tr3, which has no obvious SD sequence)
Potential -10 sequences for *E. coli* promoters (TAtaaT) are underlined.
A potential -10 sequence (TAGACT) created by deletion in tr2 appears to have little effect on basal expression in pREX L44-tr2, as judged by ability to clone and maintain gene 5.3 in XL1B and BL21(DE3)

TABLE 3

Ability to clone and express T7 5.3 and 10a coding sequences in different pREX vectors

| | | | Configuration of Expression Control Region (ECR) | | | | | 5.3 clones in pREX transformed colonies | | | 10a clones Protein level | |
|---|---|---|---|---|---|---|---|---|---|---|---|---|
| SEQ ID NO. | pREX | TPCR | downstream of T7 promoter sequence | | | | TIER SEQ #48 | | | | | |
| | | | RNA start | lac operator | | Linker | XbaI | tg10 | XL1B | DE3 | A1 | DE3 | A1 |
| 13 | L44 | | GGGG | AATT | O1 | AATT | CCCC | TCTAGA | tg10 | 0 | 0 | 0 | +++ | +++ |
| 14 | L33 | | GGG | AATT | O1 | AATT | CCC | TCTAGA | tg10 | tn + sm | 0 | 0 | +++ | +++ |
| 15 | L22 | | GG | AATT | O1 | AATT | CC | TCTAGA | tg10 | sm | 0 | str | +++ | ++ |
| 16 | L1m | | G | AATT | O1 | AATT | | CTAGA | tg10 | sm | 0 | sm | ? | (+) |
| 20 | S34 | | GGG | AATT | S | AATT | CCCC | TCTAGA | tg10 | 0 | 0 | 0 | +++ | +++ |
| 21 | S33 | | GGG | AATT | S | AATT | CCC | TCTAGA | tg10 | md + tn | 0 | 0 | +++ | (+++) |
| 22 | S32 | | GGG | AATT | S | AATT | CC | TCTAGA | tg10 | mlg + tn | sm | mlg | +++ | (+++) |
| 23 | S31 | pAL1 | GGG | AATT | S | AATT | C | TCTAGA | tg10 | (lg) | sm | mlg | +++ | (+++) |
| 24 | S30 | | GGG | AATT | S | AATT | | TCTAGA | tg10 | mlg | sm | mlg | +++ | (+++) |
| 25 | S3m | | GGG | AATT | S | AATT | | CTAGA | tg10 | mlg | sm | mlg | +++ | (+++) |
| 26 | S24 | | GG | AATT | S | AATT | CCCC | TCTAGA | tg10 | 0 | 0 | 0 | +++ | ++ |
| 27 | S23 | | GG | AATT | S | AATT | CCC | TCTAGA | tg10 | tn + md | 0 | 0 | +++ | ++ |
| 28 | S22 | | GG | AATT | S | AATT | CC | TCTAGA | tg10 | mlg + tn | sm | mlg | +++ | ++ |
| 29 | S21 | pAL2 | GG | AATT | S | AATT | C | TCTAGA | tg10 | mlg | smd | mlg | +++ | ++ |

TABLE 3-continued

Ability to clone and express T7 5.3 and 10a coding sequences in different pREX vectors

| SEQ ID NO. | pREX TPCR | | RNA start | Configuration of Expression Control Region (ECR) downstream of T7 promoter sequence | | | | TIER SEQ #48 | 5.3 clones in pREX transformed colonies | | | 10a clones Protein level | |
|---|---|---|---|---|---|---|---|---|---|---|---|---|---|
| | | | | lac operator | | Linker | XbaI | | XL1B | DE3 | Al | DE3 | Al |
| 30 | S20 | | GG | AATT | S | AATT | | TCTAGA | tg10 | mlg | smd | mlg | +++ | ++ |
| 31 | S2m | | GG | AATT | S | AATT | | CTAGA | tg10 | mlg | smd | mlg | +++ | +++ |
| 32 | S1m | | G | AATT | S | AATT | | CTAGA | tg10 | smd | med | mlg | (+) | + |
| 36 | LS34 | | GGG | AATT | S | AATT | CCCC | TCTAGA | tg10 | 0 | 0 | 0 | +++ | ++ |
| 37 | LS33 | | GGG | AATT | S | AATT | CCC | TCTAGA | tg10 | lg | 0 | str | (+++) | ++ |
| 38 | LS32 | | GGG | AATT | S | AATT | CC | TCTAGA | tg10 | lg | mlg | lg | +++ | ++ |
| 39 | LS31 | pAL3 | GGG | AATT | S | AATT | C | TCTAGA | tg10 | lg | mlg | lg | +++ | (++) |
| 40 | LS30 | | GGG | AATT | S | AATT | | TCTAGA | tg10 | lg | mlg | lg | +++ | (++) |
| 41 | LS3m | | GGG | AATT | S | AATT | | CTAGA | tg10 | lg | mix | lg | +++ | + |
| 42 | L24 | | GG | AATT | S | AATT | CCCC | TCTAGA | tg10 | 0 | 0 | 0 | (+++) | + |
| 43 | LS23 | | GG | AATT | S | AATT | CCC | TCTAGA | tg10 | mlg | 0 | str | +++ | + |
| 44 | LS22 | | GG | AATT | S | AATT | CC | TCTAGA | tg10 | lg | mlg | lg | (+++) | + |
| 45 | LS21 | pAL4 | GG | AATT | S | AATT | C | TCTAGA | tg10 | lg | mlg | lg | +++ | + |
| 46 | LS20 | | GG | AATT | S | AATT | | TCTAGA | tg10 | lg | mlg | lg | +++ | + |
| 47 | LS2m | | GG | AATT | S | AATT | | CTAGA | tg10 | lg | mlg | lg | +++ | + |

T7 Promoter Control Region (TPCR) designations for pREX and pAL vectors (full spectrum in Table 1)
L indicates a minimal 21-bp lacO1 asymmetric operator downstream of the T7 promoter sequence
S indicates an extended 37-bp lacS symmetric operator downstream of the T7 promoter sequence
LS indicates an extended 37-bp lacO1 operator downstream and a 20-bp lacS operator downstream of the T7 promoter sequence, separated by 69.5 aor 70.5 bp center-to-center for maximum repression
Assymmetric lacO1 operators have the same orientation as in the lac operon and in pET vectors
The second integer gives the number of C residues linking the downstream operator to the XbaI site
An "m" indicates that the T of the downstream operator is also the first T of the XbaI site
Transiation Initiation Efficiecny Region (TIER) is tg10 in all vectors in the table (effects of other TIER seqs in Table 2)
pREX vectors are identified unambiguously by a TPCR-TIER compound name; if TPCR only is given, the TIER is tg10
Attempts to maintain pREX clones of T7 gene in the hosts XL1B, BL21(DE3), and BL21-Al are summarized:
0 did not obtain transformants with active 5.3
str cultures obviously stressed, susceptible to overgrowth by mutants
tn some or most clones were inactivated by tn10 instertion in SL1B
sm small or late-developing colonies
smd small-medium colonies
med medium colonies
mlg medium-large colonies
lg large colonies
mix miture of colonies of different sizes

TABLE 4

Configurations flanking the cloning sites of different pAL vectors, and sequences at ends of PCR products for generating 4-nt 5' overhangs for ligation to pAL cloning acceptors

| SEQ ID# | Vector | ECR | N-terminal fusion | Cloning site and counter-selection module Optional C-terminal fusions | Blunt ends of PCR for 4-nt 5' overhangs upstream-downstream |
|---|---|---|---|---|---|
| | | | | | T7 DNAP + dCTP |
| 66 | pAL1 | S31-tg10 | -NcoI | -BsaI-AgeI-ccdB-EagI-BsaI-NNC-Ser-Gly-6His-Acc65I | 5' CCATG-NNCAGTG 3' |
| 67 | pAL2 | S21-tg10 | -NcoI | -BsaI-AgeI-ccdB-EagI-BsaI-NNC-Ser-Gly-6His-Acc65I | 5' CCATG-NNCAGTG 3' |
| 68 | pAL3 | LS21-tg10 | -NcoI | -BsaI-AgeI-ccdB-EagI-BsaI-NNC-Ser-Gly-6His-Acc65I | 5' CCATG-NNCAGTG 3' |
| 69 | pAL4 | LS21-tg0 | -NcoI | -BsaI-AgeI-ccdB-EagI-BsaI-NNC-Ser-Gly-6His-Acc65I | 5' CCATG-NNCAGTG 3' |
| 70 | pAL5 | S31-tg5 | -NcoI | -BsaI-AgeI-ccdB-EagI-BsaI-NNC-Ser-Gly-6His-Acc65I | 5' CCATG-NNCAGTG 3' |
| 71 | pAL11 | S31-tg10 | -NcoI | -BsaI-AgeI-ccdB-EagI-BsaI-NNC-Ser-dsbC(21-93)-BamHI-6His-Acc65I | 5' CCATG-NNCAGTG 3' |
| 72 | pAL12 | S31-tr5 | -NcoI | -BsaI-AgeI-ccdB-EagI-BsaI-NNC-Ser-dsbC(21-93)-BamHI-6His-Acc65I | 5' CCATG-NNCAGTG 3' |
| 73 | pAL13 | S31-tg10 | -NdeI-NheI-6His | -BsaI-AgeI-ccdB-EagI-BsaI-NNC-Ser-dsbC(21-93)-BamHI-TAA-Acc65I | 5' ACTCG-NNCAGTG 3' |
| 74 | pAL14 | S31-tr5 | -NdeI-NheI-6His | -BsaI-AgeI-ccdB-EagI-BsaI-NNC-Ser-dsbC(21-93)-BamHI-TAA-Acc65I | 5' ACTCG-NNCAGTG 3' |
| | | | | | T4 DNAP + dTTP |
| 75 | pAL21 | S31-tg10 | -NdeI-pelB | -BsaI-AgeI-ccdB-EagI-BsaI-NNC-Ser-dsbC(21-93)-BamHI-6His-Acc65I | 5' CTGCA-NNTAGCG 3' |
| 76 | pAL22 | S31-tr5 | -NdeI-pelB | -BsaI-AgeI-ccdB-EagI-BsaI-NNC-Ser-dsbC(21-93)-BamHI-6His-Acc65I | 5' CTGCA-NNTAGCG 3' |
| 77 | pAL23 | S31-tg10 | -NdeI-dsbA | -BsaI-AgeI-ccdB-EagI-BsaI-NNC-Ser-dsbC(21-93)-BamHI-6His-Acc65I | 5' CTGCA-NNTAGCG 3' |
| 78 | pAL24 | S31-tr5 | -NdeI-dsbA | -BsaI-AgeI-ccdB-EagI-BsaI-NNC-Ser-dsbC(21-93)-BamHI-6His-Acc65I | 5' CTGCA-NNTAGCG 3' |

The outward facing BsaI sites for cloning are underlined, as are the codons in the PCR primers that will fuse the target coding sequence in the correct reading frame for N- or C-terminal fusions.
C-terminal fusions are optional. To terminate a coding sequence without a C-terminal fusion, the termination codon (default TAA) is places ahead of the 5-bp C-terminal fusion sequence in the PCR primer.
C-terminal fusions represented in these vectors include 6His affinity tags and the dimerization domain of dsbC. N-terminal fusions include 6His affinity tags, the N-terminal pelB leader sequence, which directs secretion into the periplasm by the Sec pathway, and the N-terminal dsbA leader sequence, which directs into the periplasm by the SRP pathway.
Achieving optimal secretion and/or folding of target protein may require matching the rate of target protein production to the secretion and/or folding capacity of the cell. Basal and induced expression will be higher with the tg10 upstream translation sequence than the tr5 and will be generally higher in BL21(DE3) than in BL21-AI. Other rates of target protein production could be achieved with other vector-host configurations.

INCORPORATION OF SEQUENCE LISTING

A Sequence Listing conforming to the rules of WIPO Standard ST.25 is hereby incorporated by reference. Said Sequence Listing has been filed as an electronic document via PatentCenter in ASCII text. The electronic document, created on Feb. 16, 2023, is entitled "IP2014-019-03-_PCT-US_ST25.txt", and is 147,312 bytes in size.

The invention claimed is:

1. A vector comprising:
    a T7 Promoter Control Region polynucleotide selected from the group consisting of: SEQ ID NO: 17, 18, 19, 23, 24, 25, 29, 30, 31, 32, 33, 34, 35, 38, 39, 40, 41, 44, 45, 46, 47, 94, 95, 96, 97, 98, 99, 100, 101, and 102; and
    a Translation Initiation Efficiency Region polynucleotide selected from the group consisting of SEQ ID NO: 48, 49, 50, 51, 52, 53, 54, 55, 56, 57, 58, 87, 88, 89, 90, 91, 92, and 93;
    wherein,
        the T7 Promoter Control Region polynucleotide is joined at the 3' end to the 5' end of the Translation Initiation Efficiency Region polynucleotide; and
        a spacer comprising between 0, 1, or 2 nucleotide residues is disposed between the T7 Promoter Control Region polynucleotide and the Translation Initiation Efficiency Region polynucleotide.

2. The vector of claim 1 wherein said vector comprises at least one of:
    a site for directional cloning of a target coding sequence by ligation to an acceptor overhang that is complementary to an upstream overhang 5'- CATG sequence and ligation to a downstream acceptor overhang comprising TA-3' or TG-3';
    a cloning-acceptor fragment wherein all transcribed elements except the primer for DNA replication are in an orientation opposite to that of the target coding sequence; and
    a DNA sequence between said upstream and downstream acceptor overhangs of said site for directional cloning comprises a counter-selection module.

3. The vector of claim 1 wherein said vector comprises at least one of: a lacIt enhanced translation start (SEQ ID NO: 61); and
    a sequence for constitutive expression of the ccdB toxin of E. coli F factor (SEQ ID NO: 2).

4. A vector for directional cloning of at least one target DNA by asymmetric ligation comprising:
    a cloning site with upstream and downstream outward-facing asymmetric recognition sequences for at least one Type IIS restriction endonuclease, said recognition sequences being situated such that cutting said vector with said at least one Type IIS endonuclease produces two vector fragments:
        1) a cloning-acceptor fragment having a different asymmetric overhang at each end; and
        2) a counter-selection fragment containing both of said outward-facing recognition sequences and having asymmetric overhangs complementary to those of said cloning-acceptor fragment; and
    wherein the nucleotide sequences of said 4 asymmetric overhangs are designed so that only 2 of the 10 possible pairwise alignments between said overhangs form ungapped perfectly base-paired substrates for a DNA ligase to join either strand, thereby regenerating said vector, and additionally so that the number of consecutive perfect base-pairs from either ungapped end of each of the remaining 8 said possible pairwise alignments is minimized, thereby minimizing potential joining of either DNA strand at any of said remaining 8 possible pairwise aligned overhangs by said DNA ligase.

5. The vector of claim 4 comprising at least one of:
    an Expression Control Region polynucleotide positioned in said cloning-acceptor fragment so as to direct expression of at least one coding sequence in said directionally cloned at least one target DNA, wherein the Expression Control Region polynucleotide comprises:
    a T7 Promoter Control Region polynucleotide selected from the group consisting of: SEQ ID NO: 17, 18, 19, 23, 24, 25, 29, 30, 31, 32, 33, 34, 35, 38, 39, 40, 41, 44, 45, 46, 47, 94, 95, 96, 97, 98, 99, 100, 101, and 102; and
    a Translation Initiation Efficiency Region polynucleotide selected from the group consisting of SEQ ID NO: 48, 49, 50, 51, 52, 53, 54, 55, 56, 57, 58, 87, 88, 89, 90, 91, 92, and 93; wherein,
        the T7 Promoter Control Region polynucleotide is joined at the 3' end to the 5' end of the Translation Initiation Efficiency Region polynucleotide; and
    a cloning-acceptor fragment wherein all transcribed elements except the primer for DNA replication are in an orientation opposite to that of the target coding sequence.

6. The cloning and expression vector of claim 5 comprising at least one of:
    a lacIt enhanced translation start (SEQ ID NO: 61); and
    counter-selection fragment comprising a sequence for constitutive expression of the ccdB toxin of E. coli F factor (SEQ ID NO: 2).

7. The vector of claim 6 wherein said upstream and downstream outward-facing recognition sequences comprise BsaI recognition sequence and wherein cutting by BsaI produces two vector fragments as follows:
    1) a cloning-acceptor fragment having upstream and downstream acceptor overhangs; and
    2) a counter-selection fragment.

8. The vector of claim 7 wherein comprising at least one of:
    said upstream acceptor overhang comprises the complement of the first two nucleotides of the initiation codon of said Expression Control Region polynucleotide;
    said vector comprises a coding sequence for a peptide or protein domain initiated at said Expression Control Region polynucleotide and capable of N-terminal fusion to said target protein through said upstream acceptor overhang;
    said vector comprises a coding sequence for a peptide or protein domain following said downstream acceptor overhang and capable of C-terminal fusion to said target protein through said downstream acceptor overhang;
    said vector comprises a coding sequence for a peptide or protein domain initiated at said Expression Control Region polynucleotide and capable of N terminal fusion to said target protein through said upstream acceptor overhang, and a coding sequence for a peptide or protein domain following said downstream acceptor overhang and capable of C-terminal fusion to said target protein through said downstream acceptor overhang; and
    said upstream acceptor overhang is the complement of 5'-CCAT and said downstream acceptor overhang is 5'-AGTG.

* * * * *

```
                           SEQUENCE LISTING

<160> NUMBER OF SEQ ID NOS: 102

<210> SEQ ID NO 1
<211> LENGTH: 2650
<212> TYPE: DNA
<213> ORGANISM: Artificial Sequence
<220> FEATURE:
<223> OTHER INFORMATION: Synthetic sequence

<400> SEQUENCE: 1
gtacggaaga ctacatgtgg tctcccatgg cgtctctcat gaaccggtaa aatacataag      60
gcttactaaa agccagataa cagtatgcgt atttgcgcgc tgattttgc ggtataagaa     120 tatatactga tatctatacc cgaagtatgt caaaagagg tgtgctatgc agtttaaggt     180
ttacacctat aaaagagaga gccgttatcg tctgtttgtg gatgtacaga gtgatattat     240
tgacacgcct gggcgacgca tggtgatccc cctggccagt gcacgtctgc tgtcagataa     300
agtctcccgt gaactttacc cggtggtgca tatcggggat gaaagctggc gcatgatgac     360
caccgatatg gccagtgtgc cagtctccgt tatcggggaa gaagtggctg atctcagcca     420
ccgcgaaaat gacatcaaaa acgccattaa cctgatgttc tggggaatat aacggccgta     480
tacactgcca ctcctcctgc actacattgc gcatccgcct ccagtgagct cagactagga     540
tccaggcgcg ccagttataa gcggccgcat cctgcagggt taattaagcg atcgcattta     600
aatcagcccg ggcagtttaa acaggtaccg ctgagcaata actagcataa cccccttgggg    660 cctctaaacg ggtcttgagg ggttttttgc tgaaagctta cgccccgccc tgccactcat     720
cgcagtactg ttgtaattca ttaagcattc tgccgacatg gaagccatca caaacggcat     780
gatgaacctg aatcgccagc ggcatcagca ccttgtcgcc ttgcgtataa tatttgccca     840
tagtgaaaac ggggcgaag aagttgtcca tattggccac gtttaaatca aaactggtga     900
aactcaccca gggattggct gagacgaaaa acatattctc aataaaccct ttagggaaat     960
aggccaggtt tcaccgtaa cacgccacat cttgcgaata tatgtgtaga aactgccgga    1020
aatcgtcgtg gtattcactc caaagcgatg aaaacgtttc agtttgctca tggaaaacgg    1080
tgtaacaagg gtgaacacta tcccatatca ccagctcacc gtctttcatt gccatacgga    1140
attccggatg agcattcatc aggcgggcaa gaatgtgaat aaaggccgga taaaacttgt    1200
gcttattttt ctttacggtc tttaaaaagg ccgtaatatc cagctgaacg gtctggttat    1260
aggtacattg agcaactgac tgaaatgcct caaaatgttc tttacgatgc cattgggata    1320
tatcaacggt ggtatatcca gtgatttttt tctccatttt agcttcctta gctcctgaaa    1380
atctcgataa ctcaaaaaat acgcccggta gtgatcttat ttcattatgg tgaaagttgg    1440
aacctcttac gtgccgatca acgtctcatt ttcgccaaaa gttggcccag ggcttccgg    1500 tatcaacagg gacaccagga tttatttatt ctgcgaagtg atcttccgtc acaggtattt    1560
attcccatga ccaaaatccc ttaacgtgag ttttcgttcc actgagcgtc agacccgta    1620 gaaaagatca aaggatcttc ttgagatcct tttttctgc gcgtaatctg ctgcttgcaa    1680
acaaaaaaac caccgctacc agcggtggtt tgtttgccgg atcaagagct accaactctt    1740
tttccgaagg taactggctt cagcagagcg cagataccaa atactgtcct tctagtgtag    1800
ccgtagttag gccaccactt caagaactct gtagcaccgc ctacatacct cgctctgcta    1860
```

```
atcctgttac cagtggctgc tgccagtggc gataagtcgt gtcttaccgg gttggactca    1920
agacgatagt taccggataa ggcgcagcgg tcgggctgaa cgggggttc gtgcacacag     1980 cccagcttgg agcgaacgac ctacaccgaa ctgagatacc tacagcgtga gctatgagaa    2040
agcgccacgc ttcccgaagg gagaaaggcg gacaggtatc cggtaagcgg cagggtcgga    2100
acaggagagc gcacgaggga gcttccaggg ggaaacgcct ggtatcttta tagtcctgtc    2160
gggtttcgcc acctctgact tgagcgtcga ttttgtgat gctcgtcagg ggggcggagc     2220
ctatggaaaa acgccagcaa cgcggccttt ttacggttcc tggcctttg ctggcctttt     2280 gctcacatgt tctttcctgc gttatcccct gattctgtgg ataaccgtat taccgccttt    2340
gagtgagctg ataccgctcg ccgcagccga acgaccgagc gcagcgagtc agtgagcgag    2400
gaagcgctag gatcagtaga tctcaaataa aacgaaaggc tcagtcgaaa gactgggcct    2460
ttcgttttat ctgttgtttg tcggtgaacg ctctcctgag taggacaaat ccgccgggag    2520
cggatttgaa cgttgcgaag caacggcccg gagggtggcg ggcaggacgc ccgccataaa    2580
ctgccaggca tcaaattaag cagaaggcca tcctgacgga tggcctttt gcgtttctac     2640 aaactcttcc                                                          2650

<210> SEQ ID NO 2
<211> LENGTH: 436
<212> TYPE: DNA
<213> ORGANISM: Artificial Sequence
<220> FEATURE:
<223> OTHER INFORMATION: Synthetic sequence

<400> SEQUENCE: 2
accggtaaaa tacataaggc ttactaaaag ccagataaca gtatgcgtat ttgcgcgctg      60
atttttgcgg tataagaata tatactgata tctatacccg aagtatgtca aaagaggtg     120 tgctatgcag tttaaggttt acacctataa aagagagagc cgttatcgtc tgtttgtgga    180
tgtacagagt gatattattg acacgcctgg gcgacgcatg gtgatccccc tggccagtgc    240
acgtctgctg tcagataaag tctcccgtga actttacccg gtggtgcata tcggggatga    300
aagctggcgc atgatgacca ccgatatggc cagtgtgcca gtctccgtta tcggggaaga    360
agtggctgat ctcagccacc gcgaaaatga catcaaaaac gccattaacc tgatgttctg    420
gggaatataa cggccg                                                   436

<210> SEQ ID NO 3
<211> LENGTH: 49
<212> TYPE: DNA
<213> ORGANISM: Artificial Sequence
<220> FEATURE:
<223> OTHER INFORMATION: Synthetic sequence

<400> SEQUENCE: 3
cgtacggaag actacatgtg gtctcccatg gcgtctctca tgaaccggt                 49

<210> SEQ ID NO 4
<211> LENGTH: 59
<212> TYPE: DNA
<213> ORGANISM: Artificial Sequence
<220> FEATURE:
<223> OTHER INFORMATION: Synthetic sequence

<400> SEQUENCE: 4
cggccgtata cactgccact cctcctgcac tacattgcgc atccgcctcc agtgagctc      59
```

<210> SEQ ID NO 5
<211> LENGTH: 59
<212> TYPE: DNA
<213> ORGANISM: Artificial Sequence
<220> FEATURE:
<223> OTHER INFORMATION: Synthetic sequence

<400> SEQUENCE: 5
cggccgtatg cactgccact cctcctgcac tgcattgcgc atccgcctcc agtgagctc    59

<210> SEQ ID NO 6
<211> LENGTH: 28
<212> TYPE: DNA
<213> ORGANISM: Artificial Sequence
<220> FEATURE:
<223> OTHER INFORMATION: Synthetic sequence

<400> SEQUENCE: 6
aaggagatat accatggcta gcaccggt                                      28

<210> SEQ ID NO 7
<211> LENGTH: 29
<212> TYPE: DNA
<213> ORGANISM: Artificial Sequence
<220> FEATURE:
<223> OTHER INFORMATION: Synthetic sequence

<400> SEQUENCE: 7
cggccggagg agtcactgac taagagctc                                     29

<210> SEQ ID NO 8
<211> LENGTH: 93
<212> TYPE: DNA
<213> ORGANISM: Artificial Sequence
<220> FEATURE:
<223> OTHER INFORMATION: Synthetic sequence

<400> SEQUENCE: 8
acttcgaaat taatacgact cactataggg agaccacaac ggtttccctc tagaaataat    60
tttgtttaac tttaagaagg agatatacat atg                                 93

<210> SEQ ID NO 9
<211> LENGTH: 93
<212> TYPE: DNA
<213> ORGANISM: Artificial Sequence
<220> FEATURE:
<223> OTHER INFORMATION: Synthetic sequence

<400> SEQUENCE: 9
cccgcgaaat taatacgact cactataggg agaccacaac ggtttccctc tagaaataat    60
tttgtttaac tttaagaagg agatatacat atg                                 93

<210> SEQ ID NO 10
<211> LENGTH: 100
<212> TYPE: DNA
<213> ORGANISM: Artificial Sequence
<220> FEATURE:
<223> OTHER INFORMATION: Synthetic sequence

<400> SEQUENCE: 10
cccgcgaaat taatacgact cactataggg gaattgtgag cggataacaa ttcccctcta    60
gaaataattt tgtttaactt taagaaggag ataccatg                           100

```
<210> SEQ ID NO 11
<211> LENGTH: 101
<212> TYPE: DNA
<213> ORGANISM: Artificial Sequence
<220> FEATURE:
<223> OTHER INFORMATION: Synthetic sequence

<400> SEQUENCE: 11
attccgaaat taatacgact cactataggg gaattgtgag cggataacaa ttcccctcta      60
gaaataattt tgtttaactt taagaaggag atatacatat g                        101

<210> SEQ ID NO 12
<211> LENGTH: 100
<212> TYPE: DNA
<213> ORGANISM: Artificial Sequence
<220> FEATURE:
<223> OTHER INFORMATION: Synthetic sequence

<400> SEQUENCE: 12
attccgaaat taatacgact cactataggg gaattgtgag cgctcacaat tcccctctag      60
aaataatttt gtttaacttt aagaaggaga tatacatatg                          100

<210> SEQ ID NO 13
<211> LENGTH: 56
<212> TYPE: DNA
<213> ORGANISM: Artificial Sequence
<220> FEATURE:
<223> OTHER INFORMATION: Synthetic sequence

<400> SEQUENCE: 13
cgtacgaaat taatacgact cactataggg gaattgtgag cggataacaa ttcccc         56

<210> SEQ ID NO 14
<211> LENGTH: 54
<212> TYPE: DNA
<213> ORGANISM: Artificial Sequence
<220> FEATURE:
<223> OTHER INFORMATION: Synthetic sequence

<400> SEQUENCE: 14
cgtacgaaat taatacgact cactataggg aattgtgagc ggataacaat tccc           54

<210> SEQ ID NO 15
<211> LENGTH: 52
<212> TYPE: DNA
<213> ORGANISM: Artificial Sequence
<220> FEATURE:
<223> OTHER INFORMATION: Synthetic sequence

<400> SEQUENCE: 15
cgtacgaaat taatacgact cactatagga attgtgagcg gataacaatt cc             52

<210> SEQ ID NO 16
<211> LENGTH: 49
<212> TYPE: DNA
<213> ORGANISM: Artificial Sequence
<220> FEATURE:
<223> OTHER INFORMATION: Synthetic sequence

<400> SEQUENCE: 16
cgtacgaaat taatacgact cactatagaa ttgtgagcgg ataacaatt                 49

<210> SEQ ID NO 17
<211> LENGTH: 52
<212> TYPE: DNA
```

```
<213> ORGANISM: Artificial Sequence
<220> FEATURE:
<223> OTHER INFORMATION: Synthetic sequence

<400> SEQUENCE: 17
cgtacgaaat taatacgact cactataggg gaattgtgag cgctcacaat tc         52

<210> SEQ ID NO 18
<211> LENGTH: 51
<212> TYPE: DNA
<213> ORGANISM: Artificial Sequence
<220> FEATURE:
<223> OTHER INFORMATION: Synthetic sequence

<400> SEQUENCE: 18
cgtacgaaat taatacgact cactataggg gaattgtgag cgctcacaat t          51

<210> SEQ ID NO 19
<211> LENGTH: 51
<212> TYPE: DNA
<213> ORGANISM: Artificial Sequence
<220> FEATURE:
<223> OTHER INFORMATION: Synthetic sequence

<400> SEQUENCE: 19
cgtacgaaat taatacgact cactataggg gaattgtgag cgctcacaat t          51

<210> SEQ ID NO 20
<211> LENGTH: 54
<212> TYPE: DNA
<213> ORGANISM: Artificial Sequence
<220> FEATURE:
<223> OTHER INFORMATION: Synthetic sequence

<400> SEQUENCE: 20
cgtacgaaat taatacgact cactataggg aattgtgagc gctcacaatt cccc       54

<210> SEQ ID NO 21
<211> LENGTH: 53
<212> TYPE: DNA
<213> ORGANISM: Artificial Sequence
<220> FEATURE:
<223> OTHER INFORMATION: Synthetic sequence

<400> SEQUENCE: 21
cgtacgaaat taatacgact cactataggg aattgtgagc gctcacaatt ccc        53

<210> SEQ ID NO 22
<211> LENGTH: 52
<212> TYPE: DNA
<213> ORGANISM: Artificial Sequence
<220> FEATURE:
<223> OTHER INFORMATION: Synthetic sequence

<400> SEQUENCE: 22
cgtacgaaat taatacgact cactataggg aattgtgagc gctcacaatt cc         52

<210> SEQ ID NO 23
<211> LENGTH: 51
<212> TYPE: DNA
<213> ORGANISM: Artificial Sequence
<220> FEATURE:
<223> OTHER INFORMATION: Synthetic sequence

<400> SEQUENCE: 23
cgtacgaaat taatacgact cactataggg aattgtgagc gctcacaatt c          51
```

<210> SEQ ID NO 24
<211> LENGTH: 50
<212> TYPE: DNA
<213> ORGANISM: Artificial Sequence
<220> FEATURE:
<223> OTHER INFORMATION: Synthetic sequence

<400> SEQUENCE: 24
cgtacgaaat taatacgact cactataggg aattgtgagc gctcacaatt     50

<210> SEQ ID NO 25
<211> LENGTH: 50
<212> TYPE: DNA
<213> ORGANISM: Artificial Sequence
<220> FEATURE:
<223> OTHER INFORMATION: Synthetic sequence

<400> SEQUENCE: 25
cgtacgaaat taatacgact cactataggg aattgtgagc gctcacaatt     50

<210> SEQ ID NO 26
<211> LENGTH: 53
<212> TYPE: DNA
<213> ORGANISM: Artificial Sequence
<220> FEATURE:
<223> OTHER INFORMATION: Synthetic sequence

<400> SEQUENCE: 26
cgtacgaaat taatacgact cactatagga attgtgagcg ctcacaattc ccc     53

<210> SEQ ID NO 27
<211> LENGTH: 52
<212> TYPE: DNA
<213> ORGANISM: Artificial Sequence
<220> FEATURE:
<223> OTHER INFORMATION: Synthetic sequence

<400> SEQUENCE: 27
cgtacgaaat taatacgact cactatagga attgtgagcg ctcacaattc cc     52

<210> SEQ ID NO 28
<211> LENGTH: 51
<212> TYPE: DNA
<213> ORGANISM: Artificial Sequence
<220> FEATURE:
<223> OTHER INFORMATION: Synthetic sequence

<400> SEQUENCE: 28
cgtacgaaat taatacgact cactatagga attgtgagcg ctcacaattc c     51

<210> SEQ ID NO 29
<211> LENGTH: 50
<212> TYPE: DNA
<213> ORGANISM: Artificial Sequence
<220> FEATURE:
<223> OTHER INFORMATION: Synthetic sequence

<400> SEQUENCE: 29
cgtacgaaat taatacgact cactatagga attgtgagcg ctcacaattc     50

<210> SEQ ID NO 30
<211> LENGTH: 49
<212> TYPE: DNA
<213> ORGANISM: Artificial Sequence
<220> FEATURE:

<223> OTHER INFORMATION: Synthetic sequence

<400> SEQUENCE: 30
cgtacgaaat taatacgact cactatagga attgtgagcg ctcacaatt        49

<210> SEQ ID NO 31
<211> LENGTH: 49
<212> TYPE: DNA
<213> ORGANISM: Artificial Sequence
<220> FEATURE:
<223> OTHER INFORMATION: Synthetic sequence

<400> SEQUENCE: 31
cgtacgaaat taatacgact cactatagga attgtgagcg ctcacaatt        49

<210> SEQ ID NO 32
<211> LENGTH: 48
<212> TYPE: DNA
<213> ORGANISM: Artificial Sequence
<220> FEATURE:
<223> OTHER INFORMATION: Synthetic sequence

<400> SEQUENCE: 32
cgtacgaaat taatacgact cactatagaa ttgtgagcgc tcacaatt         48

<210> SEQ ID NO 33
<211> LENGTH: 101
<212> TYPE: DNA
<213> ORGANISM: Artificial Sequence
<220> FEATURE:
<223> OTHER INFORMATION: Synthetic sequence

<400> SEQUENCE: 33
ttgtgtggaa ttgtgagcgg ataacaattt cacacagaaa cagctccctc gtacgaaatt        60
aatacgactc actatagggg aattgtgagc gctcacaatt c        101

<210> SEQ ID NO 34
<211> LENGTH: 100
<212> TYPE: DNA
<213> ORGANISM: Artificial Sequence
<220> FEATURE:
<223> OTHER INFORMATION: Synthetic sequence

<400> SEQUENCE: 34
ttgtgtggaa ttgtgagcgg ataacaattt cacacagaaa cagctccctc gtacgaaatt        60
aatacgactc actatagggg aattgtgagc gctcacaatt        100

<210> SEQ ID NO 35
<211> LENGTH: 100
<212> TYPE: DNA
<213> ORGANISM: Artificial Sequence
<220> FEATURE:
<223> OTHER INFORMATION: Synthetic sequence

<400> SEQUENCE: 35
ttgtgtggaa ttgtgagcgg ataacaattt cacacagaaa cagctccctc gtacgaaatt        60
aatacgactc actatagggg aattgtgagc gctcacaatt        100

<210> SEQ ID NO 36
<211> LENGTH: 103
<212> TYPE: DNA
<213> ORGANISM: Artificial Sequence
<220> FEATURE:
<223> OTHER INFORMATION: Synthetic sequence

```
<400> SEQUENCE: 36
ttgtgtggaa ttgtgagcgg ataacaattt cacacagaaa cagctccctc gtacgaaatt    60
aatacgactc actataggga attgtgagcg ctcacaattc ccc                      103

<210> SEQ ID NO 37
<211> LENGTH: 102
<212> TYPE: DNA
<213> ORGANISM: Artificial Sequence
<220> FEATURE:
<223> OTHER INFORMATION: Synthetic sequence

<400> SEQUENCE: 37
ttgtgtggaa ttgtgagcgg ataacaattt cacacagaaa cagctccctc gtacgaaatt    60
aatacgactc actataggga attgtgagcg ctcacaattc cc                       102

<210> SEQ ID NO 38
<211> LENGTH: 101
<212> TYPE: DNA
<213> ORGANISM: Artificial Sequence
<220> FEATURE:
<223> OTHER INFORMATION: Synthetic sequence

<400> SEQUENCE: 38
ttgtgtggaa ttgtgagcgg ataacaattt cacacagaaa cagctccctc gtacgaaatt    60
aatacgactc actataggga attgtgagcg ctcacaattc c                        101

<210> SEQ ID NO 39
<211> LENGTH: 100
<212> TYPE: DNA
<213> ORGANISM: Artificial Sequence
<220> FEATURE:
<223> OTHER INFORMATION: Synthetic sequence

<400> SEQUENCE: 39
ttgtgtggaa ttgtgagcgg ataacaattt cacacagaaa cagctccctc gtacgaaatt    60
aatacgactc actataggga attgtgagcg ctcacaattc                          100

<210> SEQ ID NO 40
<211> LENGTH: 99
<212> TYPE: DNA
<213> ORGANISM: Artificial Sequence
<220> FEATURE:
<223> OTHER INFORMATION: Synthetic sequence

<400> SEQUENCE: 40
ttgtgtggaa ttgtgagcgg ataacaattt cacacagaaa cagctccctc gtacgaaatt    60
aatacgactc actataggga attgtgagcg ctcacaatt                           99

<210> SEQ ID NO 41
<211> LENGTH: 99
<212> TYPE: DNA
<213> ORGANISM: Artificial Sequence
<220> FEATURE:
<223> OTHER INFORMATION: Synthetic sequence

<400> SEQUENCE: 41
ttgtgtggaa ttgtgagcgg ataacaattt cacacagaaa cagctccctc gtacgaaatt    60
aatacgactc actataggga attgtgagcg ctcacaatt                           99

<210> SEQ ID NO 42
```

```
<211> LENGTH: 102
<212> TYPE: DNA
<213> ORGANISM: Artificial Sequence
<220> FEATURE:
<223> OTHER INFORMATION: Synthetic sequence

<400> SEQUENCE: 42
ttgtgtggaa ttgtgagcgg ataacaattt cacacagaaa cagctccctc gtacgaaatt      60
aatacgactc actataggaa ttgtgagcgc tcacaattcc cc                         102

<210> SEQ ID NO 43
<211> LENGTH: 101
<212> TYPE: DNA
<213> ORGANISM: Artificial Sequence
<220> FEATURE:
<223> OTHER INFORMATION: Synthetic sequence

<400> SEQUENCE: 43
ttgtgtggaa ttgtgagcgg ataacaattt cacacagaaa cagctccctc gtacgaaatt      60
aatacgactc actataggaa ttgtgagcgc tcacaattcc c                          101

<210> SEQ ID NO 44
<211> LENGTH: 100
<212> TYPE: DNA
<213> ORGANISM: Artificial Sequence
<220> FEATURE:
<223> OTHER INFORMATION: Synthetic sequence

<400> SEQUENCE: 44
ttgtgtggaa ttgtgagcgg ataacaattt cacacagaaa cagctccctc gtacgaaatt      60
aatacgactc actataggaa ttgtgagcgc tcacaattcc                            100

<210> SEQ ID NO 45
<211> LENGTH: 99
<212> TYPE: DNA
<213> ORGANISM: Artificial Sequence
<220> FEATURE:
<223> OTHER INFORMATION: Synthetic sequence

<400> SEQUENCE: 45
ttgtgtggaa ttgtgagcgg ataacaattt cacacagaaa cagctccctc gtacgaaatt      60
aatacgactc actataggaa ttgtgagcgc tcacaattc                             99

<210> SEQ ID NO 46
<211> LENGTH: 98
<212> TYPE: DNA
<213> ORGANISM: Artificial Sequence
<220> FEATURE:
<223> OTHER INFORMATION: Synthetic sequence

<400> SEQUENCE: 46
ttgtgtggaa ttgtgagcgg ataacaattt cacacagaaa cagctccctc gtacgaaatt      60
aatacgactc actataggaa ttgtgagcgc tcacaatt                              98

<210> SEQ ID NO 47
<211> LENGTH: 98
<212> TYPE: DNA
<213> ORGANISM: Artificial Sequence
<220> FEATURE:
<223> OTHER INFORMATION: Synthetic sequence
```

<400> SEQUENCE: 47
ttgtgtggaa ttgtgagcgg ataacaattt cacacagaaa cagctccctc gtacgaaatt    60
aatacgactc actataggaa ttgtgagcgc tcacaatt                            98

<210> SEQ ID NO 48
<211> LENGTH: 44
<212> TYPE: DNA
<213> ORGANISM: Artificial Sequence
<220> FEATURE:
<223> OTHER INFORMATION: Synthetic squence

<400> SEQUENCE: 48
tctagaaata attttgttta actttaagaa ggagatatac catg                      44

<210> SEQ ID NO 49
<211> LENGTH: 40
<212> TYPE: DNA
<213> ORGANISM: Artificial Sequence
<220> FEATURE:
<223> OTHER INFORMATION: Synthetic sequence

<400> SEQUENCE: 49
tctagaaatt tctttaactt taagaaggag ataccatg                             40

<210> SEQ ID NO 50
<211> LENGTH: 32
<212> TYPE: DNA
<213> ORGANISM: Artificial Sequence
<220> FEATURE:
<223> OTHER INFORMATION: Synthetic sequence

<400> SEQUENCE: 50
tctagataac tttaagaagg agatatacca tg                                   32

<210> SEQ ID NO 51
<211> LENGTH: 31
<212> TYPE: DNA
<213> ORGANISM: Artificial Sequence
<220> FEATURE:
<223> OTHER INFORMATION: Synthetic sequence

<400> SEQUENCE: 51
tctagaaact ttaagaagga gataccat g                                      31

<210> SEQ ID NO 52
<211> LENGTH: 30
<212> TYPE: DNA
<213> ORGANISM: Artificial Sequence
<220> FEATURE:
<223> OTHER INFORMATION: Synthetic sequence

<400> SEQUENCE: 52
tctagaactt taagaaggag ataccatg                                        30

<210> SEQ ID NO 53
<211> LENGTH: 30
<212> TYPE: DNA
<213> ORGANISM: Artificial Sequence
<220> FEATURE:
<223> OTHER INFORMATION: Synthetic sequence

<400> SEQUENCE: 53
tctagaaatt taagaaggag ataccatg                                        30

<210> SEQ ID NO 54
<211> LENGTH: 29
<212> TYPE: DNA
<213> ORGANISM: Artificial Sequence
<220> FEATURE:
<223> OTHER INFORMATION: Synthetic sequence

<400> SEQUENCE: 54
tctagacttt aagaaggaga tataccatg                              29

<210> SEQ ID NO 55
<211> LENGTH: 28
<212> TYPE: DNA
<213> ORGANISM: Artificial Sequence
<220> FEATURE:
<223> OTHER INFORMATION: Synthetic sequence

<400> SEQUENCE: 55
tctagaaata agaaggagat ataccatg                               28

<210> SEQ ID NO 56
<211> LENGTH: 26
<212> TYPE: DNA
<213> ORGANISM: Artificial Sequence
<220> FEATURE:
<223> OTHER INFORMATION: Synthetic sequence

<400> SEQUENCE: 56
tctagataag aaggagatat accatg                                 26

<210> SEQ ID NO 57
<211> LENGTH: 24
<212> TYPE: DNA
<213> ORGANISM: Artificial Sequence
<220> FEATURE:
<223> OTHER INFORMATION: Synthetic sequence

<400> SEQUENCE: 57
tctagaagaa ggagatatac catg                                   24

<210> SEQ ID NO 58
<211> LENGTH: 21
<212> TYPE: DNA
<213> ORGANISM: Artificial Sequence
<220> FEATURE:
<223> OTHER INFORMATION: Synthetic sequence

<400> SEQUENCE: 58
tctagaagga gatataccat g                                      21

<210> SEQ ID NO 59
<211> LENGTH: 28
<212> TYPE: DNA
<213> ORGANISM: Artificial Sequence
<220> FEATURE:
<223> OTHER INFORMATION: Synthetic sequence

<400> SEQUENCE: 59
tctagaagac tacatgtggt ctcccatg                               28

<210> SEQ ID NO 60
<211> LENGTH: 80
<212> TYPE: DNA
<213> ORGANISM: Artificial Sequence
<220> FEATURE:
<223> OTHER INFORMATION: Synthetic sequence

<400> SEQUENCE: 60

| | | |
|---|---|---|
| acaccatcga atggcgcaaa acctttcgcg gtatggcatg atagcgcccg gaagagagtc | | 60 |
| aattcagggt ggtgaatgtg | | 80 |

<210> SEQ ID NO 61
<211> LENGTH: 87
<212> TYPE: DNA
<213> ORGANISM: Artificial Sequence
<220> FEATURE:
<223> OTHER INFORMATION: Synthetic sequence

<400> SEQUENCE: 61

| | | |
|---|---|---|
| agatctacac catcgaatgg cgcaaaacct ttcgcggtat ggcatgatag cgcccgggaa | | 60 |
| gagagtcaat taaggagata tatcatg | | 87 |

<210> SEQ ID NO 62
<211> LENGTH: 4483
<212> TYPE: DNA
<213> ORGANISM: Artificial Sequence
<220> FEATURE:
<223> OTHER INFORMATION: Synthetic sequence

<400> SEQUENCE: 62

| | | |
|---|---|---|
| gtacgaaatt aatacgactc actataggga attgtgagcg ctcacaattc tctagaaata | | 60 |
| attttgttta actttaagaa ggagatatac catggctagc accggtaaaa tacataaggc | | 120 |
| ttactaaaag ccagataaca gtatgcgtat ttgcgcgctg attttttgcgg tataagaata | | 180 |
| tatactgata tctatacccg aagtatgtca aaaagaggtg tgctatgcag tttaaggttt | | 240 |
| acacctataa aagagagagc cgttatcgtc tgtttgtgga tgtacagagt gatattattg | | 300 |
| acacgcctgg gcgacgcatg gtgatccccc tggccagtgc acgtctgctg tcagataaag | | 360 |
| tctcccgtga actttacccg gtggtgcata tcggggatga agctggcgc atgatgacca | | 420 |
| ccgatatggc cagtgtgcca gtctccgtta tcggggaaga agtggctgat ctcagccacc | | 480 |
| gcgaaaatga catcaaaaac gccattaacc tgatgttctg gggaatataa cggccggagg | | 540 |
| agtcactgac taagagctcc taagtgcagg gtctcaggcc taaattagct gcaggctaaa | | 600 |
| cctgcatttc gcgtaagact caagtcttat aactacgtaa ggatcctaag tttaaacagc | | 660 |
| ccgggcattt aaatcagcga tcgcaaggta ccgctgagca taactagca taaccccttg | | 720 |
| gggcctctaa acgggtcttg aggggttttt tgctgaaagc ttgaattctt agaaaaactc | | 780 |
| atcgagcatc aaatgaaact gcaatttatt catatcagga ttatcaatac catatttttg | | 840 |
| aaaagccgt ttctgtaatg aaggagaaaa ctcaccgagg cagttccata ggatggcaag | | 900 |
| atcctggtat cggtctgcga ttccgactcg tccaacatca atacaaccta ttaattccc | | 960 |
| ctcgtcaaaa ataaggttat caagtgagaa atcaccatga gtgacgactg aatccggtga | | 1020 |
| gaatggcaaa agcttatgca tttctttcca gacttgttca acaggccagc cattacgctc | | 1080 |
| gtcatcaaaa tcactcgcat caaccaaacc gttattcatt cgtgattgcg cctgagcgag | | 1140 |
| acgaaatacg cggtcgctgt taaaaggaca attacaaaca ggaatcgaat gcaaccggcg | | 1200 |
| caggaacact gccagcgcat caacaatatt ttcacctgaa tcaggatatt cttctaatac | | 1260 |
| ctggaatgct gttttcccgg ggatcgcagt ggtgagtaac catgcatcat caggagtacg | | 1320 |
| gataaaatgc ttgatggtcg gaagaggcat aaattccgtc agccagttta gtctgaccat | | 1380 |
| ctcatctgta acatcattgg caacgctacc tttgccatgt ttcagaaaca actctggcgc | | 1440 |

```
atcgggcttc ccatacaatc gatagattgt cgcacctgat tgcccgacat tatcgcgagc   1500
ccatttatac ccatataaat cagcatccat gttggaattt aatcgcggcc tcgagcaaga   1560
cgtttcccgt tgaatatggc tcataacacc ccttgtatta ctgtttatgt aagcagacag   1620
ttttattgtt catgaccaaa atcccttaac gtgagttttc gttccactga gcgtcagacc   1680
ccgtagaaaa gatcaaagga tcttcttgag atccttttt tctgcgcgta atctgctgct    1740
tgcaaacaaa aaaaccaccg ctaccagcgg tggtttgttt gccggatcaa gagctaccaa   1800
ctcttttttcc gaaggtaact ggcttcagca gagcgcagat accaaatact gtccttctag  1860
tgtagccgta gttaggccac cacttcaaga actctgtagc accgcctaca tacctcgctc   1920
tgctaatcct gttaccagtg gctgctgcca gtggcgataa gtcgtgtctt accgggttgg   1980
actcaagacg atagttaccg gataaggcgc agcggtcggg ctgaacgggg ggttcgtgca   2040
cacagcccag cttggagcga acgacctaca ccgaactgag atacctacag cgtgagctat   2100
gagaaagcgc cacgcttccc gaagggagaa aggcggacag gtatccggta agcggcaggg   2160
tcggaacagg agagcgcacg agggagcttc caggggggaaa cgcctggtat ctttatagtc   2220
ctgtcgggtt tcgccacctc tgacttgagc gtcgatttt gtgatgctcg tcaggggggc    2280
ggagcctatg gaaaaacgcc agcaacgcgg cctttttacg gttcctggcc ttttgctggc   2340
cttttgctca catgctcttt cctgcgttat ccctgattc tgtggataac cgtattaccg    2400
cctttgagtg agctgatacc gctcgccgca gccgaacgac cgagcgcagc gagtcagtga   2460
gcgaggaagc ggaagagcgc ctgatgcggt attttctcct tacgcatctg tgcggtattt   2520
cacaccgcat atatggtgca ctctcagtac aatctgctct gatgccgcat agttaagcca   2580
gtatacactc cgctatcgct acgtgactgg gtcatggctg cgccccgaca cccgccaaca   2640
cccgctgacg cgccctgacg ggcttgtctg ctcccggcat ccgcttacag acaagctgtg   2700
accgtctccg ggagctgcat gtgtcagagg ttttcaccgt catcaccgaa acgcgcgagg   2760
cagctgcggt aaagctcatc agcgtggtcg tgaagcgatt cacagatgtc tgcctgttca   2820
tccgcgtcca gctcgttgag tttctccaga agcgttaatg tctggcttct gataaagcgg   2880
gccatgttaa gggcggtttt ttcctgtttg gtcactgatg cctccgtgta agggggattt   2940
ctgttcatgg gggtaatgat accgatgaaa cgagagagga tgctcacgat acgggttact   3000
gatgatgaac atgcccggtt actggaacgt tgtgagggta aacaactggc ggtatggatg   3060
cggcgggacc agagaaaaat caccctaggt cactgcccgc tttccagtcg ggaaacctgt   3120
cgtgccagct gcattaatga atcggccaac gcgcggggag aggcggtttg cgtattgggc   3180
gccagggtgg ttttcttttt caccagtgag acggcaaca gctgattgcc cttcaccgcc    3240
tggccctgag agagttgcag caagcggtcc acgctggttt gccccagcag gcgaaaatcc   3300
tgtttgatgg tggttaacgg cgggatataa catgagctgt cttcggtatc gtcgtatccc   3360
actaccgaga tatccgcacc aacgcgcagc ccggactcgg taatggcgcg cattgcgccc   3420
agcgccatct gatcgttggc aaccagcatc gcagtgggaa cgatgccctc attcagcatt   3480
tgcatggttt gttgaaaacc ggacatggca ctccagtcgc cttcccgttc cgctatcggc   3540
tgaatttgat tgcgagtgag atatttatgc cagccagcca gacgcagacg cgccgagaca   3600
gaacttaatg ggcccgctaa cagcgcgatt tgctggtgac ccaatgcgac cagatgctcc   3660
acgcccagtc gcgtaccgtc ttcatgggag aaaataatac tgttgatggg tgtctggtca   3720
gagacatcaa gaaataacgc cggaacatta gtgcaggcag cttccacagc aatggcatcc   3780
tggtcatcca gcggatagtt aatgatcagc ccactgacgc gttgcgcgag aagattgtgc   3840
```

```
accgccgctt tacaggcttc gacgccgctt cgttctacca tcgacaccac cacgctggca    3900
cccagttgat cggcgcgaga tttaatcgcc gcgacaattt gcgacggcgc gtgcagggcc    3960
agactggagg tggcaacgcc aatcagcaac gactgtttgc ccgccagttg ttgtgccacg    4020
cggttgggaa tgtaattcag ctccgccatc gccgcttcca cttttccccg cgttttcgca    4080
gaaacgtggc tggcctggtt caccacgcgg gaaacggtct gataagagac accggcatac    4140
tctgcgacat cgtataacgt tactggtttc atgatatatc tccttaattg actctcttcc    4200
cgggcgctat catgccatac cgcgaaaggt tttgcgccat cgatggtgt agatctcaaa     4260 taaaacgaaa ggctcagtcg aaagactggg cctttcgttt tatctgttgt ttgtcggtga    4320
acgctctcct gagtaggaca atccgccgg gagcggattt gaacgttgcg aagcaacggc     4380
ccggagggtg gcgggcagga cgcccgccat aaactgccag gcatcaaatt aagcagaagg    4440
ccatcctgac ggatggcctt tttgcgtttc tacaaactct tcc                      4483
```

<210> SEQ ID NO 63
<211> LENGTH: 4482
<212> TYPE: DNA
<213> ORGANISM: Artificial Sequence
<220> FEATURE:
<223> OTHER INFORMATION: Synthetic sequence

<400> SEQUENCE: 63

```
gtacgaaatt aatacgactc actataggaa ttgtgagcgc tcacaattct ctagaaataa      60
ttttgtttaa ctttaagaag gagatatacc atggctagca ccgtaaaaat acataaggct     120
tactaaaagc cagataacag tatgcgtatt tgcgcgctga ttttgcggt ataagaatat      180 atactgatat ctatacccga agtatgtcaa aaagaggtgt gctatgcagt ttaaggttta     240
cacctataaa agagagagcc gttatcgtct gtttgtggat gtacagagtg atattattga     300
cacgcctggg cgacgcatgg tgatcccct ggccagtgca cgtctgctgt cagataaagt      360
ctcccgtgaa ctttacccgg tggtgcatat cggggatgaa agctggcgca tgatgaccac     420
cgatatggcc agtgtgccag tctccgttat cggggaagaa gtggctgatc tcagccaccg     480
cgaaaatgac atcaaaaacg ccattaaacct gatgttctgg ggaatataac ggccggagga    540
gtcactgact aagagctcct aagtgcaggg tctcaggcct aaattagctg caggctaaac     600
ctgcatttcg cgtaagactc aagtcttata actacgtaag gatcctaagt ttaaacagcc     660
cgggcattta aatcagcgat cgcaaggtac cgctgagcaa taactagcat aaccccttgg     720
ggcctctaaa cgggtcttga gggtttttt gctgaaagct tgaattctta gaaaactca      780 tcgagcatca aatgaaactg caattatttc atatcaggat tatcaatacc atattttga     840 aaaagccgtt tctgtaatga aggagaaaac tcaccgagc agttccatag gatggcaaga     900
tcctggtatc ggtctgcgat tccgactcgt ccaacatcaa tacaacctat aatttcccc     960 tcgtcaaaaa taaggttatc aagtgagaaa tcaccatgag tgacgactga atccggtgag    1020
aatggcaaaa gcttatgcat ttcttccag acttgttcaa caggccagcc attacgctcg     1080
tcatcaaaat cactcgcatc aaccaaaccg ttattcattc gtgattgcgc ctgagcgaga    1140
cgaaatacgc ggtcgctgtt aaaaggacaa ttacaaacag gaatcgaatg caaccggcgc    1200
aggaacactg ccagcgcatc aacaatattt tcacctgaat caggatattc ttctaatacc    1260
tggaatgctg ttttccgggg gatcgcagtg gtgagtaacc atgcatcatc aggagtacgg    1320
ataaaatgct tgatggtcgg aagaggcata aattccgtca gccagtttag tctgaccatc    1380
```

```
tcatctgtaa catcattggc aacgctacct ttgccatgtt tcagaaacaa ctctggcgca   1440
tcgggcttcc catacaatcg atagattgtc gcacctgatt gcccgacatt atcgcgagcc   1500
catttatacc catataaatc agcatccatg ttggaattta atcgcggcct cgagcaagac   1560
gtttcccgtt gaatatggct cataacaccc cttgtattac tgtttatgta agcagacagt   1620
tttattgttc atgaccaaaa tcccttaacg tgagttttcg ttccactgag cgtcagaccc   1680
cgtagaaaag atcaaaggat cttcttgaga tccttttttt ctgcgcgtaa tctgctgctt   1740
gcaaacaaaa aaccaccgc  taccagcggt ggtttgtttg ccggatcaag agctaccaac   1800 tcttttttccg aaggtaactg gcttcagcag agcgcagata ccaaatactg tccttctagt   1860
gtagccgtag ttaggccacc acttcaagaa ctctgtagca ccgcctacat acctcgctct   1920
gctaatcctg ttaccagtgg ctgctgccag tggcgataag tcgtgtctta ccgggttgga   1980
ctcaagacga tagttaccgg ataaggcgca gcggtcgggc tgaacggggg gttcgtgcac   2040
acagcccagc ttggagcgaa cgacctacac cgaactgaga tacctacagc gtgagctatg   2100
agaaagcgcc acgcttcccg aagggagaaa ggcggacagg tatccggtaa gcggcagggt   2160
cggaacagga gagcgcacga gggagcttcc agggggaaac gcctggtatc tttatagtcc   2220
tgtcgggttt cgccacctct gacttgagcg tcgatttttg tgatgctcgt caggggggcg   2280
gagcctatgg aaaaacgcca gcaacgcggc cttttacgg  ttcctggcct tttgctggcc   2340
ttttgctcac atgctctttc ctgcgttatc ccctgattct gtggataacc gtattaccgc   2400
ctttgagtga gctgataccg ctcgccgcag ccgaacgacc gagcgcagcg agtcagtgag   2460
cgaggaagcg gaagagcgcc tgatgcggta ttttctcctt acgcatctgt gcggtatttc   2520
acaccgcata tatggtgcac tctcagtaca atctgctctg atgccgcata gttaagccag   2580
tatacactcc gctatcgcta cgtgactggg tcatggctgc gccccgacac ccgccaacac   2640
ccgctgacgc gccctgacgg gcttgtctgc tcccggcatc cgcttacaga caagctgtga   2700
ccgtctccgg gagctgcatg tgtcagaggt tttcaccgtc atcaccgaaa cgcgcgaggc   2760
agctgcggta agctcatca  gcgtggtcgt gaagcgattc acagatgtct gcctgttcat   2820
ccgcgtccag ctcgttgagt ttctccagaa gcgttaatgt ctggcttctg ataaagcggg   2880
ccatgttaag gcggtttttt cctgtttggt tcactgatgc ctccgtgtaa gggggatttc   2940
tgttcatggg ggtaatgata ccgatgaaac gagagaggat gctcacgata cgggttactg   3000
atgatgaaca tgcccggtta ctggaacgtt gtgagggtaa acaactggcg gtatggatgc   3060
ggcgggacca gagaaaaatc accctaggtc actgcccgct ttccagtcgg gaaacctgtc   3120
gtgccagctg cattaatgaa tcggccaacg cgcggggaga ggcggtttgc gtattgggcg   3180
ccagggtggt ttttcttttc accagtgaga cgggcaacag ctgattgccc ttcaccgcct   3240
ggccctgaga gagttgcagc aagcggtcca cgctggtttg ccccagcagg cgaaaatcct   3300
gtttgatggt ggttaacggc gggatataac atgagctgtc ttcggtatcg tcgtatccca   3360
ctaccgagat atccgcacca acgcgcagcc cggactcggt aatggcgcgc attgcgccca   3420
gcgccatctg atcgttggca accagcatcg cagtgggaac gatgccctca ttcagcattt   3480
gcatggtttt ttgaaaaccg gacatggcac tccagtcgcc ttcccgttcc gctatcggct   3540
gaatttgatt gcgagtgaga tatttatgcc agccagccag acgcagacgc gccgagacag   3600
aacttaatgg gcccgctaac agcgcgattt gctggtgacc caatgcgacc agatgctcca   3660
cgcccagtcg cgtaccgtct tcatgggaga aataatactg ttgatgggt  gtctggtcag   3720 agacatcaag aaataacgcc ggaacattag tgcaggcagc ttccacagca atggcatcct   3780
```

```
ggtcatccag cggatagtta atgatcagcc cactgacgcg ttgcgcgaga agattgtgca    3840
ccgccgcttt acaggcttcg acgccgcttc gttctaccat cgacaccacc acgctggcac    3900
ccagttgatc ggcgcgagat ttaatcgccg cgacaatttg cgacggcgcg tgcagggcca    3960
gactggaggt ggcaacgcca atcagcaacg actgtttgcc cgccagttgt tgtgccacgc    4020
ggttgggaat gtaattcagc tccgccatcg ccgcttccac ttttcccgc gttttcgcag     4080 aaacgtggct ggcctggttc accacgcggg aaacggtctg ataagagaca ccggcatact    4140
ctgcgacatc gtataacgtt actggtttca tgatatatct ccttaattga ctctcttccc    4200
gggcgctatc atgccatacc gcgaaaggtt ttgcgccatt cgatggtgta gatctcaaat    4260
aaaacgaaag gctcagtcga agactgggc ctttcgtttt atctgttgtt tgtcggtgaa     4320
cgctctcctg agtaggacaa atccgccggg agcggatttg aacgttgcga agcaacggcc    4380
cggagggtgg cgggcaggac gcccgccata aactgccagg catcaaatta agcagaaggc    4440
catcctgacg gatggccttt ttgcgtttct acaaactctt cc                       4482

<210> SEQ ID NO 64
<211> LENGTH: 4542
<212> TYPE: DNA
<213> ORGANISM: Artificial Sequence
<220> FEATURE:
<223> OTHER INFORMATION: Synthetic sequence

<400> SEQUENCE: 64
gtacgaaatt aatacgactc actataggga attgtgagcg ctcacaattc tctagaaata     60
attttgttta actttaagaa ggagatatac catggctagc accggtaaaa tacataaggc    120
ttactaaaag ccagataaca gtatgcgtat ttgcgcgctg attttttgcgg tataagaata    180 tatactgata tctatacccg aagtatgtca aaaagaggtg tgctatgcag tttaaggttt    240
acacctataa aagagagagc cgttatcgtc tgtttgtgga tgtacagagt gatattattg    300
acacgcctgg gcgacgcatg gtgatccccc tggccagtgc acgtctgctg tcagataaag    360
tctcccgtga actttacccg gtggtgcata tcggggatga agctggcgc atgatgacca     420 ccgatatggc cagtgtgcca gtctccgtta tcggggaaga agtggctgat ctcagccacc    480
gcgaaaatga catcaaaaac gccattaacc tgatgttctg gggaatataa cggccggagg    540
agtcactgac taagagctcc taagtgcagg gtctcaggcc taaattagct gcaggctaaa    600
cctgcatttc gcgtaagact caagtcttat aactacgtaa ggatcctaag tttaaacagc    660
ccgggcattt aaatcagcga tcgcaaggta ccgctgagca taactagca taaccccttg     720 gggcctctaa acgggtcttg aggggttttt tgctgaaagc ttgaattctt agaaaaactc    780
atcgagcatc aaatgaaact gcaatttatt catatcagga ttatcaatac catattttg     840 aaaaagccgt ttctgtaatg aaggagaaaa ctcaccgagg cagttccata ggatggcaag    900
atcctggtat cggtctgcga ttccgactcg tccaacatca atacaaccta ttaatttccc    960
ctcgtcaaaa ataaggttat caagtgagaa atcaccatga gtgacgactg aatccggtga    1020
gaatggcaaa agcttatgca tttctttcca gacttgttca acaggccagc cattacgctc    1080
gtcatcaaaa tcactcgcat caaccaaacc gttattcatt cgtgattgcg cctgagcgag    1140
acgaaatacg cggtcgctgt taaaaggaca attacaaaca ggaatcgaat gcaaccggcg    1200
caggaacact gccagcgcat caacaatatt ttcacctgaa tcaggatatt cttctaatac    1260
ctggaatgct gttttcccgg ggatcgcagt ggtgagtaac catgcatcat caggagtacg    1320
```

```
gataaaatgc ttgatggtcg gaagaggcat aaattccgtc agccagttta gtctgaccat    1380
ctcatctgta acatcattgg caacgctacc tttgccatgt ttcagaaaca actctggcgc    1440
atcgggcttc ccatacaatc gatagattgt cgcacctgat tgcccgacat tatcgcgagc    1500
ccatttatac ccatataaat cagcatccat gttggaattt aatcgcggcc tcgagcaaga    1560
cgtttcccgt tgaatatggc tcataacacc ccttgtatta ctgtttatgt aagcagacag    1620
ttttattgtt catgaccaaa atcccttaac gtgagttttc gttccactga gcgtcagacc    1680
ccgtagaaaa gatcaaagga tcttcttgag atcctttttt tctgcgcgta atctgctgct    1740
tgcaaacaaa aaaaccaccg ctaccagcgg tggtttgttt gccggatcaa gagctaccaa    1800 ctcttttttcc gaaggtaact ggcttcagca gagcgcagat accaaatact gtccttctag    1860
tgtagccgta gttaggccac cacttcaaga actctgtagc accgcctaca tacctcgctc    1920
tgctaatcct gttaccagtg ctgctgcca gtggcgataa gtcgtgtctt accgggttgg      1980
actcaagacg atagttaccg gataaggcgc agcggtcggg ctgaacgggg ggttcgtgca    2040
cacagcccag cttggagcga acgacctaca ccgaactgag atacctacag cgtgagctat    2100
gagaaagcgc cacgcttccc gaagggagaa aggcggacag gtatccggta agcggcaggg    2160
tcggaacagg agagcgcacg agggagcttc caggggggaaa cgcctggtat ctttatagtc    2220
ctgtcgggtt tcgccacctc tgacttgagc gtcgatttt gtgatgctcg tcagggggc     2280 ggagcctatg gaaaaacgcc agcaacgcgg ccttttttacg gttcctggcc ttttgctggc    2340
cttttgctca catgctcttt cctgcgttat ccctgattc tgtggataac cgtattaccg     2400
cctttgagtg agctgatacc gctcgccgca gccgaacgac cgagcgcagc gagtcagtga    2460
gcgaggaagc ggaagagcgc ctgatgcggt attttctcct tacgcatctg tgcggtattt    2520
cacaccgcat atatggtgca ctctcagtac aatctgctct gatgccgcat agttaagcca    2580
gtatacactc cgctatcgct acgtgactgg gtcatggctg cgccccgaca cccgccaaca    2640
cccgctgacg cgccctgacg ggcttgtctg ctcccggcat ccgcttacag acaagctgtg    2700
accgtctccg ggagctgcat gtgtcagagg ttttcaccgt catcaccgaa acgcgcgagg    2760
cagctgcggt aaagctcatc agcgtggtcg tgaagcgatt cacagatgtc tgcctgttca    2820
tccgcgtcca gctcgttgag tttctccaga agcgttaatg tctggcttct gataaagcgg    2880
gccatgttaa gggcggtttt ttcctgtttg gtcactgatg cctccgtgta agggggattt    2940
ctgttcatgg gggtaatgat accgatgaaa cgagagagga tgctcacgat acgggttact    3000
gatgatgaac atgcccggtt actggaacgt tgtgagggta acaactggc ggtatggatg      3060 cggcgggacc agagaaaaat caccctaggt cactgcccgc tttccagtcg ggaaacctgt    3120
cgtgccagct gcattaatga atcggccaac gcgcggggag aggcggtttg cgtattgggc    3180
gccagggtgg ttttcttttt caccagtgag acggcaaca gctgattgcc cttcaccgcc      3240
tggccctgag agagttgcag caagcggtcc acgctggttt gccccagcag gcgaaaatcc    3300
tgtttgatgg tggttaacgg cgggatataa catgagctgt cttcggtatc gtcgtatccc    3360
actaccgaga tatccgcacc aacgcgcagc ccggactcgg taatggcgcg cattgcgccc    3420
agcgccatct gatcgttggc aaccagcatc gcagtgggaa cgatgccctc attcagcatt    3480
tgcatggttt gttgaaaacc ggacatggca ctccagtcgc cttcccgttc cgctatcggc    3540
tgaatttgat tgcgagtgag atatttatgc cagccagcca gacgcagacg cgccgagaca    3600
gaacttaatg ggcccgctaa cagcgcgatt tgctggtgac ccaatgcgac cagatgctcc    3660
acgcccagtc gcgtaccgtc ttcatgggag aaaataatac tgttgatggg tgtctggtca    3720
```

```
gagacatcaa gaaataacgc cggaacatta gtgcaggcag cttccacagc aatggcatcc    3780
tggtcatcca gcggatagtt aatgatcagc ccactgacgc gttgcgcgag aagattgtgc    3840
accgccgctt tacaggcttc gacgccgctt cgttctacca tcgacaccac cacgctggca    3900
cccagttgat cggcgcgaga tttaatcgcc gcgacaattt gcgacggcgc gtgcagggcc    3960
agactggagg tggcaacgcc aatcagcaac gactgtttgc ccgccagttg ttgtgccacg    4020
cggttgggaa tgtaattcag ctccgccatc gccgcttcca cttttcccg cgttttcgca     4080 gaaacgtggc tggcctggtt caccacgcgg gaaacggtct gataagagac accggcatac    4140
tctgcgacat cgtataacgt tactggtttc atgatatatc tccttaattg actctcttcc    4200
cgggcgctat catgccatac cgcgaaaggt tttgcgccat tcgatggtgt agatctcaaa    4260
taaaacgaaa ggctcagtcg aaagactggg cctttcgttt tatctgttgt ttgtcggtga    4320
acgctctcct gagtaggaca atccgccgg gagcggattt gaacgttgcg aagcaacggc     4380
ccggagggtg gcgggcagga cgcccgccat aaactgccag gcatcaaatt aagcagaagg    4440
ccatcctgac ggatggcctt tttgcgtttc tacaaactct tccgtaccgc ggttgtgtgg    4500
aattgtgagc ggataacaat ttcacacaga aacagctccc tc                       4542

<210> SEQ ID NO 65
<211> LENGTH: 4541
<212> TYPE: DNA
<213> ORGANISM: Artificial Sequence
<220> FEATURE:
<223> OTHER INFORMATION: Synthetic sequence

<400> SEQUENCE: 65
gtacgaaatt aatacgactc actataggaa ttgtgagcgc tcacaattct ctagaaataa      60
ttttgtttaa cttaagaag gagatatacc atggctagca ccggtaaaat acataaggct      120
tactaaaagc cagataacag tatgcgtatt tgcgcgctga ttttgcggt ataagaatat       180 atactgatat ctataccga agtatgtcaa aaagaggtgt gctatgcagt ttaaggttta      240
cacctataaa agagagagcc gttatcgtct gtttgtggat gtacagagtg atattattga    300
cacgcctggg cgacgcatgg tgatcccct ggccagtgca cgtctgctgt cagataaagt      360
ctcccgtgaa ctttacccgg tggtgcatat cggggatgaa agctggcgca tgatgaccac    420
cgatatggcc agtgtgccag tctccgttat cggggaagaa gtggctgatc tcagccaccg    480
cgaaaatgac atcaaaaacg ccattaacct gatgttctgg ggaatataac ggccggagga    540
gtcactgact aagagctcct aagtgcaggg tctcaggcct aaattagctg caggctaaac     600
ctgcatttcg cgtaagactc aagtcttata actacgtaag gatcctaagt ttaaacagcc    660
cgggcattta atcagcgat cgcaaggtac cgctgagcaa taactagcat aaccccttgg      720
ggcctctaaa cgggtcttga ggggtttttt gctgaaagct tgaattctta gaaaaactca    780
tcgagcatca aatgaaactg caatttattc atatcaggat tatcaatacc atattttga     840 aaaagccgtt tctgtaatga aggagaaaac tcaccgaggc agttccatag gatggcaaga    900
tcctggtatc ggtctgcgat tccgactcgt ccaacatcaa tacaacctat taatttcccc    960
tcgtcaaaaa taaggttatc aagtgagaaa tcaccatgag tgacgactga atccggtgag    1020
aatggcaaaa gcttatgcat ttctttccag acttgttcaa caggccagcc attacgctcg    1080
tcatcaaaat cactcgcatc aaccaaaccg ttattcattc gtgattgcgc ctgagcgaga    1140
cgaaatacgc ggtcgctgtt aaaaggacaa ttacaaacag gaatcgaatg caaccggcgc    1200
```

```
aggaacactg ccagcgcatc aacaatattt tcacctgaat caggatattc ttctaatacc   1260
tggaatgctg ttttcccggg gatcgcagtg gtgagtaacc atgcatcatc aggagtacgg   1320
ataaaatgct tgatggtcgg aagaggcata aattccgtca gccagtttag tctgaccatc   1380
tcatctgtaa catcattggc aacgctacct ttgccatgtt tcagaaacaa ctctggcgca   1440
tcgggcttcc catacaatcg atagattgtc gcacctgatt gcccgacatt atcgcgagcc   1500
catttatacc catataaatc agcatccatg ttggaattta atcgcggcct cgagcaagac   1560
gtttcccgtt gaatatggct cataacaccc cttgtattac tgtttatgta agcagacagt   1620
tttattgttc atgaccaaaa tcccttaacg tgagttttcg ttccactgag cgtcagaccc   1680
cgtagaaaag atcaaaggat cttcttgaga tcctttttt ctgcgcgtaa tctgctgctt   1740
gcaaacaaaa aaaccaccgc taccagcggt ggtttgtttg ccggatcaag agctaccaac   1800 tcttttccg aaggtaactg gcttcagcag agcgcagata ccaaatactg tccttctagt   1860
gtagccgtag ttaggccacc acttcaagaa ctctgtagca ccgcctacat acctcgctct   1920
gctaatcctg ttaccagtgg ctgctgccag tggcgataag tcgtgtctta ccgggttgga   1980
ctcaagacga tagttaccgg ataaggcgca gcggtcgggc tgaacggggg gttcgtgcac   2040
acagcccagc ttggagcgaa cgacctacac cgaactgaga tacctacagc gtgagctatg   2100
agaaagcgcc acgcttcccg aagggagaaa ggcggacagg tatccggtaa gcggcagggt   2160
cggaacagga gagcgcacga gggagcttcc agggggaaac gcctggtatc tttatagtcc   2220
tgtcgggttt cgccacctct gacttgagcg tcgatttttg tgatgctcgt cagggggggcg   2280 gagcctatgg aaaaacgcca gcaacgcggc ctttttacgg ttcctggcct tttgctggcc   2340
ttttgctcac atgctctttc ctgcgttatc ccctgattct gtggataacc gtattaccgc   2400
ctttgagtga gctgataccg ctcgccgcag ccgaacgacc gagcgcagcg agtcagtgag   2460
cgaggaagcg gaagagcgcc tgatgcggta ttttctcctt acgcatctgt gcggtatttc   2520
acaccgcata tatggtgcac tctcagtaca atctgctctg atgccgcata gttaagccag   2580
tatacactcc gctatcgcta cgtgactggg tcatggctgc gccccgacac ccgccaacac   2640
ccgctgacgc gccctgacgg gcttgtctgc tcccggcatc cgcttacaga caagctgtga   2700
ccgtctccgg gagctgcatg tgtcagaggt tttcaccgtc atcaccgaaa cgcgcgaggc   2760
agctgcggta aagctcatca gcgtggtcgt gaagcgattc acagatgtct gcctgttcat   2820
ccgcgtccag ctcgttgagt ttctccagaa gcgttaatgt ctggcttctg ataaagcggg   2880
ccatgttaag gcggtttttt cctgtttggg tcactgatgc ctccgtgtaa gggggatttc   2940
tgttcatggg ggtaatgata ccgatgaaac gagagaggat gctcacgata cgggttactg   3000
atgatgaaca tgcccggtta ctggaacgtt gtgagggtaa acaactggcg gtatggatgc   3060
ggcgggacca gagaaaaatc accctaggtc actgcccgct ttccagtcgg gaaacctgtc   3120
gtgccagctg cattaatgaa tcggccaacg cgcggggaga ggcggtttgc gtattgggcg   3180
ccagggtggt ttttctttc accagtgaga cgggcaacag ctgattgccc ttcaccgcct   3240
ggccctgaga gagttgcagc aagcggtcca cgctggtttg ccccagcagg cgaaaatcct   3300
gtttgatggt ggttaacggc gggatataac atgagctgtc ttcggtatcg tcgtatccca   3360
ctaccgagat atccgcacca acgcgcagcc cggactcggt aatggcgcgc attgcgccca   3420
gcgccatctg atcgttggca accagcatcg cagtgggaac gatgccctca ttcagcattt   3480
gcatggtttg ttgaaaaccg gacatggcac tccagtcgcc ttcccgttcc gctatcggct   3540
gaatttgatt gcgagtgaga tatttatgcc agccagccag acgcagacgc gccgagacag   3600
```

```
aacttaatgg gcccgctaac agcgcgattt gctggtgacc caatgcgacc agatgctcca    3660
cgcccagtcg cgtaccgtct tcatgggaga aaataatact gttgatgggt gtctggtcag    3720
agacatcaag aaataacgcc ggaacattag tgcaggcagc ttccacagca atggcatcct    3780
ggtcatccag cggatagtta atgatcagcc cactgacgcg ttgcgcgaga agattgtgca    3840
ccgccgcttt acaggcttcg acgccgcttc gttctaccat cgacaccacc acgctggcac    3900
ccagttgatc ggcgcgagat taatcgccg cgacaatttg cgacggcgcg tgcagggcca    3960
gactggaggt ggcaacgcca atcagcaacg actgtttgcc cgccagttgt tgtgccacgc    4020
ggttgggaat gtaattcagc tccgccatcg ccgcttccac tttttcccgc gttttcgcag    4080
aaacgtggct ggcctggttc accacgcggg aaacggtctg ataagagaca ccggcatact    4140
ctgcgacatc gtataacgtt actggtttca tgatatatct ccttaattga ctctcttccc    4200
gggcgctatc atgccatacc gcgaaaggtt ttgcgccatt cgatggtgta gatctcaaat    4260
aaaacgaaag gctcagtcga aagactgggc ctttcgtttt atctgttgtt tgtcggtgaa    4320
cgctctcctg agtaggacaa atccgccggg agcggatttg aacgttgcga agcaacggcc    4380
cggagggtgg cgggcaggac gcccgccata aactgccagg catcaaatta agcagaaggc    4440
catcctgacg gatggccttt tgcgtttct acaaactctt ccgtaccgcg gttgtgtgga    4500
attgtgagcg gataacaatt tcacacagaa acagctccct c                       4541

<210> SEQ ID NO 66
<211> LENGTH: 4363
<212> TYPE: DNA
<213> ORGANISM: Artificial Sequence
<220> FEATURE:
<223> OTHER INFORMATION: Synthetic sequence

<400> SEQUENCE: 66
gtacgaaatt aatacgactc actataggga attgtgagcg ctcacaattc tctagaaata     60
attttgttta actttaagaa ggagatatac catggagacc ggtaaaatac ataaggctta    120
ctaaaagcca gataacagta tgcgtatttg cgcgctgatt tttgcggtat aagaatatat    180
actgatatct atacccgaag tatgtcaaaa agaggtgtgc tatgcagttt aaggtttaca    240
cctataaaag agagagccgt tatcgtctgt tgtggatgt acagagtgat attattgaca    300
cgcctgggcg acgcatggtg atccccctgg ccagtgcacg tctgctgtca gataaagtct    360
cccgtgaact ttacccggtg gtgcatatcg gggatgaaag ctggcgcatg atgaccaccg    420
atatggccag tgtgccagtc tccgttatcg gggaagaagt ggctgatctc agccaccgcg    480
aaaatgacat caaaaacgcc attaacctga tgttctgggg aatataacgg ccggtctcca    540
gtggacatca ccaccatcat cactaaggta ccgctgagca ataactagca taacccttg    600 gggcctctaa acgggtcttg agggggtttt tgctgaaagc ttgaattctt agaaaaactc    660
atcgagcatc aaatgaaact gcaatttatt catatcagga ttatcaatac catattttg    720 aaaaagccgt ttctgtaatg aaggagaaaa ctcaccgagg cagttccata ggatggcaag    780
atcctggtat cggtctgcga ttccgactcg tccaacatca atacaaccta ttaatttccc    840
ctcgtcaaaa ataaggttat caagtgagaa atcaccatga gtgacgactg aatccggtga    900
gaatggcaaa agcttatgca tttctttcca gacttgttca acaggccagc cattacgctc    960
gtcatcaaaa tcactcgcat caaccaaacc gttattcatt cgtgattgcg cctgagcgag   1020
acgaaatacg cggtcgctgt taaaaggaca attacaaaca ggaatcgaat gcaaccggcg   1080
```

```
caggaacact gccagcgcat caacaatatt ttcacctgaa tcaggatatt cttctaatac    1140
ctggaatgct gttttcccgg ggatcgcagt ggtgagtaac catgcatcat caggagtacg    1200
gataaaatgc ttgatggtcg gaagaggcat aaattccgtc agccagttta gtctgaccat    1260
ctcatctgta acatcattgg caacgctacc tttgccatgt ttcagaaaca actctggcgc    1320
atcgggcttc ccatacaatc gatagattgt cgcacctgat tgcccgacat tatcgcgagc    1380
ccatttatac ccatataaat cagcatccat gttggaattt aatcgcggcc tcgagcaaga    1440
cgtttcccgt tgaatatggc tcataacacc ccttgtatta ctgtttatgt aagcagacag    1500
ttttattgtt catgaccaaa atcccttaac gtgagttttc gttccactga gcgtcagacc    1560
ccgtagaaaa gatcaaagga tcttcttgag atcctttttt tctgcgcgta atctgctgct    1620
tgcaaacaaa aaaaccaccg ctaccagcgg tggtttgttt gccggatcaa gagctaccaa    1680 ctcttttttcc gaaggtaact ggcttcagca gagcgcagat accaaatact gtccttctag    1740
tgtagccgta gttaggccac cacttcaaga actctgtagc accgcctaca tacctcgctc    1800
tgctaatcct gttaccagtg gctgctgcca gtggcgataa gtcgtgtctt accgggttgg    1860
actcaagacg atagttaccg gataaggcgc agcggtcggg ctgaacgggg ggttcgtgca    1920
cacagcccag cttggagcga acgacctaca ccgaactgag atacctacag cgtgagctat    1980
gagaaagcgc cacgcttccc gaagggagaa aggcggacag gtatccggta agcggcaggg    2040
tcggaacagg agagcgcacg agggagcttc caggggggaaa cgcctggtat ctttatagtc    2100
ctgtcgggtt tcgccacctc tgacttgagc gtcgattttt gtgatgctcg tcagggggggc    2160 ggagcctatg gaaaaacgcc agcaacgcgg cctttttacg gttcctggcc ttttgctggc    2220
cttttgctca catgctcttt cctgcgttat cccctgattc tgtggataac cgtattaccg    2280
cctttgagtg agctgatacc gctcgccgca gccgaacgac cgagcgcagc gagtcagtga    2340
gcgaggaagc ggaagagcgc ctgatgcggt attttctcct tacgcatctg tgcggtattt    2400
cacaccgcat atatggtgca ctctcagtac aatctgctct gatgccgcat agttaagcca    2460
gtatacactc cgctatcgct acgtgactgg gtcatggctg cgccccgaca cccgccaaca    2520
cccgctgacg cgccctgacg ggcttgtctg ctcccggcat ccgcttacag acaagctgtg    2580
accgtctccg ggagctgcat gtgtcagagg ttttcaccgt catcaccgaa acgcgcgagg    2640
cagctgcggt aaagctcatc agcgtggtcg tgaagcgatt cacagatgtc tgcctgttca    2700
tccgcgtcca gctcgttgag tttctccaga agcgttaatg tctggcttct gataaagcgg    2760
gccatgttaa gggcggtttt ttcctgtttg gtcactgatg cctccgtgta agggggattt    2820
ctgttcatgg gggtaatgat accgatgaaa cgagagagga tgctcacgat acgggttact    2880
gatgatgaac atgcccggtt actggaacgt tgtgagggta acaactggc ggtatggatg     2940 cggcgggacc agagaaaaat caccctaggt cactgcccgc tttccagtcg ggaaacctgt    3000
cgtgccagct gcattaatga atcggccaac gcgcggggag aggcggtttg cgtattgggc    3060
gccagggtgg ttttctttt caccagtgag acggcaacag ctgattgcc cttcaccgcc      3120 tggccctgag agagttgcag caagcggtcc acgctggttt gccccagcag gcgaaaatcc    3180
tgtttgatgg tggttaacgg cgggatataa catgagctgt cttcggtatc gtcgtatccc    3240
actaccgaga tatccgcacc aacgcgcagc ccggactcgg taatggcgcg cattgcgccc    3300
agcgccatct gatcgttggc aaccagcatc gcagtgggaa cgatgccctc attcagcatt    3360
tgcatggttt gttgaaaacc ggacatggca ctccagtcgc cttcccgttc cgctatcggc    3420
tgaatttgat tgcgagtgag atatttatgc cagccagcca gacgcagacg cgccgagaca    3480
```

```
gaacttaatg ggcccgctaa cagcgcgatt tgctggtgac ccaatgcgac cagatgctcc    3540
acgcccagtc gcgtaccgtc ttcatgggag aaaataatac tgttgatggg tgtctggtca    3600
gagacatcaa gaataacgc cggaacatta gtgcaggcag cttccacagc aatggcatcc    3660
tggtcatcca gcggatagtt aatgatcagc ccactgacgc gttgcgcgag aagattgtgc    3720
accgccgctt tacaggcttc gacgccgctt cgttctacca tcgacaccac cacgctggca    3780
cccagttgat cggcgcgaga tttaatcgcc gcgacaattt gcgacggcgc gtgcagggcc    3840
agactggagg tggcaacgcc aatcagcaac gactgtttgc ccgccagttg ttgtgccacg    3900
cggttgggaa tgtaattcag ctccgccatc gccgcttcca cttttcccg cgttttcgca    3960 gaaacgtggc tggcctggtt caccacgcgg aaacggtct gataagagac accggcatac    4020
tctgcgacat cgtataacgt tactggtttc atgatatatc tccttaattg actctcttcc    4080
cgggcgctat catgccatac cgcgaaaggt tttgcgccat tcgatggtgt agatctcaaa    4140
taaaacgaaa ggctcagtcg aaagactggg cctttcgttt tatctgttgt ttgtcggtga    4200
acgctctcct gagtaggaca aatccgccgg agcggatttt gaacgttgcg aagcaacggc    4260
ccggagggtg gcgggcagga cgcccgccat aaactgccag gcatcaaatt aagcagaagg    4320
ccatcctgac ggatggcctt tttgcgtttc tacaaactct tcc                      4363
```

<210> SEQ ID NO 67
<211> LENGTH: 4362
<212> TYPE: DNA
<213> ORGANISM: Artificial Sequence
<220> FEATURE:
<223> OTHER INFORMATION: Synthetic sequence

<400> SEQUENCE: 67

```
gtacgaaatt aatacgactc actataggaa ttgtgagcgc tcacaattct ctagaaataa      60
ttttgtttaa ctttaagaag gagatatacc atggagaccg gtaaaataca taaggcttac    120
taaaagccag ataacagtat gcgtatttgc gcgctgattt ttgcggtata agaatatata    180
ctgatatcta tacccgaagt atgtcaaaaa gaggtgtgct atgcagttta aggtttacac    240
ctataaaaga gagagccgtt atcgtctgtt tgtggatgta cagagtgata ttattgacac    300
gcctgggcga cgcatggtga tcccctggc cagtgcacgt ctgctgtcag ataaagtctc    360
ccgtgaactt tacccggtgg tgcatatcgg ggatgaaagc tggcgcatga tgaccaccga    420
tatggccagt gtgccagtct ccgttatcgg ggaagaagtg gctgatctca gccaccgcga    480
aaatgacatc aaaaacgcca ttaacctgat gttctgggga atataacggc cggtctccag    540
tggacatcac caccatcatc actaaggtac cgctgagcaa taactagcat aacccttgg     600 ggcctctaaa cgggtcttga gggtttttt gctgaaagct tgaattctta gaaaactca     660 tcgagcatca aatgaaactg caatttattc atatcaggat tatcaatacc atattttga    720 aaaagccgtt tctgtaatga aggagaaaac tcaccgagc agttccatag gatggcaaga    780
tcctggtatc ggtctgcgat tccgactcgt ccaacatcaa tacaacctat taatttcccc    840
tcgtcaaaaa taaggttatc aagtgagaaa tcaccatgag tgacgactga atccggtgag    900
aatggcaaaa gcttatgcat ttcttccag acttgttcaa caggccagcc attacgctcg    960
tcatcaaaat cactcgcatc aaccaaaccg ttattcattc gtgattgcgc ctgagcgaga   1020
cgaaatacgc ggtcgctgtt aaaaggacaa ttacaaacag gaatcgaatg caaccggcgc   1080
aggaacactg ccagcgcatc aacaatattt tcacctgaat caggatattc ttctaatacc   1140
```

```
tggaatgctg ttttcccggg gatcgcagtg gtgagtaacc atgcatcatc aggagtacgg      1200
ataaaatgct tgatggtcgg aagaggcata aattccgtca gccagtttag tctgaccatc      1260
tcatctgtaa catcattggc aacgctacct tgccatgtt tcagaaacaa ctctggcgca       1320
tcgggcttcc catacaatcg atagattgtc gcacctgatt gcccgacatt atcgcgagcc      1380
catttatacc catataaatc agcatccatg ttggaattta atcgcggcct cgagcaagac      1440
gtttcccgtt gaatatggct cataacaccc cttgtattac tgtttatgta agcagacagt      1500
tttattgttc atgaccaaaa tcccttaacg tgagttttcg ttccactgag cgtcagaccc      1560
cgtagaaaag atcaaaggat cttcttgaga tcctttttt ctgcgcgtaa tctgctgctt       1620
gcaaacaaaa aaccaccgc taccagcggt ggtttgtttg ccggatcaag agctaccaac      1680 tcttttccg aaggtaactg gcttcagcag agcgcagata ccaaatactg tccttctagt       1740
gtagccgtag ttaggccacc acttcaagaa ctctgtagca ccgcctacat acctcgctct      1800
gctaatcctg ttaccagtgg ctgctgccag tggcgataag tcgtgtctta ccgggttgga     1860
ctcaagacga tagttaccgg ataaggcgca gcggtcgggc tgaacggggg gttcgtgcac      1920
acagcccagc ttggagcgaa cgacctacac cgaactgaga tacctacagc gtgagctatg     1980
agaaagcgcc acgcttcccg aagggagaaa ggcggacagg tatccggtaa gcggcagggt    2040
cggaacagga gagcgcacga gggagcttcc aggggggaaac gcctggtatc tttatagtcc   2100
tgtcgggttt cgccacctct gacttgagcg tcgattttg tgatgctcgt caggggggcg      2160
gagcctatgg aaaaacgcca gcaacgcggc cttttacgg ttcctggcct tttgctggcc     2220
ttttgctcac atgctctttc ctgcgttatc ccctgattct gtggataacc gtattaccgc    2280
ctttgagtga gctgataccg ctcgccgcag ccgaacgacc gagcgcagcg agtcagtgag    2340
cgaggaagcg gaagagcgcc tgatgcggta ttttctcctt acgcatctgt gcggtatttc    2400
acaccgcata tatggtgcac tctcagtaca atctgctctg atgccgcata gttaagccag    2460
tatacactcc gctatcgcta cgtgactggg tcatggctgc gccccgacac ccgccaacac   2520
ccgctgacgc gccctgacgg gcttgtctgc tcccggcatc cgcttacaga caagctgtga   2580
ccgtctccgg gagctgcatg tgtcagaggt tttcaccgtc atcaccgaaa cgcgcgaggc  2640
agctgcggta aagctcatca gcgtggtcgt gaagcgattc acagatgtct gcctgttcat   2700
ccgcgtccag ctcgttgagt ttctccagaa gcgttaatgt ctggcttctg ataaagcggg   2760
ccatgttaag gcggttttt cctgtttgg tcactgatgc ctccgtgtaa gggggatttc     2820
tgttcatggg ggtaatgata ccgatgaaac gagagaggat gctcacgata cgggttactg   2880
atgatgaaca tgcccggtta ctggaacgtt gtgagggtaa acaactggcg gtatggatgc    2940
ggcgggacca gagaaaaatc accctaggtc actgcccgct ttccagtcgg gaaacctgtc   3000
gtgccagctg cattaatgaa tcggccaacg cgcggggaga ggcggtttgc gtattgggcg   3060
ccagggtggt ttttcttttc accagtgaga cgggcaacag ctgattgccc ttcaccgcct   3120
ggccctgaga gagttgcagc aagcggtcca cgctggtttg ccccagcagg cgaaaatcct   3180
gtttgatggt ggttaacggc gggatataac atgagctgtc ttcggtatcg tcgtatccca   3240
ctaccgagat atccgcacca acgcgcagcc cggactcggt aatggcgcgc attgcgccca   3300
gcgccatctg atcgttggca accagcatcg cagtgggaac gatgccctca ttcagcattt   3360
gcatggtttg ttgaaaaccg gacatggcac tccagtcgcc ttcccgttcc gctatcggct   3420
gaatttgatt gcgagtgaga tatttatgcc agccagccag acgcagacgc gccgagacag   3480
aacttaatgg gcccgctaac agcgcgattt gctggtgacc caatgcgacc agatgctcca   3540
```

```
cgcccagtcg cgtaccgtct tcatgggaga aaataatact gttgatgggt gtctggtcag    3600
agacatcaag aaataacgcc ggaacattag tgcaggcagc ttccacagca atggcatcct    3660
ggtcatccag cggatagtta atgatcagcc cactgacgcg ttgcgcgaga agattgtgca    3720
ccgccgcttt acaggcttcg acgccgcttc gttctaccat cgacaccacc acgctggcac    3780
ccagttgatc ggcgcgagat taatcgccg cgacaatttg cgacggcgcg tgcagggcca    3840
gactggaggt ggcaacgcca atcagcaacg actgtttgcc cgccagttgt tgtgccacgc    3900
ggttgggaat gtaattcagc tccgccatcg ccgcttccac ttttcccgc gttttcgcag     3960 aaacgtggct ggcctggttc accacgcggg aaacggtctg ataagagaca ccggcatact    4020
ctgcgacatc gtataacgtt actggtttca tgatatatct ccttaattga ctctcttccc    4080
gggcgctatc atgccatacc gcgaaaggtt ttgcgccatt cgatggtgta gatctcaaat    4140
aaaacgaaag gctcagtcga aagactgggc ctttcgtttt atctgttgtt tgtcggtgaa    4200
cgctctcctg agtaggacaa atccgccggg agcggatttg aacgttgcga agcaacggcc    4260
cggagggtgg cgggcaggac gcccgccata aactgccagg catcaaatta agcagaaggc    4320
catcctgacg gatggccttt ttgcgtttct acaaactctt cc                       4362
```

<210> SEQ ID NO 68
<211> LENGTH: 4422
<212> TYPE: DNA
<213> ORGANISM: Artificial Sequence
<220> FEATURE:
<223> OTHER INFORMATION: Synthetic sequence

<400> SEQUENCE: 68

```
gtacgaaatt aatacgactc actataggga attgtgagcg ctcacaattc tctagaaata     60
attttgttta actttaagaa ggagatatac catggagacc ggtaaaatac ataaggctta    120
ctaaaagcca gataacagta tgcgtatttg cgcgctgatt tttgcggtat aagaatatat    180
actgatatct atcccgaag tatgtcaaaa agaggtgtgc tatgcagttt aaggtttaca    240
cctataaaag agagagccgt tatcgtctgt ttgtggatgt acagagtgat attattgaca    300
cgcctgggcg acgcatggtg atcccccgg ccagtgcacg tctgctgtca gataaagtct    360
cccgtgaact ttaccggtg gtgcatatcg gggatgaaag ctggcgcatg atgaccaccg    420
atatggccag tgtgccagtc tccgttatcg gggaagaagt ggctgatctc agccaccgcg    480
aaaatgacat caaaaacgcc attaacctga tgttctgggg aatataacgg ccggtctcca    540
gtggacatca ccaccatcat cactaaggta ccgctgagca ataactagca taaccccttg    600
gggcctctaa acgggtcttg aggggttttt tgctgaaagc ttgaattctt agaaaaactc    660
atcgagcatc aaatgaaact gcaatttatt catatcagga ttatcaatac catattttg    720 aaaaagccgt ttctgtaatg aaggagaaaa ctcaccgagg cagttccata ggatggcaag    780
atcctggtat cggtctgcga ttccgactcg tccaacatca atacaaccta ttaatttccc    840
ctcgtcaaaa ataaggttat caagtgagaa atcaccatga gtgacgactg aatccggtga    900
gaatggcaaa agcttatgca tttctttcca gacttgttca acaggccagc cattacgctc    960
gtcatcaaaa tcactcgcat caaccaaacc gttattcatt cgtgattgcg cctgagcgag   1020
acgaaatacg cggtcgctgt taaaaggaca attacaaaca ggaatcgaat gcaaccggcg   1080
caggaacact gccagcgcat caacaatatt ttcacctgaa tcaggatatt cttctaatac   1140
ctggaatgct gttttcccgg ggatcgcagt ggtgagtaac catgcatcat caggagtacg   1200
```

```
gataaaatgc ttgatggtcg gaagaggcat aaattccgtc agccagttta gtctgaccat    1260
ctcatctgta acatcattgg caacgctacc tttgccatgt ttcagaaaca actctggcgc    1320
atcgggcttc ccatacaatc gatagattgt cgcacctgat tgcccgacat tatcgcgagc    1380
ccatttatac ccatataaat cagcatccat gttggaattt aatcgcggcc tcgagcaaga    1440
cgtttcccgt tgaatatggc tcataacacc ccttgtatta ctgtttatgt aagcagacag    1500
ttttattgtt catgaccaaa atcccttaac gtgagttttc gttccactga gcgtcagacc    1560
ccgtagaaaa gatcaaagga tcttcttgag atcctttttt tctgcgcgta atctgctgct    1620
tgcaaacaaa aaaaccaccg ctaccagcgg tggtttgttt gccggatcaa gagctaccaa    1680 ctcttttttcc gaaggtaact ggcttcagca gagcgcagat accaaatact gtccttctag    1740
tgtagccgta gttaggccac cacttcaaga actctgtagc accgcctaca tacctcgctc    1800
tgctaatcct gttaccagtg ctgctgcca gtggcgataa gtcgtgtctt accgggttgg    1860
actcaagacg atagttaccg gataaggcgc agcggtcggg ctgaacgggg ggttcgtgca    1920
cacagcccag cttggagcga acgacctaca ccgaactgag atacctacag cgtgagctat    1980
gagaaagcgc cacgcttccc gaagggagaa aggcggacag gtatccggta agcggcaggg    2040
tcggaacagg agagcgcacg agggagcttc caggggggaaa cgcctggtat ctttatagtc    2100
ctgtcgggtt tcgccacctc tgacttgagc gtcgattttt gtgatgctcg tcaggggggc    2160
ggagcctatg gaaaaacgcc agcaacgcgg cctttttacg gttcctggcc ttttgctggc    2220
cttttgctca catgctcttt cctgcgttat ccctgattc tgtggataac cgtattaccg    2280
cctttgagtg agctgatacc gctcgccgca gccgaacgac cgagcgcagc gagtcagtga    2340
gcgaggaagc ggaagagcgc ctgatgcggt attttctcct tacgcatctg tgcggtattt    2400
cacaccgcat atatggtgca ctctcagtac aatctgctct gatgccgcat agttaagcca    2460
gtatacactc cgctatcgct acgtgactgg gtcatggctg cgccccgaca cccgccaaca    2520
cccgctgacg cgccctgacg ggcttgtctg ctcccggcat ccgcttacag acaagctgtg    2580
accgtctccg ggagctgcat gtgtcagagg ttttcaccgt catcaccgaa acgcgcgagg    2640
cagctgcggt aaagctcatc agcgtggtcg tgaagcgatt cacagatgtc tgcctgttca    2700
tccgcgtcca gctcgttgag tttctccaga agcgttaatg tctggcttct gataaagcgg    2760
gccatgttaa gggcggtttt ttcctgtttg gtcactgatg cctccgtgta agggggattt    2820
ctgttcatgg gggtaatgat accgatgaaa cgagagagga tgctcacgat acgggttact    2880
gatgatgaac atgcccggtt actggaacgt tgtgagggta acaactggc ggtatggatg    2940 cggcgggacc agagaaaaat caccctaggt cactgcccgc tttccagtcg ggaaacctgt    3000
cgtgccagct gcattaatga atcggccaac gcgcggggag aggcggtttg cgtattgggc    3060
gccagggtgg ttttcttttt caccagtgag acggcaaca gctgattgcc cttcaccgcc    3120
tggccctgag agagttgcag caagcggtcc acgctggttt gccccagcag gcgaaaatcc    3180
tgtttgatgg tggttaacgg cgggatataa catgagctgt cttcggtatc gtcgtatccc    3240
actaccgaga tatccgcacc aacgcgcagc ccggactcgg taatggcgcg cattgcgccc    3300
agcgccatct gatcgttggc aaccagcatc gcagtgggaa cgatgccctc attcagcatt    3360
tgcatggttt gttgaaaacc ggacatggca ctccagtcgc cttcccgttc cgctatcggc    3420
tgaatttgat tgcgagtgag atatttatgc cagccagcca gacgcagacg cgccgagaca    3480
gaacttaatg ggcccgctaa cagcgcgatt tgctggtgac ccaatgcgac cagatgctcc    3540
acgcccagtc gcgtaccgtc ttcatgggag aaaataatac tgttgatggg tgtctggtca    3600
```

```
gagacatcaa gaaataacgc cggaacatta gtgcaggcag cttccacagc aatggcatcc    3660
tggtcatcca gcggatagtt aatgatcagc ccactgacgc gttgcgcgag aagattgtgc    3720
accgccgctt tacaggcttc gacgccgctt cgttctacca tcgacaccac cacgctggca    3780
cccagttgat cggcgcgaga tttaatcgcc gcgacaattt gcgacggcgc gtgcagggcc    3840
agactggagg tggcaacgcc aatcagcaac gactgtttgc ccgccagttg ttgtgccacg    3900
cggttgggaa tgtaattcag ctccgccatc gccgcttcca cttttttccg cgttttcgca    3960
gaaacgtggc tggcctggtt caccacgcgg gaaacggtct gataagagac accggcatac    4020
tctgcgacat cgtataacgt tactggtttc atgatatatc tccttaattg actctcttcc    4080
cgggcgctat catgccatac cgcgaaaggt tttgcgccat tcgatggtgt agatctcaaa    4140
taaaacgaaa ggctcagtcg aaagactggg cctttcgttt tatctgttgt ttgtcggtga    4200
acgctctcct gagtaggaca atccgccgg gagcggattt gaacgttgcg aagcaacggc    4260
ccggagggtg gcgggcagga cgcccgccat aaactgccag gcatcaaatt aagcagaagg    4320
ccatcctgac ggatggcctt tttgcgtttc tacaaactct tccgtaccgc ggttgtgtgg    4380
aattgtgagc ggataacaat ttcacacaga aacagctccc tc                       4422
```

<210> SEQ ID NO 69
<211> LENGTH: 4421
<212> TYPE: DNA
<213> ORGANISM: Artificial Sequence
<220> FEATURE:
<223> OTHER INFORMATION: Synthetic sequence

<400> SEQUENCE: 69

```
gtacgaaatt aatacgactc actataggaa ttgtgagcgc tcacaattct ctagaaataa      60
ttttgtttaa cttaagaag gagatatacc atggagaccg gtaaaataca taaggcttac     120
taaaagccag ataacagtat gcgtatttgc gcgctgattt ttgcggtata agaatatata    180
ctgatatcta tacccgaagt atgtcaaaaa gaggtgtgct atgcagttta aggtttacac    240
ctataaaaga gagagccgtt atcgtctgtt tgtggatgta cagagtgata ttattgacac    300
gcctgggcga cgcatggtga tcccctggc cagtgcacgt ctgctgtcag ataaagtctc    360
ccgtgaactt tacccggtgg tgcatatcgg ggatgaaagc tggcgcatga tgaccaccga    420
tatggccagt gtgccagtct ccgttatcgg ggaagaagtg gctgatctca gccaccgcga    480
aaatgacatc aaaaacgcca ttaacctgat gttctgggga atataacggc cggtctccag    540
tggacatcac caccatcatc actaaggtac cgctgagcaa taactagcat aaccccttgg    600
ggcctctaaa cgggtcttga ggggtttttt gctgaaagct tgaattctta gaaaaactca    660
tcgagcatca aatgaaactg caatttattc atatcaggat tatcaatacc atattttga    720 aaaagccgtt tctgtaatga aggagaaaac tcaccgaggc agttccatag gatggcaaga    780
tcctggtatc ggtctgcgat tccgactcgt ccaacatcaa taacctat taatttcccc      840 tcgtcaaaaa taaggttatc aagtgagaaa tcaccatgag tgacgactga atccggtgag    900
aatggcaaaa gcttatgcat ttcttccag acttgttcaa caggccagcc attacgctcg    960
tcatcaaaat cactcgcatc aaccaaaccg ttattcattc gtgattgcgc ctgagcgaga   1020
cgaaatacgc ggtcgctgtt aaaaggacaa ttacaaacag gaatcgaatg caaccggcgc   1080
aggaacactg ccagcgcatc aacaatattt tcacctgaat caggatattc ttctaatacc   1140
tggaatgctg ttttcccggg gatcgcagtg gtgagtaacc atgcatcatc aggagtacgg   1200
```

```
ataaaatgct tgatggtcgg aagaggcata aattccgtca gccagtttag tctgaccatc    1260
tcatctgtaa catcattggc aacgctacct ttgccatgtt tcagaaacaa ctctggcgca    1320
tcgggcttcc catacaatcg atagattgtc gcacctgatt gcccgacatt atcgcgagcc    1380
catttatacc catataaatc agcatccatg ttggaattta atcgcggcct cgagcaagac    1440
gtttcccgtt gaatatggct cataacaccc cttgtattac tgtttatgta agcagacagt    1500
tttattgttc atgaccaaaa tcccttaacg tgagttttcg ttccactgag cgtcagaccc    1560
cgtagaaaag atcaaaggat cttcttgaga tcctttttt ctgcgcgtaa tctgctgctt    1620
gcaaacaaaa aaaccaccgc taccagcggt ggtttgtttg ccggatcaag agctaccaac    1680 tcttttccg aaggtaactg gcttcagcag agcgcagata ccaaatactg tccttctagt    1740
gtagccgtag ttaggccacc acttcaagaa ctctgtagca ccgcctacat acctcgctct    1800
gctaatcctg ttaccagtgg ctgctgccag tggcgataag tcgtgtctta ccgggttgga    1860
ctcaagacga tagttaccgg ataaggcgca gcggtcgggc tgaacggggg gttcgtgcac    1920
acagcccagc ttggagcgaa cgacctacac cgaactgaga tacctacagc gtgagctatg    1980
agaaagcgcc acgcttcccg aagggagaaa ggcggacagg tatccggtaa gcggcagggt    2040
cggaacagga gagcgcacga gggagcttcc agggggaaac gcctggtatc tttatagtcc    2100
tgtcgggttt cgccacctct gacttgagcg tcgatttttg tgatgctcgt caggggggcg    2160
gagcctatgg aaaaacgcca gcaacgcggc cttttacgg ttcctggcct tttgctggcc    2220
ttttgctcac atgctctttc ctgcgttatc ccctgattct gtggataacc gtattaccgc    2280
ctttgagtga gctgataccg ctcgccgcag ccgaacgacc gagcgcagcg agtcagtgag    2340
cgaggaagcg gaagagcgcc tgatgcggta ttttctcctt acgcatctgt gcggtatttc    2400
acaccgcata tatggtgcac tctcagtaca atctgctctg atgccgcata gttaagccag    2460
tatacactcc gctatcgcta cgtgactggg tcatggctgc gccccgacac ccgccaacac    2520
ccgctgacgc gccctgacgg gcttgtctgc tcccggcatc cgcttacaga caagctgtga    2580
ccgtctccgg gagctgcatg tgtcagaggt tttcaccgtc atcaccgaaa cgcgcgaggc    2640
agctgcggta aagctcatca gcgtggtcgt gaagcgattc acagatgtct gcctgttcat    2700
ccgcgtccag ctcgttgagt ttctccagaa gcgttaatgt ctggcttctg ataaagcggg    2760
ccatgttaag gcggttttt tcctgtttgg tcactgatgc ctccgtgtaa ggggatttc    2820 tgttcatggg ggtaatgata ccgatgaaac gagagaggat gctcacgata cgggttactg    2880
atgatgaaca tgcccggtta ctggaacgtt gtgagggtaa acaactggcg gtatggatgc    2940
ggcgggacca gagaaaaatc accctaggtc actgcccgct ttccagtcgg gaaacctgtc    3000
gtgccagctg cattaatgaa tcggccaacg cgcggggaga gcggtttgc gtattgggcg    3060 ccagggtggt ttttctttc accagtgaga cgggcaacag ctgattgccc ttcaccgcct    3120
ggccctgaga gagttgcagc aagcggtcca gctggtttg ccccagcagg cgaaaatcct    3180
gtttgatggt ggttaacggc gggatataac atgagctgtc ttcggtatcg tcgtatccca    3240
ctaccgagat atccgcacca acgcgcagcc cggactcggt aatggcgcgc attgcgccca    3300
gcgccatctg atcgttggca accagcatcg cagtgggaac gatgccctca ttcagcattt    3360
gcatggtttg ttgaaaaccg gacatggcac tccagtcgcc ttcccgttcc gctatcggct    3420
gaatttgatt gcgagtgaga tatttatgcc agccagccag acgcagacgc gccgagacag    3480
aacttaatgg gcccgctaac agcgcgattt gctggtgacc caatgcgacc agatgctcca    3540
cgcccagtcg cgtaccgtct tcatgggaga aaataatact gttgatgggt gtctggtcag    3600
```

| | |
|---|---|
| agacatcaag aaataacgcc ggaacattag tgcaggcagc ttccacagca atggcatcct | 3660 |
| ggtcatccag cggatagtta atgatcagcc cactgacgcg ttgcgcgaga agattgtgca | 3720 |
| ccgccgcttt acaggcttcg acgccgcttc gttctaccat cgacaccacc acgctggcac | 3780 |
| ccagttgatc ggcgcgagat taatcgccg cgacaatttg cgacggcgcg tgcagggcca | 3840 |
| gactggaggt ggcaacgcca atcagcaacg actgtttgcc cgccagttgt tgtgccacgc | 3900 |
| ggttgggaat gtaattcagc tccgccatcg ccgcttccac ttttccccgc gttttcgcag | 3960 |
| aaacgtggct ggcctggttc accacgcggg aaacggtctg ataagagaca ccggcatact | 4020 |
| ctgcgacatc gtaaacgtt actggtttca tgatatatct ccttaattga ctctcttccc | 4080 |
| gggcgctatc atgccatacc gcgaaaggtt ttgcgccatt cgatggtgta gatctcaaat | 4140 |
| aaaacgaaag gctcagtcga aagactgggc ctttcgtttt atctgttgtt tgtcggtgaa | 4200 |
| cgctctcctg agtaggacaa atccgccggg agcggatttg aacgttgcga agcaacggcc | 4260 |
| cggagggtgg cggcaggac gcccgccata aactgccagg catcaaatta agcagaaggc | 4320 |
| catcctgacg gatggcctt ttgcgtttct acaaactctt ccgtaccgcg gttgtgtgga | 4380 |
| attgtgagcg gataacaatt tcacacagaa acagctccct c | 4421 |

<210> SEQ ID NO 70
<211> LENGTH: 4343
<212> TYPE: DNA
<213> ORGANISM: Artificial Sequence
<220> FEATURE:
<223> OTHER INFORMATION: Synthetic sequence

<400> SEQUENCE: 70

| | |
|---|---|
| gtacgaaatt aatacgactc actataggga attgtgagcg ctcacaattc tctagaagaa | 60 |
| ggagatatac catggagacc ggtaaaatac ataaggctta ctaaaagcca gataacagta | 120 |
| tgcgtatttg cgcgctgatt tttgcggtat aagaatatat actgatatct atacccgaag | 180 |
| tatgtcaaaa agaggtgtgc tatgcagttt aaggtttaca cctataaaag agagagccgt | 240 |
| tatcgtctgt ttgtggatgt acagagtgat attattgaca cgcctgggcg acgcatggtg | 300 |
| atcccctgg ccagtgcacg tctgctgtca gataaagtct cccgtgaact ttaccggtg | 360 |
| gtgcatatcg gggatgaaag ctggcgcatg atgaccaccg atatggccag tgtgccagtc | 420 |
| tccgttatcg gggaagaagt ggctgatctc agccaccgcg aaaatgacat caaaaacgcc | 480 |
| attaacctga tgttctgggg aatataacgg ccggtctcca gtggacatca ccaccatcat | 540 |
| cactaaggta ccgctgagca ataactagca taaccccttg gggcctctaa acgggtcttg | 600 |
| aggggttttt tgctgaaagc ttgaattctt agaaaaactc atcgagcatc aaatgaaact | 660 |
| gcaatttatt catatcagga ttatcaatac catattttg aaaaagccgt ttctgtaatg | 720 |
| aaggagaaaa ctcaccgagg cagttccata ggatggcaag atcctggtat cggtctgcga | 780 |
| ttccgactcg tccaacatca atacaaccta ttaatttccc ctcgtcaaaa ataaggttat | 840 |
| caagtgagaa atcaccatga gtgacgactg aatccggtga gaatggcaaa agcttatgca | 900 |
| tttctttcca gacttgttca acaggccagc cattacgctc gtcatcaaaa tcactcgcat | 960 |
| caaccaaacc gttattcatt cgtgattgcg cctgagcgag acgaaatacg cggtcgctgt | 1020 |
| taaaaggaca attacaaaca ggaatcgaat gcaaccggcg caggaacact gccagcgcat | 1080 |
| caacaatatt ttcacctgaa tcaggatatt cttctaatac ctggaatgct gttttcccgg | 1140 |
| ggatcgcagt ggtgagtaac catgcatcat caggagtacg gataaaatgc ttgatggtcg | 1200 |

```
gaagaggcat aaattccgtc agccagttta gtctgaccat ctcatctgta acatcattgg    1260
caacgctacc tttgccatgt ttcagaaaca actctggcgc atcgggcttc ccatacaatc    1320
gatagattgt cgcacctgat tgcccgacat tatcgcgagc ccatttatac ccatataaat    1380
cagcatccat gttggaattt aatcgcggcc tcgagcaaga cgtttcccgt tgaatatggc    1440
tcataacacc ccttgtatta ctgtttatgt aagcagacag ttttattgtt catgaccaaa    1500
atcccttaac gtgagttttc gttccactga gcgtcagacc ccgtagaaaa gatcaaagga    1560
tcttcttgag atccttttt tctgcgcgta atctgctgct tgcaaacaaa aaaccaccg      1620
ctaccagcgg tggtttgttt gccggatcaa gagctaccaa ctcttttcc gaaggtaact     1680
ggcttcagca gagcgcagat accaaatact gtccttctag tgtagccgta gttaggccac    1740
cacttcaaga actctgtagc accgcctaca tacctcgctc tgctaatcct gttaccagtg    1800
gctgctgcca gtggcgataa gtcgtgtctt accgggttgg actcaagacg atagttaccg    1860
gataaggcgc agcggtcggg ctgaacgggg ggttcgtgca cacagcccag cttggagcga    1920
acgacctaca ccgaactgag atacctacag cgtgagctat gagaaagcgc cacgcttccc    1980
gaagggagaa aggcggacag gtatccggta agcggcaggg tcggaacagg agagcgcacg    2040
agggagcttc caggggggaaa cgcctggtat ctttatagtc ctgtcgggtt cgccacctc    2100
tgacttgagc gtcgatttt gtgatgctcg tcaggggggc ggagcctatg gaaaaacgcc     2160
agcaacgcgg cctttttacg gttcctggcc ttttgctggc cttttgctca catgctcttt    2220
cctgcgttat cccctgattc tgtggataac cgtattaccg cctttgagtg agctgatacc    2280
gctcgccgca gccgaacgac cgagcgcagc gagtcagtga gcgaggaagc ggaagagcgc    2340
ctgatgcggt attttctcct tacgcatctg tgcggtattt cacaccgcat atatggtgca    2400
ctctcagtac aatctgctct gatgccgcat agttaagcca gtatacactc cgctatcgct    2460
acgtgactgg gtcatggctg cgccccgaca cccgccaaca cccgctgacg cgccctgacg    2520
ggcttgtctg ctcccggcat ccgcttacag acaagctgtg accgtctccg ggagctgcat    2580
gtgtcagagg ttttcaccgt catcaccgaa acgcgcgagg cagctgcggt aaagctcatc    2640
agcgtggtcg tgaagcgatt cacagatgtc tgcctgttca tccgcgtcca gctcgttgag    2700
tttctccaga agcgttaatg tctggcttct gataaagcgg gccatgttaa gggcggtttt    2760
ttcctgtttg gtcactgatg cctccgtgta aggggggattt ctgttcatgg gggtaatgat    2820
accgatgaaa cgagagagga tgctcacgat acgggttact gatgatgaac atgcccggtt    2880
actggaacgt tgtgagggta acaactggcg gtatggatg cggcgggacc agagaaaaat     2940
cacccctaggt cactgcccgc tttccagtcg ggaaacctgt cgtgccagct gcattaatga    3000
atcggccaac gcgcggggag aggcggtttg cgtattgggc gccagggtgg ttttctttt     3060
caccagtgag acgggcaaca gctgattgcc cttcaccgcc tggccctgag agagttgcag    3120
caagcggtcc acgctggttt gccccagcag gcgaaaatcc tgtttgatgg tggttaacgg    3180
cgggatataa catgagctgt cttcggtatc gtcgtatccc actaccgaga tatccgcacc    3240
aacgcgcagc ccggactcgg taatggcgcg cattgcgccc agcgccatct gatcgttggc    3300
aaccagcatc gcagtgggaa cgatgccctc attcagcatt tgcatggttt gttgaaaacc    3360
ggacatggca ctccagtcgc cttcccgttc cgctatcggc tgaatttgat tgcgagtgag    3420
atatttatgc cagccagcca gacgcagacg cgccgagaca gaacttaatg ggcccgctaa    3480
cagcgcgatt tgctggtgac ccaatgcgac cagatgctcc acgcccagtc gcgtaccgtc    3540
ttcatgggag aaaataatac tgttgatggg tgtctggtca gagacatcaa gaaataacgc    3600
```

```
cggaacatta gtgcaggcag cttccacagc aatggcatcc tggtcatcca gcggatagtt    3660
aatgatcagc ccactgacgc gttgcgcgag aagattgtgc accgccgctt tacaggcttc    3720
gacgccgctt cgttctacca tcgacaccac cacgctggca cccagttgat cggcgcgaga    3780
tttaatcgcc gcgacaattt gcgacggcgc gtgcagggcc agactggagg tggcaacgcc    3840
aatcagcaac gactgtttgc ccgccagttg ttgtgccacg cggttgggaa tgtaattcag    3900
ctccgccatc gccgcttcca cttttccccg cgttttcgca gaaacgtggc tggcctggtt    3960
caccacgcgg gaaacggtct gataagagac accggcatac tctgcgacat cgtataacgt    4020
tactggtttc atgatatatc tccttaattg actctcttcc cgggcgctat catgccatac    4080
cgcgaaaggt tttgcgccat tcgatggtgt agatctcaaa taaaacgaaa ggctcagtcg    4140
aaagactggg cctttcgttt tatctgttgt ttgtcggtga acgctctcct gagtaggaca    4200
aatccgccgg gagcggattt gaacgttgcg aagcaacggc ccggagggtg cgggcagga    4260 cgcccgccat aaactgccag gcatcaaatt aagcagaagg ccatcctgac ggatggcctt    4320
tttgcgtttc tacaaactct tcc                                            4343

<210> SEQ ID NO 71
<211> LENGTH: 4585
<212> TYPE: DNA
<213> ORGANISM: Artificial Sequence
<220> FEATURE:
<223> OTHER INFORMATION: Synthetic sequence

<400> SEQUENCE: 71
gtacgaaatt aatacgactc actataggga attgtgagcg ctcacaattc tctagaaata     60
attttgttta actttaagaa ggagatatac catggagacc ggtaaaatac ataaggctta    120
ctaaaagcca gataacagta tgcgtatttg cgcgctgatt tttgcggtat aagaatatat    180
actgatatct atacccgaag tatgtcaaaa agaggtgtgc tatgcagttt aaggtttaca    240
cctataaaag agagagccgt tatcgtctgt ttgtggatgt acagagtgat attattgaca    300
cgcctgggcg acgcatggtg atccccctgg ccagtgcacg tctgctgtca gataaagtct    360
cccgtgaact ttacccggtg gtgcatatcg gggatgaaag ctggcgcatg atgaccaccg    420
atatggccag tgtgccagtc tccgttatcg gggaagaagt ggctgatctc agccaccgcg    480
aaaatgacat caaaaacgcc attaacctga tgttctgggg aatataacgg ccggtctcca    540
gtgatgacgc ggcaattcaa caaacgttag ccaaaatggg catcaaaagc agcgatattc    600
agcccgcgcc cgtagctggc atgaagacag ttctgactaa cagcggcgtg ttgtacatca    660
ccgatgatgg taaacatatc attcaggggc aatgtatga cgttagcggc acggctccgg    720
tcaatgtcac cataagatg ctgttaaagc agttgaatgc gggatcccat caccaccatc    780
atcactaagg taccgctgag caataactag cataacccct ggggcctct aaacgggtct    840 tgagggttt tttgctgaaa gcttgaattc ttagaaaaac tcatcgagca tcaaatgaaa    900
ctgcaattta ttcatatcag gattatcaat accatatttt tgaaaagcc gtttctgtaa    960 tgaaggagaa aactcaccga ggcagttcca taggatggca agatcctggt atcggtctgc    1020
gattccgact cgtccaacat caatacaacc tattaatttc ccctcgtcaa aaataaggtt    1080
atcaagtgag aaatcaccat gagtgacgac tgaatccggt gagaatggca aaagcttatg    1140
catttctttc cagacttgtt caacaggcca gccattacgc tcgtcatcaa aatcactcgc    1200
atcaaccaaa ccgttattca ttcgtgattg cgcctgagcg agacgaaata cgcggtcgct    1260
```

```
gttaaaagga caattacaaa caggaatcga atgcaaccgg cgcaggaaca ctgccagcgc    1320
atcaacaata ttttcacctg aatcaggata ttcttctaat acctggaatg ctgttttccc    1380
ggggatcgca gtggtgagta accatgcatc atcaggagta cggataaaat gcttgatggt    1440
cggaagaggc ataaattccg tcagccagtt tagtctgacc atctcatctg taacatcatt    1500
ggcaacgcta cctttgccat gtttcagaaa caactctggc gcatcgggct tcccatacaa    1560
tcgatagatt gtcgcacctg attgcccgac attatcgcga gcccatttat acccatataa    1620
atcagcatcc atgttggaat taatcgcgg cctcgagcaa gacgtttccc gttgaatatg     1680
gctcataaca ccccttgtat tactgtttat gtaagcagac agttttattg ttcatgacca    1740
aaatccctta acgtgagttt tcgttccact gagcgtcaga ccccgtagaa aagatcaaag    1800
gatcttcttg agatcctttt tttctgcgcg taatctgctg cttgcaaaca aaaaaaccac    1860
cgctaccagc ggtggtttgt ttgccggatc aagagctacc aactcttttt ccgaaggtaa    1920
ctggcttcag cagagcgcag ataccaaata ctgtccttct agtgtagccg tagttaggcc    1980
accacttcaa gaactctgta gcaccgccta catacctcgc tctgctaatc ctgttaccag    2040
tggctgctgc cagtggcgat aagtcgtgtc ttaccgggtt ggactcaaga cgatagttac    2100
cggataaggc gcagcggtcg ggctgaacgg ggggttcgtg cacacagccc agcttggagc    2160
gaacgaccta caccgaactg agatacctac agcgtgagct atgagaaagc gccacgcttc    2220
ccgaagggag aaaggcggac aggtatccgg taagcggcag ggtcggaaca ggagagcgca    2280
cgagggagct ccaggggga aacgcctggt atctttatag tcctgtcggg tttcgccacc     2340
tctgacttga gcgtcgattt ttgtgatgct cgtcagggg gcggagccta tggaaaaacg     2400
ccagcaacgc ggcctttta cggttcctgg cctttgctg ccttttgct cacatgctct       2460 ttcctgcgtt atcccctgat tctgtggata accgtattac cgcctttgag tgagctgata    2520
ccgctcgccg cagccgaacg accgagcgca gcgagtcagt gagcgaggaa gcggaagagc    2580
gcctgatgcg gtattttctc cttacgcatc tgtgcggtat ttcacaccgc atatatggtg    2640
cactctcagt acaatctgct ctgatgccgc atagttaagc cagtatacac tccgctatcg    2700
ctacgtgact gggtcatggc tgcgccccga cacccgccaa cacccgctga cgcgccctga    2760
cgggcttgtc tgctcccggc atccgcttac agacaagctg tgaccgtctc cgggagctgc    2820
atgtgtcaga ggttttcacc gtcatcaccg aaacgcgcga ggcagctgcg gtaaagctca    2880
tcagcgtggt cgtgaagcga ttcacagatg tctgcctgtt catccgcgtc cagctcgttg    2940
agtttctcca gaagcgttaa tgtctggctt ctgataaagc gggccatgtt aagggcggtt    3000
ttttcctgtt tggtcactga tgcctccgtg taagggggat ttctgttcat gggggtaatg    3060
ataccgatga acgagagag gatgctcacg atacgggtta ctgatgatga acatgcccgg    3120
ttactggaac gttgtgaggg taaacaactg gcggtatgga tgcggcggga ccagagaaaa    3180
atcaccctag gtcactgccc gctttccagt cgggaaacct gtcgtgccag ctgcattaat    3240
gaatcggcca acgcgcgggg agaggcggtt tgcgtattgg gcgccagggt ggttttctct    3300
ttcaccagtg agacgggcaa cagctgattg cccttcaccg cctggccctg agagagttgc    3360
agcaagcggt ccacgctggt ttgccccagc aggcgaaaat cctgtttgat ggtggttaac    3420
ggcgggatat aacatgagct gtcttcggta tcgtcgtatc ccactaccga gatatccgca    3480
ccaacgcgca gcccggactc ggtaatggcg cgcattgcgc ccagcgccat ctgatcgttg    3540
gcaaccagca tcgcagtggg aacgatgccc tcattcagca tttgcatggt ttgttgaaaa    3600
ccggacatgg cactccagtc gccttcccgt tccgctatcg gctgaatttg attgcgagtg    3660
```

```
agatatttat gccagccagc cagacgcaga cgcgccgaga cagaacttaa tgggcccgct   3720
aacagcgcga tttgctggtg acccaatgcg accagatgct ccacgccag tcgcgtaccg    3780 tcttcatggg agaaaataat actgttgatg ggtgtctggt cagagacatc aagaaataac   3840
gccggaacat tagtgcaggc agcttccaca gcaatggcat cctggtcatc cagcggatag   3900
ttaatgatca gcccactgac gcgttgcgcg agaagattgt gcaccgccgc tttacaggct   3960
tcgacgccgc ttcgttctac catcgacacc accacgctgg cacccagttg atcggcgcga   4020
gatttaatcg ccgcgacaat ttgcgacggc gcgtgcaggg ccagactgga ggtggcaacg   4080
ccaatcagca acgactgttt gcccgccagt tgttgtgcca cgcggttggg aatgtaattc    4140
agctccgcca tcgccgcttc acttttttcc cgcgttttcg cagaaacgtg gctggcctgg    4200
ttcaccacgc gggaaacggt ctgataagag acaccggcat actctgcgac atcgtataac    4260
gttactggtt tcatgatata tctccttaat tgactctctt cccgggcgct atcatgccat    4320
accgcgaaag gttttgcgcc attcgatggt gtagatctca aataaaacga aaggctcagt   4380
cgaaagactg ggcctttcgt tttatctgtt gtttgtcggt gaacgctctc ctgagtagga    4440
caaatccgcc gggagcggat ttgaacgttg cgaagcaacg gcccgagggg tggcgggcag    4500
gacgcccgcc ataaactgcc aggcatcaaa ttaagcagaa ggccatcctg acggatggcc    4560
tttttgcgtt tctacaaact cttcc                                         4585

<210> SEQ ID NO 72
<211> LENGTH: 4565
<212> TYPE: DNA
<213> ORGANISM: Artificial Sequence
<220> FEATURE:
<223> OTHER INFORMATION: Synthetic sequence

<400> SEQUENCE: 72
gtacgaaatt aatacgactc actataggga attgtgagcg ctcacaattc tctagaagaa     60
ggagatatac catggagacc ggtaaaatac ataaggctta ctaaaagcca gataacagta    120
tgcgtatttg cgcgctgatt tttgcggtat aagaatatat actgatatct atacccgaag    180
tatgtcaaaa agaggtgtgc tatgcagttt aaggtttaca cctataaaag agagagccgt    240
tatcgtctgt ttgtggatgt acagagtgat attattgaca cgcctgggcg acgcatggtg    300
atccccctgg ccagtgcacg tctgctgtca gataaagtct cccgtgaact ttacccggtg    360
gtgcatatcg gggatgaaag ctggcgcatg atgaccaccg atatggccag tgtgccagtc    420
tccgttatcg gggaagaagt ggctgatctc agccaccgcg aaaatgacat caaaaacgcc    480
attaacctga tgttctgggg aatataacgg ccggtctcca gtgatgacgc ggcaattcaa    540
caaacgttag ccaaaatggg catcaaaagc agcgatattc agcccgcgcc cgtagctggc    600
atgaagacag ttctgactaa cagcggcgtg ttgtacatca ccgatgatgg taaacatatc    660
attcaggggc aatgtatga cgttagcggc acggctccgg tcaatgtcac caataagatg    720
ctgttaaagc agttgaatgc gggatcccat caccaccatc atcactaagg taccgctgag    780
caataactag cataacccct tggggcctct aaacgggtct tgaggggttt tttgctgaaa    840
gcttgaattc ttagaaaaac tcatcgagca tcaaatgaaa ctgcaattta ttcatatcag    900
gattatcaat accatatttt tgaaaaagcc gtttctgtaa tgaaggagaa aactcaccga    960
ggcagttcca taggatggca agatcctggt atcggtctgc gattccgact cgtccaacat   1020
caatacaacc tattaatttc ccctcgtcaa aaataaggtt atcaagtgag aaatcaccat   1080
```

```
gagtgacgac tgaatccggt gagaatggca aaagcttatg catttctttc cagacttgtt    1140
caacaggcca gccattacgc tcgtcatcaa aatcactcgc atcaaccaaa ccgttattca    1200
ttcgtgattg cgcctgagcg agacgaaata cgcggtcgct gttaaaagga caattacaaa    1260
caggaatcga atgcaaccgg cgcaggaaca ctgccagcgc atcaacaata ttttcacctg    1320
aatcaggata ttcttctaat acctggaatg ctgttttccc ggggatcgca gtggtgagta    1380
accatgcatc atcaggagta cggataaaat gcttgatggt cggaagaggc ataaattccg    1440
tcagccagtt tagtctgacc atctcatctg taacatcatt ggcaacgcta cctttgccat    1500
gtttcagaaa caactctggc gcatcgggct tcccatacaa tcgatagatt gtcgcacctg    1560
attgcccgac attatcgcga gcccatttat acccatataa atcagcatcc atgttggaat    1620
ttaatcgcgg cctcgagcaa gacgtttccc gttgaatatg gctcataaca ccccttgtat    1680
tactgtttat gtaagcagac agttttattg ttcatgacca aaatcccttta acgtgagttt    1740 tcgttccact gagcgtcaga ccccgtagaa aagatcaaag gatcttcttg agatcctttt    1800
tttctgcgcg taatctgctg cttgcaaaca aaaaaaccac cgctaccagc ggtggtttgt    1860
ttgccggatc aagagctacc aactcttttt ccgaaggtaa ctggcttcag cagagcgcag    1920
ataccaaata ctgtccttct agtgtagccg tagttaggcc accacttcaa gaactctgta    1980
gcaccgccta catacctcgc tctgctaatc ctgttaccag tggctgctgc cagtggcgat    2040
aagtcgtgtc ttaccgggtt ggactcaaga cgatagttac cggataaggc gcagcggtcg    2100
ggctgaacgg ggggttcgtg cacacagccc agcttggagc gaacgaccta caccgaactg    2160
agatacctac agcgtgagct atgagaaagc gccacgcttc ccgaagggag aaaggcggac    2220
aggtatccgg taagcggcag ggtcggaaca ggagagcgca cgagggagct ccaggggga    2280 aacgcctggt atctttatag tcctgtcggg tttcgccacc tctgacttga gcgtcgattt    2340
ttgtgatgct cgtcaggggg gcggagccta tggaaaaacg ccagcaacgc ggccttttta    2400
cggttcctgg ccttttgctg gccttttgct cacatgctct ttcctgcgtt atcccctgat    2460
tctgtggata accgtattac cgcctttgag tgagctgata ccgctcgccg cagccgaacg    2520
accgagcgca gcgagtcagt gagcgaggaa gcggaagagc gcctgatgcg gtattttctc    2580
cttacgcatc tgtgcggtat ttcacaccgc atatatggtg cactctcagt acaatctgct    2640
ctgatgccgc atagttaagc cagtatacac tccgctatcg ctacgtgact gggtcatggc    2700
tgcgccccga cacccgccaa cacccgctga cgcgccctga cgggcttgtc tgctcccggc    2760
atccgcttac agacaagctg tgaccgtctc cgggagctgc atgtgtcaga ggttttcacc    2820
gtcatcaccg aaacgcgcga ggcagctgcg gtaaagctca tcagcgtggt cgtgaagcga    2880
ttcacagatg tctgcctgtt catccgcgtc cagctcgttg agtttctcca gaagcgttaa    2940
tgtctggctt ctgataaagc gggccatgtt aagggcggtt ttttcctgtt tggtcactga    3000
tgcctccgtg taaggggat ttctgttcat gggggtaatg ataccgatga acgagagag    3060 gatgctcacg atacgggtta ctgatgatga acatgcccgg ttactggaac gttgtgaggg    3120
taaacaactg gcggtatgga tgcggcggga ccagagaaaa atcaccctag gtcactgccc    3180
gctttccagt cgggaaacct gtcgtgccag ctgcattaat gaatcggcca acgcgcgggg    3240
agaggcggtt tgcgtattgg gcgccagggt ggttttcctt ttcaccagtg agacgggcaa    3300
cagctgattg cccttcaccg cctggccctg agagagttgc agcaagcggt ccacgctggt    3360
ttgccccagc aggcgaaaat cctgtttgat ggtggttaac ggcgggatat aacatgagct    3420
gtcttcggta tcgtcgtatc ccactaccga gatatccgca ccaacgcgca gcccggactc    3480
```

```
ggtaatggcg cgcattgcgc ccagcgccat ctgatcgttg caaccagca tcgcagtggg    3540 aacgatgccc tcattcagca tttgcatggt ttgttgaaaa ccggacatgg cactccagtc    3600
gccttcccgt tccgctatcg gctgaatttg attgcgagtg agatatttat gccagccagc    3660
cagacgcaga cgcgccgaga cagaacttaa tgggcccgct aacagcgcga tttgctggtg    3720
acccaatgcg accagatgct ccacgcccag tcgcgtaccg tcttcatggg agaaaataat    3780
actgttgatg ggtgtctggt cagagacatc aagaaataac gccggaacat tagtgcaggc    3840
agcttccaca gcaatggcat cctggtcatc cagcggatag ttaatgatca gcccactgac    3900
gcgttgcgcg agaagattgt gcaccgccgc tttacaggct tcgacgccgc ttcgttctac    3960
catcgacacc accacgctgg cacccagttg atcgcgcgcga gatttaatcg ccgcgacaat    4020
ttgcgacggc gcgtgcaggg ccagactgga ggtggcaacg ccaatcagca acgactgttt    4080
gcccgccagt tgttgtgcca cgcggttggg aatgtaattc agctccgcca tcgccgcttc    4140
cactttttcc cgcgttttcg cagaaacgtg gctggcctgg ttcaccacgc gggaaacggt    4200
ctgataagag acaccggcat actctgcgac atcgtataac gttactggtt tcatgatata    4260
tctccttaat tgactctctt cccgggcgct atcatgccat accgcgaaag gttttgcgcc    4320
attcgatggt gtagatctca aataaaacga aaggctcagt cgaaagactg gcctttcgt     4380 tttatctgtt gtttgtcggt gaacgctctc ctgagtagga caaatccgcc gggagcggat    4440
ttgaacgttg cgaagcaacg gcccgagggg tggcgggcag gacgcccgcc ataaactgcc    4500
aggcatcaaa ttaagcagaa ggccatcctg acggatggcc ttttttgcgtt tctacaaact    4560 cttcc                                                                4565
```

<210> SEQ ID NO 73
<211> LENGTH: 4595
<212> TYPE: DNA
<213> ORGANISM: Artificial Sequence
<220> FEATURE:
<223> OTHER INFORMATION: Synthetic sequence

<400> SEQUENCE: 73

```
gtacgaaatt aatacgactc actataggga attgtgagcg ctcacaattc tctagaaata     60
attttgttta actttaagaa ggagatatac atatggctag ccatcaccac catcatcact    120
cggagaccgg taaatacat aaggcttact aaaagccaga taacagtatg cgtatttgcg     180
cgctgatttt tgcggtataa gaatatatac tgatatctat acccgaagta tgtcaaaaag    240
aggtgtgcta tgcagtttaa ggtttacacc tataaagag agagccgtta tcgtctgttt     300
gtggatgtac agagtgatat tattgacacg cctgggcgac gcatggtgat cccctggcc     360 agtgcacgtc tgctgtcaga taaagtctcc cgtgaacttt accggtggt gcatatcggg     420 gatgaaagct ggcgcatgat gaccaccgat atggccagtg tgccagtctc cgttatcggg    480
gaagaagtgc tgatctcag ccaccgcgaa atgacatca aaaacgccat taacctgatg      540
ttctggggaa tataacggcc ggtctccagt gatgacgcgg caattcaaca aacgttagcc    600
aaaatgggca tcaaaagcag cgatattcag cccgcgcccg tagctggcat gaagacagtt    660
ctgactaaca gcggcgtgtt gtacatcacc gatgatggta acatatcat tcaggggcca    720 atgtatgacg ttagcggcac ggctccggtc aatgtcacca ataagatgct gttaaagcag    780
ttgaatgcgg gatcctaagg taccgctgag caataactag cataaccccct tggggcctct    840 aaacgggtct tgaggggttt tttgctgaaa gcttgaattc ttagaaaaac tcatcgagca    900
```

```
tcaaatgaaa ctgcaatttq ttcatatcag gattatcaat accatatttt tgaaaaagcc      960
gtttctgtaa tgaaggagaa aactcaccga ggcagttcca taggatggca agatcctggt     1020
atcggtctgc gattccgact cgtccaacat caatacaacc tattaatttc ccctcgtcaa     1080
aaataaggtt atcaagtgag aaatcaccat gagtgacgac tgaatccggt gagaatggca     1140
aaagcttatg catttctttc cagacttgtt caacaggcca gccattacgc tcgtcatcaa     1200
aatcactcgc atcaaccaaa ccgttattca ttcgtgattg cgcctgagcg agacgaaata     1260
cgcggtcgct gttaaaagga caattacaaa caggaatcga atgcaaccgg cgcaggaaca     1320
ctgccagcgc atcaacaata ttttcacctg aatcaggata ttcttctaat acctggaatg     1380
ctgttttccc ggggatcgca gtggtgagta accatgcatc atcaggagta cggataaaat     1440
gcttgatggt cggaagaggc ataaattccg tcagccagtt tagtctgacc atctcatctg     1500
taacatcatt ggcaacgcta cctttgccat gtttcagaaa caactctggc gcatcgggct     1560
tcccatacaa tcgatagatt gtcgcacctg attgcccgac attatcgcga gcccatttat     1620
acccatataa atcagcatcc atgttggaat ttaatcgcgg cctcgagcaa gacgtttccc     1680
gttgaatatg gctcataaca ccccttgtat tactgtttat gtaagcagac agttttattg     1740
ttcatgacca aaatcccta acgtgagttt tcgttccact gagcgtcaga ccccgtagaa     1800
aagatcaaag gatcttcttg agatcctttt tttctgcgcg taatctgctg cttgcaaaca     1860
aaaaaaccac cgctaccagc ggtggtttgt ttgccggatc aagagctacc aactcttttt     1920
ccgaaggtaa ctggcttcag cagagcgcag ataccaaata ctgtccttct agtgtagccg     1980
tagttaggcc accacttcaa gaactctgta gcaccgccta catacctcgc tctgctaatc     2040
ctgttaccag tggctgctgc cagtggcgat aagtcgtgtc ttaccgggtt ggactcaaga     2100
cgatagttac cggataaggc gcagcggtcg ggctgaacgg ggggttcgtg cacacagccc     2160
agcttggagc gaacgaccta caccgaactg agatacctac agcgtgagct atgagaaagc     2220
gccacgcttc ccgaagggag aaaggcggac aggtatccgg taagcggcag gtcggaaca      2280 ggagagcgca cgagggagct tccaggggga aacgcctggt atctttatag tcctgtcggg     2340
tttcgccacc tctgacttga gcgtcgattt ttgtgatgct cgtcagggggg cggagccta     2400 tggaaaaacg ccagcaacgc ggcctttttta cggttcctgg cctttgctg gccttttgct     2460 cacatgctct ttcctgcgtt atcccctgat tctgtggata accgtattac cgcctttgag     2520
tgagctgata ccgctcgccg cagccgaacg accgagcgca gcgagtcagt gagcgaggaa     2580
gcggaagagc gcctgatgcg gtattttctc cttacgcatc tgtgcggtat ttcacaccgc     2640
atatatggtg cactctcagt acaatctgct ctgatgccgc atagttaagc cagtatacac     2700
tccgctatcg ctacgtgact gggtcatggc tgcgccccga cacccgccaa cacccgctga     2760
cgcgccctga cgggcttgtc tgctcccggc atccgcttac agacaagctg tgaccgtctc     2820
cgggagctgc atgtgtcaga ggttttcacc gtcatcaccg aaacgcgcga ggcagctgcg     2880
gtaaagctca tcagcgtggt cgtgaagcga ttcacagatg tctgcctgtt catccgcgtc     2940
cagctcgttg agtttctcca gaagcgttaa tgtctggctt ctgataaagc gggccatgtt     3000
aagggcggtt ttttcctgtt tggtcactga tgcctccgtg taagggggat ttctgttcat     3060
gggggtaatg ataccgatga aacgagagag gatgctcacg atacgggtta ctgatgatga     3120
acatgcccgg ttactggaac gttgtgaggg taaacaactg gcggtatgga tgcggcggga     3180
ccagagaaaa atcaccctag gtcactgccc gctttccagt cgggaaacct gtcgtgccag     3240
ctgcattaat gaatcggcca acgcgcgggg agaggcggtt tgcgtattgg gcgccagggt     3300
```

```
ggttttctt ttcaccagtg agacgggcaa cagctgattg cccttcaccg cctggcctg    3360 agagagttgc agcaagcggt ccacgctggt ttgccccagc aggcgaaaat cctgtttgat   3420
ggtggttaac ggcgggatat aacatgagct gtcttcggta tcgtcgtatc ccactaccga   3480
gatatccgca ccaacgcgca gcccggactc ggtaatggcg cgcattgcgc ccagcgccat   3540
ctgatcgttg gcaaccagca tcgcagtggg aacgatgccc tcattcagca tttgcatggt   3600
ttgttgaaaa ccggacatgg cactccagtc gccttcccgt tccgctatcg gctgaatttg   3660
attgcgagtg agatatttat gccagccagc cagacgcaga cgcgccgaga cagaacttaa   3720
tgggcccgct aacagcgcga tttgctggtg acccaatgcg accagatgct ccacgcccag   3780
tcgcgtaccg tcttcatggg agaaaataat actgttgatg ggtgtctggt cagagacatc   3840
aagaaataac gccggaacat tagtgcaggc agcttccaca gcaatggcat cctggtcatc   3900
cagcggatag ttaatgatca gcccactgac gcgttgcgcg agaagattgt gcaccgccgc   3960
tttacaggct tcgacgccgc ttcgttctac catcgacacc accacgctgg cacccagttg   4020
atcggcgcga gatttaatcg ccgcgacaat ttgcgacggc gcgtgcaggg ccagactgga   4080
ggtggcaacg ccaatcagca acgactgttt gcccgccagt tgttgtgcca cgcggttggg   4140
aatgtaattc agctccgcca tcgccgcttc cacttttttcc cgcgttttcg cagaaacgtg   4200
gctggcctgg ttcaccacgc gggaaacggt ctgataagag acaccggcat actctgcgac   4260
atcgtataac gttactggtt tcatgatata tctccttaat tgactctctt cccgggcgct   4320
atcatgccat accgcgaaag gttttgcgcc attcgatggt gtagatctca aataaaacga   4380
aaggctcagt cgaaagactg ggcctttcgt tttatctgtt gtttgtcggt gaacgctctc   4440
ctgagtagga caaatccgcc gggagcggat ttgaacgttg cgaagcaacg gcccggaggg   4500
tggcgggcag gacgcccgcc ataaactgcc aggcatcaaa ttaagcagaa ggccatcctg   4560
acggatggcc ttttttgcgtt tctacaaact cttcc                            4595
```

<210> SEQ ID NO 74
<211> LENGTH: 4575
<212> TYPE: DNA
<213> ORGANISM: Artificial Sequence
<220> FEATURE:
<223> OTHER INFORMATION: Synthetic sequence

<400> SEQUENCE: 74

```
gtacgaaatt aatacgactc actataggga attgtgagcg ctcacaattc tctagaagaa     60
ggagatatac atatggctag ccatcaccac catcatcact cggagaccgg taaaatacat    120
aaggcttact aaaagccaga taacagtatg cgtatttgcg cgctgatttt tgcggtataa    180
gaatatatac tgatatctat acccgaagta tgtcaaaaag aggtgtgcta tgcagtttaa    240
ggtttacacc tataaaagag agagccgtta tcgtctgttt gtggatgtac agagtgatat    300
tattgacacg cctgggcgac gcatggtgat cccctggcc agtgcacgtc tgctgtcaga    360
taaagtctcc cgtgaacttt acccggtggt gcatatcggg gatgaaagct ggcgcatgat    420
gaccaccgat atggccagtg tgccagtctc cgttatcggg gaagaagtgg ctgatctcag    480
ccaccgcgaa aatgacatca aaaacgccat taacctgatg ttctgggaa ataacggcc    540 ggtctccagt gatgacgcgg caattcaaca aacgttagcc aaaatgggca tcaaaagcag    600
cgatattcag cccgcgcccg tagctggcat gaagacagtt ctgactaaca gcggcgtgtt    660
gtacatcacc gatgatggta acatatcat tcaggggcca atgtatgacg ttagcggcac    720
```

```
ggctccggtc aatgtcacca ataagatgct gttaaagcag ttgaatgcgg gatcctaagg    780
taccgctgag caataactag cataaccct tggggcctct aaacgggtct tgagggtttt     840
tttgctgaaa gcttgaattc ttagaaaaac tcatcgagca tcaaatgaaa ctgcaattta    900
ttcatatcag gattatcaat accatatttt gaaaaagcc gttctgtaa tgaaggagaa      960 aactcaccga ggcagttcca taggatggca agatcctggt atcggtctgc gattccgact   1020
cgtccaacat caatacaacc tattaatttc ccctcgtcaa aaataaggtt atcaagtgag   1080
aaatcaccat gagtgacgac tgaatccggt gagaatggca aaagcttatg catttctttc   1140
cagacttgtt caacaggcca gccattacgc tcgtcatcaa aatcactcgc atcaaccaaa   1200
ccgttattca ttcgtgattg cgcctgagcg agacgaaata cgcggtcgct gttaaaagga   1260
caattacaaa caggaatcga atgcaaccgg cgcaggaaca ctgccagcgc atcaacaata   1320
ttttcacctg aatcaggata ttcttctaat acctggaatg ctgttttccc ggggatcgca   1380
gtggtgagta accatgcatc atcaggagta cggataaaat gcttgatggt cggaagaggc   1440
ataaattccg tcagccagtt tagtctgacc atctcatctg taacatcatt ggcaacgcta   1500
cctttgccat gtttcagaaa caactctggc gcatcgggct tcccatacaa tcgatagatt   1560
gtcgcacctg attgcccgac attatcgcga gcccatttat acccatataa atcagcatcc   1620
atgttggaat ttaatcgcgg cctcgagcaa gacgtttccc gttgaatatg gctcataaca   1680
ccccttgtat tactgtttat gtaagcagac agttttattg ttcatgacca aaatcccta    1740 acgtgagttt tcgttccact gagcgtcaga ccccgtagaa aagatcaaag gatcttcttg   1800 agatccttttt tttctgcgcg taatctgctg cttgcaaaca aaaaaccac cgctaccagc   1860 ggtggtttgt ttgccggatc aagagctacc aactcttttt ccgaaggtaa ctggcttcag   1920
cagagcgcag ataccaaata ctgtccttct agtgtagccg tagttaggcc accacttcaa   1980
gaactctgta gcaccgccta catacctcgc tctgctaatc ctgttaccag tggctgctgc   2040
cagtggcgat aagtcgtgtc ttaccgggtt ggactcaaga cgatagttac cggataaggc   2100
gcagcggtcg ggctgaacgg ggggttcgtg cacacagccc agcttggagc gaacgaccta   2160
caccgaactg agatacctac agcgtgagct atgagaaagc gccacgcttc ccgaagggag   2220
aaaggcggac aggtatccgg taagcggcag ggtcggaaca ggagagcgca cgagggagct   2280
tccaggggga aacgcctggt atctttatag tcctgtcggg tttcgccacc tctgacttga   2340
gcgtcgattt ttgtgatgct cgtcaggggg gcggagccta tggaaaaacg ccagcaacgc   2400
ggccttttta cggttcctgg ccttttgctg gccttttgct cacatgctct ttcctgcgtt   2460
atcccctgat tctgtggata accgtattac cgcctttgag tgagctgata ccgctcgccg   2520
cagccgaacg accgagcgca gcgagtcagt gagcgaggaa gcggaagagc gcctgatgcg   2580 gtatttctc cttacgcatc tgtgcggtat ttcacaccgc atatatggtg cactctcagt   2640
acaatctgct ctgatgccgc atagttaagc cagtatacac tccgctatcg ctacgtgact   2700
gggtcatggc tgcgccccga cacccgccaa cacccgctga cgcgccctga cgggcttgtc   2760
tgctcccggc atccgcttac agacaagctg tgaccgtctc cgggagctgc atgtgtcaga   2820
ggttttcacc gtcatcaccg aaacgcgcga ggcagctgcg gtaaagctca tcagcgtggt   2880
cgtgaagcga ttcacagatg tctgcctgtt catccgcgtc cagctcgttg agtttctcca   2940
gaagcgttaa tgtctggctt ctgataaagc gggccatgtt aagggcggtt ttttcctgtt   3000
tggtcactga tgcctccgtg taagggggat ttctgttcat gggggtaatg ataccgatga   3060
aacgagagag gatgctcacg atacgggtta ctgatgatga acatgcccgg ttactggaac   3120
```

```
gttgtgaggg taaacaactg gcggtatgga tgcggcggga ccagagaaaa atcaccctag    3180
gtcactgccc gctttccagt cgggaaacct gtcgtgccag ctgcattaat gaatcggcca    3240
acgcgcgggg agaggcggtt tgcgtattgg gcgccagggt ggttttcct ttcaccagtg    3300 agacgggcaa cagctgattg ccttcaccg cctggccctg agagagttgc agcaagcggt    3360
ccacgctggt ttgccccagc aggcgaaaat cctgtttgat ggtggttaac ggcgggatat    3420
aacatgagct gtcttcggta tcgtcgtatc ccactaccga gatatccgca ccaacgcgca    3480
gcccggactc ggtaatggcg cgcattgcgc ccagcgccat ctgatcgttg caaccagca    3540 tcgcagtggg aacgatgccc tcattcagca tttgcatggt tgttgaaaaa ccggacatgg    3600
cactccagtc gccttcccgt tccgctatcg gctgaatttg attgcgagtg agatatttat    3660
gccagccagc cagacgcaga cgcgccgaga cagaacttaa tgggcccgct aacagcgcga    3720
tttgctggtg acccaatgcg accagatgct ccacgcccag tcgcgtaccg tcttcatggg    3780
agaaaataat actgttgatg ggtgtctggt cagagacatc aagaaataac gccggaacat    3840
tagtgcaggc agcttccaca gcaatggcat cctggtcatc cagcggatag ttaatgatca    3900
gcccactgac gcgttgcgcg agaagattgt gcaccgccgc tttacaggct tcgacgccgc    3960
ttcgttctac catcgacacc accacgctgg cacccagttg atcggcgcga gatttaatcg    4020
ccgcgacaat ttgcgacggc gcgtgcaggg ccagactgga ggtggcaacg ccaatcagca    4080
acgactgttt gcccgccagt tgttgtgcca cgcggttggg aatgtaattc agctccgcca    4140
tcgccgcttc cacttttcc cgcgttttcg cagaaacgtg gctggcctgg ttcaccacgc    4200
gggaaacggt ctgataagag acaccggcat actctgcgac atcgtataac gttactggtt    4260
tcatgatata tctccttaat tgactctctt cccgggcgct atcatgccat accgcgaaag    4320
gttttgcgcc attcgatggt gtagatctca aataaaacga aaggctcagt cgaaagactg    4380
ggcctttcgt tttatctgtt gtttgtcggt gaacgctctc ctgagtagga caaatccgcc    4440
gggagcggat ttgaacgttg cgaagcaacg gcccggaggg tggcgggcag gacgcccgcc    4500
ataaactgcc aggcatcaaa ttaagcagaa ggccatcctg acggatggcc ttttttgcgtt    4560 tctacaaact cttcc                                                     4575
```

<210> SEQ ID NO 75
<211> LENGTH: 4652
<212> TYPE: DNA
<213> ORGANISM: Artificial Sequence
<220> FEATURE:
<223> OTHER INFORMATION: Synthetic sequence

<400> SEQUENCE: 75

```
gtacgaaatt aatacgactc actataggga attgtgagcg ctcacaattc tctagaaata     60
attttgttta actttaagaa ggagatatac atatgaaata cctcttgcct acggcagccg    120
ctggattgtt attactcgca gcccaaccag cgatggctgc agagaccggt aaaatacata    180
aggcttacta aaagccagat aacagtatgc gtatttgcgc gctgattttt gcggtataag    240
aatatatact gatatctata cccgaagtat gtcaaaaaga ggtgtgctat gcagtttaag    300
gtttacacct ataaaagaga gagccgttat cgtctgtttg tggatgtaca gagtgatatt    360
attgacacgc ctgggcgacg catggtgatc cccctggcca gtgcacgtct gctgtcagat    420
aaagtctccc gtgaacttta cccggtggtg catatcgggg atgaaagctg gcgcatgatg    480
accaccgata tggccagtgt gccagtctcc gttatcgggg aagaagtggc tgatctcagc    540
```

-continued

```
caccgcgaaa atgacatcaa aaacgccatt aacctgatgt tctggggaat ataacggccg    600
gtctcaagcg atgacgcggc aattcaacaa acgttagcca aaatgggcat caaaagcagc    660
gatattcagc ccgcgcccgt agctggcatg aagacagttc tgactaacag cggcgtgttg    720
tacatcaccg atgatggtaa acatatcatt caggggccaa tgtatgacgt tagcggcacg    780
gctccggtca atgtcaccaa taagatgctg ttaaagcagt tgaatgcggg atcccatcac    840
caccatcatc actaaggtac cgctgagcaa taactagcat aaccccttgg ggcctctaaa    900
cgggtcttga ggggtttttt gctgaaagct tgaattctta gaaaaactca tcgagcatca    960
aatgaaactg caatttattc atatcaggat tatcaatacc atattttga aaaagccgtt   1020 tctgtaatga aggagaaaac tcaccgaggc agttccatag gatggcaaga tcctggtatc   1080
ggtctgcgat tccgactcgt ccaacatcaa tacaacctat taatttcccc tcgtcaaaaa   1140
taaggttatc aagtgagaaa tcaccatgag tgacgactga atccggtgag aatggcaaaa   1200
gcttatgcat ttctttccag acttgttcaa caggccagcc attacgctcg tcatcaaaat   1260
cactcgcatc aaccaaaccg ttattcattc gtgattgcgc ctgagcgaga cgaaatacgc   1320
ggtcgctgtt aaaaggacaa ttacaaacag gaatcgaatg caaccggcgc aggaacactg   1380
ccagcgcatc aacaatattt tcacctgaat caggatattc ttctaatacc tggaatgctg   1440
ttttcccggg gatcgcagtg gtgagtaacc atgcatcatc aggagtacgg ataaaatgct   1500
tgatggtcgg aagaggcata aattccgtca gccagtttag tctgaccatc tcatctgtaa   1560
catcattggc aacgctacct ttgccatgtt tcagaaacaa ctctggcgca tcgggcttcc   1620
catacaatcg atagattgtc gcacctgatt gcccgacatt atcgcgagcc catttatacc   1680
catataaatc agcatccatg ttggaattta atcgcggcct cgagcaagac gtttcccgtt   1740
gaatatggct cataacaccc cttgtattac tgtttatgta agcagacagt tttattgttc   1800
atgaccaaaa tcccttaacg tgagttttcg ttccactgag cgtcagaccc cgtagaaaag   1860
atcaaaggat cttcttgaga tcctttttt ctgcgcgtaa tctgctgctt gcaaacaaaa   1920
aaaccaccgc taccagcggt ggtttgtttg ccggatcaag agctaccaac tcttttttccg   1980 aaggtaactg gcttcagcag agcgcagata ccaaatactg tccttctagt gtagccgtag   2040
ttaggccacc acttcaagaa ctctgtagca ccgcctacat acctcgctct gctaatcctg   2100
ttaccagtgg ctgctgccag tggcgataag tcgtgtctta ccgggttgga ctcaagacga   2160
tagttaccgg ataaggcgca gcggtcgggc tgaacggggg gttcgtgcac acagcccagc   2220
ttggagcgaa cgacctacac cgaactgaga tacctacagc gtgagctatg agaaagcgcc   2280
acgcttcccg aagggagaaa ggcggacagg tatccggtaa gcggcagggt cggaacagga   2340
gagcgcacga gggagcttcc agggggaaac gcctggtatc tttatagtcc tgtcgggttt   2400
cgccacctct gacttgagcg tcgatttttg tgatgctcgt caggggggcg gagcctatgg   2460
aaaaacgcca gcaacgcggc cttttttacgg ttcctggcct tttgctggcc ttttgctcac   2520
atgctctttc ctgcgttatc ccctgattct gtggataacc gtattaccgc ctttgagtga   2580
gctgataccg ctcgccgcag ccgaacgacc gagcgcagcg agtcagtgag cgaggaagcg   2640 gaaagagcgcc tgatgcggta ttttctcctt acgcatctgt gcggtatttc acaccgcata   2700
tatggtgcac tctcagtaca atctgctctg atgccgcata gttaagccag tatacactcc   2760
gctatcgcta cgtgactggg tcatggctgc gccccgacac ccgccaacac ccgctgacgc   2820
gccctgacgg gcttgtctgc tcccggcatc cgcttacaga caagctgtga ccgtctccgg   2880
gagctgcatg tgtcagaggt tttcaccgtc atcaccgaaa cgcgcgaggc agctgcggta   2940
```

```
aagctcatca gcgtggtcgt gaagcgattc acagatgtct gcctgttcat ccgcgtccag    3000
ctcgttgagt ttctccagaa gcgttaatgt ctggcttctg ataaagcggg ccatgttaag    3060
ggcggttttt tcctgtttgg tcactgatgc ctccgtgtaa gggggatttc tgttcatggg    3120
ggtaatgata ccgatgaaac gagagaggat gctcacgata cgggttactg atgatgaaca    3180
tgcccggtta ctggaacgtt gtgagggtaa acaactggcg gtatggatgc ggcgggacca    3240
gagaaaaatc accctaggtc actgcccgct ttccagtcgg gaaacctgtc gtgccagctg    3300
cattaatgaa tcggccaacg cgcggggaga ggcggtttgc gtattgggcg ccagggtggt    3360
ttttcttttc accagtgaga cgggcaacag ctgattgccc ttcaccgcct ggccctgaga    3420
gagttgcagc aagcggtcca cgctggtttg ccccagcagg cgaaaatcct gtttgatggt    3480
ggttaacggc gggatataac atgagctgtc ttcggtatcg tcgtatccca ctaccgagat    3540
atccgcacca acgcgcagcc cggactcggt aatggcgcgc attgcgccca gcgccatctg    3600
atcgttggca accagcatcg cagtgggaac gatgccctca ttcagcattt gcatggtttg    3660
ttgaaaaccg gacatggcac tccagtcgcc ttcccgttcc gctatcggct gaatttgatt    3720
gcgagtgaga tatttatgcc agccagccag acgcagacgc gccgagacag aacttaatgg    3780
gcccgctaac agcgcgattt gctggtgacc caatgcgacc agatgctcca cgcccagtcg    3840
cgtaccgtct tcatgggaga aaataatact gttgatgggt gtctggtcag agacatcaag    3900
aaataacgcc ggaacattag tgcaggcagc ttccacagca atggcatcct ggtcatccag    3960
cggatagtta atgatcagcc cactgacgcg ttgcgcgaga agattgtgca ccgccgcttt    4020
acaggcttcg acgccgcttc gttctaccat cgacaccacc acgctggcac ccagttgatc    4080
ggcgcgagat ttaatcgccg cgacaatttg cgacggcgcg tgcagggcca gactggaggt    4140
ggcaacgcca atcagcaacg actgtttgcc cgccagttgt tgtgccacgc ggttgggaat    4200
gtaattcagc tccgccatcg ccgcttccac ttttcccgc gttttcgcag aaacgtggct    4260
ggcctggttc accacgcggg aaacggtctg ataagagaca ccggcatact ctgcgacatc    4320
gtataacgtt actggtttca tgatatatct ccttaattga ctctcttccc gggcgctatc    4380
atgccatacc gcgaaaggtt ttgcgccatt cgatggtgta gatctcaaat aaaacgaaag    4440
gctcagtcga aagactgggc ctttcgtttt atctgttgtt tgtcggtgaa cgctctcctg    4500
agtaggacaa atccgccggg agcggatttg aacgttgcga agcaacgccc ggagggtgg    4560 cgggcaggac gcccgccata aactgccagg catcaaatta agcagaaggc catcctgacg    4620
gatggccttt ttgcgtttct acaaactctt cc                                  4652

<210> SEQ ID NO 76
<211> LENGTH: 4632
<212> TYPE: DNA
<213> ORGANISM: Artificial Sequence
<220> FEATURE:
<223> OTHER INFORMATION: Synthetic sequence

<400> SEQUENCE: 76
gtacgaaatt aatacgactc actataggga attgtgagcg ctcacaattc tctagaagaa      60
ggagatatac atatgaaata cctcttgcct acggcagccg ctggattgtt attactcgca     120
gcccaaccag cgatggctgc agagaccggt aaaatacata aggcttacta aagccagat     180 aacagtatgc gtatttgcgc gctgattttt gcggtataag aatatatact gatatctata     240
cccgaagtat gtcaaaaaga ggtgtgctat gcagtttaag gtttacacct ataaaagaga     300
```

```
gagccgttat cgtctgtttg tggatgtaca gagtgatatt attgacacgc ctgggcgacg    360
catggtgatc cccctggcca gtgcacgtct gctgtcagat aaagtctccc gtgaacttta    420
cccggtggtg catatcgggg atgaaagctg gcgcatgatg accaccgata tggccagtgt    480
gccagtctcc gttatcgggg aagaagtggc tgatctcagc caccgcgaaa atgacatcaa    540
aaacgccatt aacctgatgt tctggggaat ataacggccg gtctcaagcg atgacgcggc    600
aattcaacaa acgttagcca aaatgggcat caaaagcagc gatattcagc ccgcgcccgt    660
agctggcatg aagacagttc tgactaacag cggcgtgttg tacatcaccg atgatggtaa    720
acatatcatt caggggccaa tgtatgacgt tagcggcacg gctccggtca atgtcaccaa    780
taagatgctg ttaaagcagt tgaatgcggg atcccatcac caccatcatc actaaggtac    840
cgctgagcaa taactagcat aacccttgg ggcctctaaa cgggtcttga ggggtttttt     900
gctgaaagct tgaattctta gaaaaactca tcgagcatca aatgaaactg caatttattc    960
atatcaggat tatcaatacc atattttga aaaagccgtt tctgtaatga aggagaaaac    1020
tcaccgaggc agttccatag gatggcaaga tcctggtatc ggtctgcgat tccgactcgt    1080
ccaacatcaa tacaacctat taatttcccc tcgtcaaaaa taaggttatc aagtgagaaa    1140
tcaccatgag tgacgactga atccggtgag aatggcaaaa gcttatgcat ttctttccag    1200
acttgttcaa caggccagcc attacgctcg tcatcaaaat cactcgcatc aaccaaaccg    1260
ttattcattc gtgattgcgc ctgagcgaga cgaaatacgc ggtcgctgtt aaaaggacaa    1320
ttacaaacag gaatcgaatg caaccggcgc aggaacactg ccagcgcatc aacaatattt    1380
tcacctgaat caggatattc ttctaatacc tggaatgctg ttttcccggg gatcgcagtg    1440
gtgagtaacc atgcatcatc aggagtacgg ataaaatgct tgatggtcgg aagaggcata    1500
aattccgtca gccagtttag tctgaccatc tcatctgtaa catcattggc aacgctacct    1560
ttgccatgtt tcagaaacaa ctctggcgca tcgggcttcc catacaatcg atagattgtc    1620
gcacctgatt gcccgacatt atcgcgagcc catttatacc catataaatc agcatccatg    1680
ttggaattta atcgcggcct cgagcaagac gtttcccgtt gaatatggct cataacaccc    1740
cttgtattac tgtttatgta agcagacagt tttattgttc atgaccaaaa tcccttaacg    1800
tgagttttcg ttccactgag cgtcagaccc cgtagaaaag atcaaaggat cttcttgaga    1860 tcctttttt ctgcgcgtaa tctgctgctt gcaaacaaaa aaaccaccgc taccagcggt     1920
ggtttgtttg ccggatcaag agctaccaac tcttttttccg aaggtaactg gcttcagcag    1980
agcgcagata ccaaatactg tccttctagt gtagccgtag ttaggccacc acttcaagaa    2040
ctctgtagca ccgcctacat acctcgctct gctaatcctg ttaccagtgg ctgctgccag    2100
tggcgataag tcgtgtctta ccgggttgga ctcaagacga tagttaccgg ataaggcgca    2160
gcggtcgggc tgaacggggg gttcgtgcac acagcccagc ttggagcgaa cgacctacac    2220
cgaactgaga tacctacagc gtgagctatg agaaagcgcc acgcttcccg aagggagaaa    2280
ggcggacagg tatccggtaa gcggcagggt cggaacagga gagcgcacga gggagcttcc    2340
agggggaaac gcctggtatc tttatagtcc tgtcgggttt cgccacctct gacttgagcg    2400
tcgatttttg tgatgctcgt caggggggcg gagcctatgg aaaaacgcca gcaacgcggc    2460 cttttacgg ttcctggcct tttgctggcc ttttgctcac atgctctttc ctgcgttatc      2520
ccctgattct gtggataacc gtattaccgc ctttgagtga gctgataccg ctcgccgcag    2580
ccgaacgacc gagcgcagcg agtcagtgag cgaggaagcg gaagagcgcc tgatgcggta    2640
ttttctcctt acgcatctgt gcggtatttc acaccgcata tatggtgcac tctcagtaca    2700
```

```
atctgctctg atgccgcata gttaagccag tatacactcc gctatcgcta cgtgactggg    2760
tcatggctgc gccccgacac ccgccaacac ccgctgacgc ccctgacgg gcttgtctgc    2820 tcccggcatc cgcttacaga caagctgtga ccgtctccgg gagctgcatg tgtcagaggt    2880
tttcaccgtc atcaccgaaa cgcgcgaggc agctgcggta agctcatca gcgtggtcgt    2940 gaagcgattc acagatgtct gcctgttcat ccgcgtccag ctcgttgagt ttctccagaa    3000
gcgttaatgt ctggcttctg ataaagcggg ccatgttaag ggcggttttt tcctgtttgg    3060
tcactgatgc ctccgtgtaa gggggatttc tgttcatggg ggtaatgata ccgatgaaac    3120
gagagaggat gctcacgata cgggttactg atgatgaaca tgcccggtta ctggaacgtt    3180
gtgagggtaa acaactggcg gtatggatgc ggcgggacca gagaaaaatc accctaggtc    3240
actgcccgct ttccagtcgg gaaacctgtc gtgccagctg cattaatgaa tcggccaacg    3300
cgcggggaga ggcggtttgc gtattgggcg ccagggtggt ttttcttttc accagtgaga    3360
cgggcaacag ctgattgccc ttcaccgcct ggccctgaga gagttgcagc aagcggtcca    3420
cgctggtttg ccccagcagg cgaaaatcct gtttgatggt ggttaacggc gggatataac    3480
atgagctgtc ttcggtatcg tcgtatccca ctaccgagat atccgcacca acgcgcagcc    3540
cggactcggt aatggcgcgc attgcgccca gcgccatctg atcgttggca accagcatcg    3600
cagtgggaac gatgccctca ttcagcattt gcatggtttg ttgaaaaccg gacatggcac    3660
tccagtcgcc ttcccgttcc gctatcggct gaatttgatt gcgagtgaga tatttatgcc    3720
agccagccag acgcagacgc gccgagacag aacttaatgg cccgctaac agcgcgattt    3780 gctggtgacc caatgcgacc agatgctcca cgcccagtcg cgtaccgtct tcatgggaga    3840
aaataatact gttgatgggt gtctggtcag agacatcaag aaataacgcc ggaacattag    3900
tgcaggcagc ttccacagca atggcatcct ggtcatccag cggatagtta atgatcagcc    3960
cactgacgcg ttgcgcgaga agattgtgca ccgccgcttt acaggcttcg acgccgcttc    4020
gttctaccat cgacaccacc acgctggcac ccagttgatc ggcgcgagat ttaatcgccg    4080
cgacaatttg cgacggcgcg tgcagggcca gactggaggt ggcaacgcca atcagcaacg    4140
actgtttgcc cgccagttgt tgtgccacgc ggttgggaat gtaattcagc tccgccatcg    4200
ccgcttccac ttttttcccgc gttttcgcag aaacgtggct ggcctggttc accacgcggg    4260
aaacggtctg ataagagaca ccggcatact ctgcgacatc gtataacgtt actggtttca    4320
tgatatatct ccttaattga ctctcttccc gggcgctatc atgccatacc gcgaaaggtt    4380
ttgcgccatt cgatggtgta gatctcaaat aaaacgaaag gctcagtcga agactgggc    4440 ctttcgtttt atctgttgtt tgtcggtgaa cgctctcctg agtaggacaa atccgccggg    4500
agcggatttg aacgttgcga agcaacggcc cggagggtgg cgggcaggac gcccgccata    4560
aactgccagg catcaaatta agcagaaggc catcctgacg gatggccttt ttgcgtttct    4620
acaaactctt cc                                                       4632
```

<210> SEQ ID NO 77
<211> LENGTH: 4643
<212> TYPE: DNA
<213> ORGANISM: Artificial Sequence
<220> FEATURE:
<223> OTHER INFORMATION: Synthetic sequence

<400> SEQUENCE: 77

```
gtacgaaatt aatacgactc actataggga attgtgagcg ctcacaattc tctagaaata      60
attttgttta actttaagaa ggagatatac atatgaaaaa gatttggctg gcgctggctg     120
gtttagtttt agcgttcagc gcaagcgctg cagagaccgg taaaatacat aaggcttact     180
aaaagccaga taacagtatg cgtatttgcg cgctgatttt tgcggtataa gaatatatac     240
tgatatctat acccgaagta tgtcaaaaag aggtgtgcta tgcagtttaa ggtttacacc     300
tataaaagag agagccgtta tcgtctgttt gtggatgtac agagtgatat tattgacacg     360
cctgggcgac gcatggtgat ccccctggcc agtgcacgtc tgctgtcaga taaagtctcc     420
cgtgaacttt acccggtggt gcatatcggg gatgaaagct ggcgcatgat gaccaccgat     480
atggccagtg tgccagtctc cgttatcggg aagaagtgg ctgatctcag ccaccgcgaa      540
aatgacatca aaacgccat taacctgatg ttctggggaa tataacggcc ggtctcaagc      600
gatgacgcgc caattcaaca aacgttagcc aaaatgggca tcaaaagcag cgatattcag     660
cccgcgcccg tagctggcat gaagacagtt ctgactaaca gcggcgtgtt gtacatcacc     720
gatgatggta acatatcat tcaggggcca atgtatgacg ttagcggcac ggctccggtc      780
aatgtcacca ataagatgct gttaaagcag ttgaatgcgg gatcccatca ccaccatcat     840
cactaaggta ccgctgagca ataactagca taaccccttg gggcctctaa acgggtcttg     900
aggggttttt tgctgaaagc ttgaattctt agaaaaactc atcgagcatc aaatgaaact     960
gcaatttatt catatcagga ttatcaatac catattttg aaaaagccgt ttctgtaatg    1020
aaggagaaaa ctcaccgagg cagttccata ggatggcaag atcctggtat cggtctgcga    1080
ttccgactcg tccaacatca atacaaccta ttaatttccc ctcgtcaaaa ataaggttat    1140
caagtgagaa atcaccatga gtgacgactg aatccggtga gaatggcaaa agcttatgca    1200
tttctttcca gacttgttca acaggccagc cattacgctc gtcatcaaaa tcactcgcat    1260
caaccaaacc gttattcatt cgtgattgcg cctgagcgag acgaaatacg cggtcgctgt    1320
taaaaggaca attacaaaca ggaatcgaat gcaaccggcg caggaacact gccagcgcat    1380
caacaatatt ttcacctgaa tcaggatatt cttctaatac ctggaatgct gtttttcccgg   1440
ggatcgcagt ggtgagtaac catgcatcat caggagtacg gataaaatgc ttgatggtcg    1500
gaagaggcat aaattccgtc agccagttta gtctgaccat ctcatctgta acatcattgg    1560
caacgctacc tttgccatgt ttcagaaaca actctggcgc atcgggcttc ccatacaatc    1620
gatagattgt cgcacctgat tgcccgacat tatcgcgagc ccatttatac ccatataaat    1680
cagcatccat gttggaattt aatcgcggcc tcgagcaaga cgtttcccgt tgaatatggc    1740
tcataacacc ccttgtatta ctgtttatgt aagcagacag ttttattgtt catgaccaaa    1800
atcccttaac gtgagttttc gttccactga gcgtcagacc ccgtagaaaa gatcaaagga    1860
tcttcttgag atccttttttt tctgcgcgta atctgctgct tgcaaacaaa aaaaccaccg    1920
ctaccagcgg tggtttgttt gccggatcaa gagctaccaa ctcttttttcc gaaggtaact    1980
ggcttcagca gagcgcagat accaaatact gtccttctag tgtagccgta gttaggccac    2040
cacttcaaga actctgtagc accgcctaca tacctcgctc tgctaatcct gttaccagtg    2100
gctgctgcca gtggcgataa gtcgtgtctt accgggttgg actcaagacg atagttaccg    2160
gataaggcgc agcggtcggg ctgaacgggg gttcgtgca cacagcccag cttggagcga    2220
acgacctaca ccgaactgag atacctacag cgtgagctat gagaaagcgc cacgcttccc    2280
```

```
gaagggagaa aggcggacag gtatccggta agcggcaggg tcggaacagg agagcgcacg    2340
agggagcttc caggggaaa cgcctggtat ctttatagtc ctgtcgggtt tcgccacctc    2400
tgacttgagc gtcgatttt gtgatgctcg tcagggggc ggagcctatg gaaaaacgcc    2460
agcaacgcgg cctttttacg gttcctggcc ttttgctggc cttttgctca catgctcttt    2520
cctgcgttat cccctgattc tgtggataac cgtattaccg cctttgagtg agctgatacc    2580
gctcgccgca gccgaacgac cgagcgcagc gagtcagtga gcgaggaagc ggaagagcgc    2640
ctgatgcggt attttctcct tacgcatctg tgcggtattt cacaccgcat atatggtgca    2700
ctctcagtac aatctgctct gatgccgcat agttaagcca gtatacactc cgctatcgct    2760
acgtgactgg gtcatggctg cgccccgaca cccgccaaca cccgctgacg cgccctgacg    2820
ggcttgtctg ctcccggcat ccgcttacag acaagctgtg accgtctccg ggagctgcat    2880
gtgtcagagg ttttcaccgt catcaccgaa acgcgcgagg cagctgcggt aaagctcatc    2940
agcgtggtcg tgaagcgatt cacagatgtc tgcctgttca tccgcgtcca gctcgttgag    3000
tttctccaga agcgttaatg tctggcttct gataaagcgg ccatgttaa gggcggtttt    3060
ttcctgtttg gtcactgatg cctccgtgta agggggattt ctgttcatgg gggtaatgat    3120
accgatgaaa cgagagagga tgctcacgat acgggttact gatgatgaac atgcccggtt    3180
actggaacgt tgtgagggta acaactggc ggtatggatg cggcgggacc agagaaaaat    3240
caccctaggt cactgcccgc tttccagtcg ggaaacctgt cgtgccagct gcattaatga    3300
atcggccaac gcgcggggag aggcggtttg cgtattgggc gccagggtgg tttttctttt    3360
caccagtgag acgggcaaca gctgattgcc cttcaccgcc tggccctgag agagttgcag    3420
caagcggtcc acgctggttt gccccagcag gcgaaaatcc tgtttgatgg tggttaacgg    3480
cgggatataa catgagctgt cttcggtatc gtcgtatccc actaccgaga tatccgcacc    3540
aacgcgcagc ccggactcgg taatggcgcg cattgcgccc agcgccatct gatcgttggc    3600
aaccagcatc gcagtgggaa cgatgccctc attcagcatt tgcatggttt gttgaaaacc    3660
ggacatggca ctccagtcgc cttcccgttc cgctatcggc tgaatttgat tgcgagtgag    3720
atatttatgc cagccagcca gacgcagacg cgccgagaca gaacttaatg ggcccgctaa    3780
cagcgcgatt tgctggtgac ccaatgcgac cagatgctcc acgcccagtc gcgtaccgtc    3840
ttcatgggag aaaataatac tgttgatggg tgtctggtca gagacatcaa gaaataacgc    3900
cggaacatta gtgcaggcag cttccacagc aatggcatcc tggtcatcca gcggatagtt    3960
aatgatcagc ccactgacgc gttgcgcgag aagattgtgc accgccgctt tacaggcttc    4020
gacgccgctt cgttctacca tcgacaccac cacgctggca cccagttgat cggcgcgaga    4080
tttaatcgcc gcgacaattt gcgacggcgc gtgcagggcc agactggagg tggcaacgcc    4140
aatcagcaac gactgtttgc ccgccagttg ttgtgccacg cggttgggaa tgtaattcag    4200
ctccgccatc gccgcttcca cttttttccg cgttttcgca gaaacgtggc tggcctggtt    4260
caccacgcgg gaaacggtct gataagagac accggcatac tctgcgacat cgtataacgt    4320
tactggtttc atgatatatc tccttaattg actctcttcc cggcgctat catgccatac    4380
cgcgaaaggt tttgcgccat tcgatggtgt agatctcaaa taaaacgaaa ggctcagtcg    4440
aaagactggg ccttttcgttt tatctgttgt ttgtcggtga acgctctcct gagtaggaca    4500
aatccgccgg gagcggattt gaacgttgcg aagcaacggc ccggagggtg cgggcagga    4560
cgcccgccat aaactgccag gcatcaaatt aagcagaagg ccatcctgac ggatggcctt    4620
tttgcgtttc tacaaactct tcc                                          4643
```

<210> SEQ ID NO 78
<211> LENGTH: 4623
<212> TYPE: DNA
<213> ORGANISM: Artificial Sequence
<220> FEATURE:
<223> OTHER INFORMATION: Synthetic sequence

<400> SEQUENCE: 78

```
gtacgaaatt aatacgactc actatagggga attgtgagcg ctcacaattc tctagaagaa      60
ggagatatac atatgaaaaa gatttggctg gcgctggctg gtttagtttt agcgttcagc     120
gcaagcgctg cagagaccgg taaaatacat aaggcttact aaaagccaga taacagtatg     180
cgtatttgcg cgctgatttt tgcggtataa gaatatatac tgatatctat acccgaagta     240
tgtcaaaaag aggtgtgcta tgcagtttaa ggtttacacc tataaagag agagccgtta      300
tcgtctgttt gtggatgtac agagtgatat tattgacacg cctgggcgac gcatggtgat     360
ccccctggcc agtgcacgtc tgctgtcaga taaagtctcc cgtgaacttt acccggtggt     420
gcatatcggg gatgaaagct ggcgcatgat gaccaccgat atggccagtg tgccagtctc     480
cgttatcggg gaagaagtgg ctgatctcag ccaccgcgaa aatgacatca aaaacgccat     540
taacctgatg ttctggggaa tataacggcc ggtctcaagc gatgacgcgg caattcaaca     600
aacgttagcc aaaatgggca tcaaaagcag cgatattcag cccgcgcccg tagctggcat     660
gaagacagtt ctgactaaca gcggcgtgtt gtacatcacc gatgatggta acatatcat      720
tcagggggcca atgtatgacg ttagcggcac ggctccggtc aatgtcacca ataagatgct     780
gttaaagcag ttgaatgcgg gatcccatca ccaccatcat cactaaggta ccgctgagca     840
ataactagca taacccccttg gggcctctaa acgggtcttg aggggttttt tgctgaaagc     900
ttgaattctt agaaaaactc atcgagcatc aaatgaaact gcaatttatt catatcagga     960
ttatcaatac catattttg aaaaagccgt ttctgtaatg aaggagaaaa ctcaccgagg      1020
cagttccata ggatggcaag atcctggtat cggtctgcga ttccgactcg tccaacatca     1080
atacaaccta ttaatttccc ctcgtcaaaa ataaggttat caagtgagaa atcaccatga     1140
gtgacgactg aatccggtga agtggcaaa agcttatgca tttctttcca gacttgttca     1200
acaggccagc cattacgctc gtcatcaaaa tcactcgcat caaccaaacc gttattcatt     1260
cgtgattgcg cctgagcgag acgaaatacg cggtcgctgt taaaaggaca attacaaaca     1320
ggaatcgaat gcaaccggcg caggaacact gccagcgcat caacaatatt ttcacctgaa     1380
tcaggatatt cttctaatac ctggaatgct gtttttccgg ggatcgcagt ggtgagtaac     1440
catgcatcat caggagtacg gataaaatgc ttgatggtcg aagaggcat aaattccgtc     1500
agccagttta gtctgaccat ctcatctgta acatcattgg caacgctacc tttgccatgt     1560
ttcagaaaca actctggcgc atcgggcttc ccatacaatc gatagattgt cgcacctgat     1620
tgcccgacat tatcgcgagc ccatttatac ccatataaat cagcatccat gttggaattt     1680
aatcgcggcc tcgagcaaga cgtttcccgt tgaatatggc tcataacacc ccttgtatta     1740
ctgtttatgt aagcagacag ttttattgtt catgaccaaa atcccttaac gtgagttttc     1800
gttccactga gcgtcagacc ccgtagaaaa gatcaaagga tcttcttgag atcctttttt     1860
tctgcgcgta atctgctgct tgcaaacaaa aaaaccaccg ctaccagcgg tggtttgttt     1920
gccggatcaa gagctaccaa ctcttttcc gaaggtaact ggcttcagca gagcgcagat     1980
accaaatact gtccttctag tgtagccgta gttaggccac cacttcaaga actctgtagc     2040
```

```
accgcctaca tacctcgctc tgctaatcct gttaccagtg gctgctgcca gtggcgataa    2100
gtcgtgtctt accgggttgg actcaagacg atagttaccg gataaggcgc agcggtcggg    2160
ctgaacgggg ggttcgtgca cacagcccag cttggagcga acgacctaca ccgaactgag    2220
atacctacag cgtgagctat gagaaagcgc cacgcttccc gaagggagaa aggcggacag    2280
gtatccggta agcggcaggg tcggaacagg agagcgcacg agggagcttc caggggggaaa   2340
cgcctggtat ctttatagtc ctgtcgggtt tcgccacctc tgacttgagc gtcgattttt    2400
gtgatgctcg tcagggggc ggagcctatg gaaaaacgcc agcaacgcgg cctttttacg     2460
gttcctggcc ttttgctggc cttttgctca catgctcttt cctgcgttat cccctgattc    2520
tgtggataac cgtattaccg cctttgagtg agctgatacc gctcgccgca gccgaacgac    2580
cgagcgcagc gagtcagtga gcgaggaagc ggaagagcgc ctgatgcggt attttctcct    2640
tacgcatctg tgcggtattt cacaccgcat atatggtgca ctctcagtac aatctgctct    2700
gatgccgcat agttaagcca gtatacactc cgctatcgct acgtgactgg gtcatggctg    2760
cgccccgaca cccgccaaca cccgctgacg cgccctgacg gcttgtctg ctcccggcat     2820
ccgcttacag acaagctgtg accgtctccg ggagctgcat gtgtcagagg ttttcaccgt    2880
catcaccgaa acgcgcgagg cagctgcggt aaagctcatc agcgtggtcg tgaagcgatt    2940
cacagatgtc tgcctgttca tccgcgtcca gctcgttgag tttctccaga agcgttaatg    3000
tctggcttct gataaagcgg gccatgttaa gggcggtttt ttcctgtttg gtcactgatg    3060
cctccgtgta aggggatttt ctgttcatgg gggtaatgat accgatgaaa cgagagagga    3120
tgctcacgat acgggttact gatgatgaac atgcccggtt actggaacgt tgtgagggta    3180
aacaactggc ggtatggatg cggcgggacc agagaaaaat caccctaggt cactgcccgc    3240
tttccagtcg ggaaacctgt cgtgccagct gcattaatga atcggccaac gcgcggggag    3300
aggcggtttg cgtattgggc gccagggtgg ttttcttttt caccagtgag acgggcaaca    3360
gctgattgcc cttcaccgcc tggccctgag agagttgcag caagcggtcc acgctggttt    3420
gccccagcag gcgaaaatcc tgtttgatgg tggttaacgg cgggatataa catgagctgt    3480
cttcggtatc gtcgtatccc actaccgaga tatccgcacc aacgcgcagc ccggactcgg    3540
taatggcgcg cattgcgccc agcgccatct gatcgttggc aaccagcatc gcagtgggaa    3600
cgatgccctc attcagcatt tgcatggttt gttgaaaacc ggacatggca ctccagtcgc    3660
cttcccgttc cgctatcggc tgaatttgat tgcgagtgag atatttatgc cagccagcca    3720
gacgcagacg cgccgagaca gaacttaatg ggcccgctaa cagcgcgatt tgctggtgac    3780
ccaatgcgac cagatgctcc acgcccagtc gcgtaccgtc ttcatgggag aaaataatac    3840
tgttgatggg tgtctggtca gagacatcaa gaaataacgc cggaacatta gtgcaggcag    3900
cttccacagc aatggcatcc tggtcatcca gcggatagtt aatgatcagc ccactgacgc    3960
gttgcgcgag aagattgtgc accgccgctt tacaggcttc gacgccgctt cgttctacca    4020
tcgacaccac cacgctggca cccagttgat cggcgcgaga tttaatcgcc gcgacaattt    4080
gcgacggcgc gtgcagggcc agactggagg tggcaacgcc aatcagcaac gactgtttgc    4140
ccgccagttg ttgtgccacg cggttgggaa tgtaattcag ctccgccatc gccgcttcca    4200
ctttttcccg cgttttcgca gaaacgtggc tggcctggtt caccacgcgg gaaacggtct    4260
gataagagac accggcatac tctgcgacat cgtataacgt tactggtttc atgatatatc    4320
tccttaattg actctcttcc cgggcgctat catgccatac cgcgaaaggt tttgcgccat    4380
tcgatggtgt agatctcaaa taaaacgaaa ggctcagtcg aaagactggg cctttcgttt    4440
```

```
tatctgttgt tgtcggtga acgctctcct gagtaggaca atccgccgg gagcggattt    4500 gaacgttgcg aagcaacggc ccggagggtg gcgggcagga cgcccgccat aaactgccag    4560
gcatcaaatt aagcagaagg ccatcctgac ggatggcctt tttgcgtttc tacaaactct    4620
tcc                                                                   4623
```

<210> SEQ ID NO 79
<211> LENGTH: 17
<212> TYPE: DNA
<213> ORGANISM: Artificial Sequence
<220> FEATURE:
<223> OTHER INFORMATION: Synthetic sequence

<400> SEQUENCE: 79

```
taaggagact attaatg                                                    17
```

<210> SEQ ID NO 80
<211> LENGTH: 17
<212> TYPE: DNA
<213> ORGANISM: Artificial Sequence
<220> FEATURE:
<223> OTHER INFORMATION: Synthetic sequence

<400> SEQUENCE: 80

```
taaggagact taatatg                                                    17
```

<210> SEQ ID NO 81
<211> LENGTH: 3257
<212> TYPE: DNA
<213> ORGANISM: Artificial Sequence
<220> FEATURE:
<223> OTHER INFORMATION: Synthetic sequence

<400> SEQUENCE: 81

```
tgagcgcaac gcaattaatg taagttagct cactcattag gcaccccagg ctttacactt      60
tatgcttccg gctcgtataa tgtgtggaat tgtgagcgga taacaatttc acacaggaaa     120
cagctatgac catgattacg gattcactgg ccgtcgtttt acaacgtcgt gactgggaaa     180
accctggcgt tacccaactt aatcgccttg cagcacatcc ccctttcgcc agctggcgta     240
atagcgaaga ggcccgcacc gatcgccctt cccaacagtt gcgcagcctg aatggcgaat     300
ggcgctttgc ctggtttccg gcaccagaag cggtgccgga agctggctg gagtgcgatc      360 ttcctgaggc cgatactgtc gtcgtcccct caaactggca gatgcacggt tacgatgcgc     420
ccatctacac caacgtgacc tatcccatta cggtcaatcc gccgtttgtt cccacggaga     480
atccgacggg ttgttactcg ctcacattta atgttgatga agctggcta caggaaggcc      540 agacgcgaat tatttttgat ggcgtcggga tctgatccgg atttactaac tggaagaggc     600
actaaatgaa cacgattaac atcgctaaga acgacttctc tgacatcgaa ctggctgcta     660
tcccgttcaa cactctggct gaccattacg gtgagcgttt agctcgcgaa cagttggccc     720
ttgagcatga gtcttacgag atgggtgaag cacgcttccg caagatgttt gagcgtcaac     780
ttaaagctgg tgaggttgcg gataacgctg ccgccaagcc tctcatcact accctactcc     840
ctaagatgat tgcacgcatc aacgactggt ttgaggaagt gaaagctaag cgcggcaagc     900
gcccgacagc cttccagttc ctgcaagaaa tcaagccgga agccgtagcg tacatcacca     960
ttaagaccac tctggcttgc ctaaccagtc tgacaatac aaccgttcag gctgtagcaa      1020
gcgcaatcgg tcgggccatt gaggacgagg ctcgcttcgg tcgtatccgt gaccttgaag     1080
```

```
ctaagcactt caagaaaaac gttgaggaac aactcaacaa gcgcgtaggg cacgtctaca   1140
agaaagcatt tatgcaagtt gtcgaggctg acatgctctc taagggtcta ctcggtggcg   1200
aggcgtggtc ttcgtggcat aaggaagact ctattcatgt aggagtacgc tgcatcgaga   1260
tgctcattga gtcaaccgga atggttagct tacaccgcca aaatgctggc gtagtaggtc   1320
aagactctga gactatcgaa ctcgcacctg aatacgctga ggctatcgca acccgtgcag   1380
gtgcgctggc tggcatctct ccgatgttcc aaccttgcgt agttcctcct aagccgtgga   1440
ctggcattac tggtggtggc tattgggcta acggtcgtcg tcctctggcg ctggtgcgta   1500
ctcacagtaa gaaagcactg atgcgctacg aagacgttta catgcctgag gtgtacaaag   1560
cgattaacat tgcgcaaaac accgcatgga aaatcaacaa gaaagtccta gcggtcgcca   1620
acgtaatcac caagtggaag cattgtccgg tcgaggacat ccctgcgatt gagcgtgaag   1680
aactcccgat gaaaccggaa gacatcgaca tgaatcctga ggctctcacc gcgtggaaac   1740
gtgctgccgc tgctgtgtac cgcaaggaca aggctcgcaa gtctcgccgt atcagccttg   1800
agttcatgct tgagcaagcc aataagtttg ctaaccataa ggccatctgg ttcccttaca   1860
acatggactg gcgcggtcgt gtttacgctg tgtcaatgtt caacccgcaa ggtaacgata   1920
tgaccaaagg actgcttacg ctggcgaaag gtaaaccaat cggtaaggaa ggttactact   1980
ggctgaaaat ccacggtgca aactgtgcgg gtgtcgataa ggttccgttc cctgagcgca   2040
tcaagttcat tgaggaaaac cacgagaaca tcatggcttg cgctaagtct ccactggaga   2100
acacttggtg ggctgagcaa gattctccgt tctgcttcct tgcgttctgc tttgagtacg   2160
ctggggtaca gcaccacggc ctgagctata actgctccct tccgctggcg tttgacgggt   2220
cttgctctgg catccagcac ttctccgcga tgctccgaga tgaggtaggt ggtcgcgcgg   2280
ttaacttgct tcctagtgaa accgttcagg acatctacgg gattgttgct aagaaagtca   2340
acgagattct acaagcagac gcaatcaatg ggaccgataa cgaagtagtt accgtgaccg   2400
atgagaacac tggtgaaatc tctgagaaag tcaagctggg cactaaggca ctggctggtc   2460
aatggctggc ttacggtgtt actcgcagtg tgactaagcg ttcagtcatg acgctggctt   2520
acgggtccaa agagttcggc ttccgtcaac aagtgctgga agataccatt cagccagcta   2580
ttgattccgg caagggtctg atgttcactc agccgaatca ggctgctgga tacatggcta   2640
agctgatttg ggaatctgtg agcgtgacgg tggtagctgc ggttgaagca atgaactggc   2700
ttaagtctgc tgctaagctg ctggctgctg aggtcaaaga taagaagact ggagagattc   2760
ttcgcaagcg ttgcgctgtg cattgggtaa ctcctgatgg tttccctgtg tggcaggaat   2820
acaagaagcc tattcagacg cgcttgaacc tgatgttcct cggtcagttc cgcttacagc   2880
ctaccattaa caccaacaaa gatagcgaga ttgatgcaca caaacaggag tctggtatcg   2940
ctcctaactt tgtacacagc caagacggta gccaccttcg taagactgta gtgtgggcac   3000 acgaaagta cggaatcgaa tcttttgcac tgattcacga ctccttcggt accattccgg   3060
ctgacgctgc gaacctgttc aaagcagtgc gcgaaactat ggttgacaca tatgagtctt   3120
gtgatgtact ggctgatttc tacgaccagt tcgctgacca gttgcacgag tctcaattgg   3180
acaaaatgcc agcacttccg gctaaaggta acttgaacct ccgtgacatc ttagagtcgg   3240
acttcgcgtt cgcgtaa                                                 3257
```

<210> SEQ ID NO 82
<211> LENGTH: 3257
<212> TYPE: DNA
<213> ORGANISM: Artificial Sequence
<220> FEATURE:
<223> OTHER INFORMATION: Synthetic sequence

<400> SEQUENCE: 82

```
tgagcgcaac gcaattaatg tgagttagct cactcattag gcaccccagg ctttacactt      60
tatgcttccg gctcgtatgt tgtgtgaaat tgtgagcgga taacaatttc acacaggaaa     120
cagctatgac catgattacg gattcactgg ccgtcgtttt acaacgtcgt gactgggaaa     180
accctggcgt tacccaactt aatcgccttg cagcacatcc ccctttcgcc agctggcgta     240
atagcgaaga ggcccgcacc gatcgccctt cccaacagtt gcgcagcctg aatggcgaat     300
ggcgctttgc ctggtttccg gcaccagaag cggtgccgga agctggctg gagtgcgatc      360
ttcctgaggc cgatactgtc gtcgtcccct caaactggca gatgcacggt tacgatgcgc     420
ccatctacac caacgtgacc tatcccatta cggtcaatcc gccgtttgtt cccacgaga      480
atccgacggg ttgttactcg ctcacattta atgttgatga agctggcta caggaaggcc      540
agacgcgaat tattttgat ggcgtcggga tctgatccgg atttactaac tggaagaggc      600
actaaatgaa cacgattaac atcgctaaga acgacttctc tgacatcgaa ctggctgcta     660
tcccgttcaa cactctggct gaccattacg gtgagcgttt agctcgcgaa cagttggccc     720
ttgagcatga gtcttacgag atgggtgaag cacgcttccg caagatgttt gagcgtcaac     780
ttaaagctgg tgaggttgcg gataacgctg ccgccaagcc tctcatcact accctactcc     840
ctaagatgat tgcacgcatc aacgactggt ttgaggaagt gaaagctaag cgcggcaagc     900
gcccgacagc cttccagttc ctgcaagaaa tcaagccgga agccgtagcg tacatcacca     960
ttaagaccac tctggcttgc ctaaccagtg ctgacaatac aaccgttcag gctgtagcaa    1020
gcgcaatcgg tcgggccatt gaggacgagg ctcgcttcgg tcgtatccgt gacctttgaag   1080
ctaagcactt caagaaaaac gttgaggaac aactcaacaa gcgcgtaggg cacgtctaca    1140
agaaagcatt tatgcaagtt gtcgaggctg acatgctctc taagggtcta ctcggtggcg    1200
aggcgtggtc ttcgtggcat aaggaagact ctattcatgt aggagtacgc tgcatcgaga    1260
tgctcattga gtcaaccgga atggttagct tacaccgcca aaatgctggc gtagtaggtc    1320
aagactctga gactatcgaa ctcgcacctg aatacgctga ggctatcgca acccgtgcag    1380
gtgcgctggc tggcatctct ccgatgttcc aaccttgcgt agttcctcct aagccgtgga    1440
ctggcattac tggtggtggc tattgggcta acggtcgtcg tcctctggcg ctggtgcgta    1500
ctcacagtaa gaaagcactg atgcgctacg aagacgttta catgcctgag gtgtacaaag    1560
cgattaacat tgcgcaaaac accgcatgga aaatcaacaa gaaagtccta gcggtcgcca    1620
acgtaatcac caagtggaag cattgtccgg tcgaggacat ccctgcgatt gagcgtgaag    1680
aactcccgat gaaaccggaa gacatcgaca tgaatcctga ggctctcacc gcgtggaaac    1740
gtgctgccgc tgctgtgtac cgcaaggaca aggctcgcaa gtctcgccgt atcagccttg    1800
agttcatgct tgagcaagcc aataagtttg ctaaccataa ggccatctgg ttcccttaca    1860
acatggactg gcgcggtcgt gtttacgctg tgtcaatgtt caacccgcaa ggtaacgata    1920
tgaccaaagg actgcttacg ctggcgaaag gtaaaccaat cggtaaggaa ggttactact    1980
ggctgaaaat ccacggtgca aactgtgcgg gtgtcgataa ggttccgttc cctgagcgca    2040
tcaagttcat tgaggaaaac cacgagaaca tcatggcttg cgctaagtct ccactggaga    2100
acacttggtg ggctgagcaa gattctccgt tctgcttcct tgcgttctgc tttgagtacg    2160
ctggggtaca gcaccacggc ctgagctata actgctccct tccgctggcg tttgacgggt    2220
```

```
cttgctctgg catccagcac ttctccgcga tgctccgaga tgaggtaggt ggtcgcgcgg    2280
ttaacttgct tcctagtgaa accgttcagg acatctacgg gattgttgct aagaaagtca    2340
acgagattct acaagcagac gcaatcaatg ggaccgataa cgaagtagtt accgtgaccg    2400 atgaaacac tggtgaaatc tctgagaaag tcaagctggg cactaaggca ctggctggtc     2460
aatggctggc ttacggtgtt actcgcagtg tgactaagcg ttcagtcatg acgctggctt    2520
acgggtccaa agagttcggc ttccgtcaac aagtgctgga agataccatt cagccagcta    2580
ttgattccgg caagggtctg atgttcactc agccgaatca ggctgctgga tacatggcta    2640
agctgatttg ggaatctgtg agcgtgacgg tggtagctgc ggttgaagca atgaactggc    2700
ttaagtctgc tgctaagctg ctggctgctg aggtcaaaga taagaagact ggagagattc    2760
ttcgcaagcg ttgcgctgtg cattgggtaa ctcctgatgg tttccctgtg tggcaggaat    2820
acaagaagcc tattcagacg cgcttgaacc tgatgttcct cggtcagttc cgcttacagc    2880
ctaccattaa caccaacaaa gatagcgaga ttgatgcaca caaacaggag tctggtatcg    2940
ctcctaactt tgtacacagc caagacgta gccaccttcg taagactgta gtgtgggcac      3000
acgagaagta cggaatcgaa tcttttgcac tgattcacga ctccttcggt accattccgg    3060
ctgacgctgc gaacctgttc aaagcagtgc gcgaaactat ggttgacaca tatgagtctt    3120
gtgatgtact ggctgatttc tacgaccagt tcgctgacca gttgcacgag tctcaattgg    3180
acaaaatgcc agcacttccg gctaaaggta acttgaacct ccgtgacatc ttagagtcgg    3240
acttcgcgtt cgcgtaa                                                   3257

<210> SEQ ID NO 83
<211> LENGTH: 3257
<212> TYPE: DNA
<213> ORGANISM: Artificial Sequence
<220> FEATURE:
<223> OTHER INFORMATION: Synthetic sequence

<400> SEQUENCE: 83
tgagcgcaac gcaattaatg taagttagct cactcattag gcaccccagg ctttacactt      60
tatgcttccg gctcgtatgt tgtgtgaaat tgtgagcgga taacaatttc acacaggaaa     120
cagctatgac catgattacg gattcactgg ccgtcgtttt acaacgtcgt gactgggaaa     180
accctggcgt tacccaactt aatcgccttg cagcacatcc ccctttcgcc agctggcgta    240
atagcgaaga ggcccgcacc gatcgccctt cccaacagtt gcgcagcctg aatggcgaat    300
ggcgctttgc ctggtttccg gcaccagaag cggtgccgga agctggctg gagtgcgatc      360 ttcctgaggc cgatactgtc gtcgtcccct caaactggca gatgcacggt tacgatgcgc    420
ccatctacac caacgtgacc tatcccatta cggtcaatcc gccgtttgtt cccacgagga    480
atccgacggg ttgttactcg ctcacattta atgttgatga agctggcta caggaaggcc      540 agacgcgaat tatttttgat ggcgtcggga tctgatccgg atttactaac tggaagaggc    600
actaaatgaa cacgattaac atcgctaaga acgacttctc tgacatcgaa ctggctgcta    660
tcccgttcaa cactctggct gaccattacg gtgagcgttt agctcgcgaa cagttggccc    720
ttgagcatga gtcttacgag atgggtgaag cacgcttccg caagatgttt gagcgtcaac    780
ttaaagctgg tgaggttgcg gataacgctg ccgccaagcc tctcatcact accctactcc    840
ctaagatgat tgcacgcatc aacgactggt tgaggaagt gaaagctaag cgcggcaagc     900
gcccgacagc cttccagttc ctgcaagaaa tcaagccgga agccgtagcg tacatcacca    960
ttaagaccac tctggcttgc ctaaccagtg ctgacaatac aaccgttcag gctgtagcaa    1020
```

```
gcgcaatcgg tcgggccatt gaggacgagg ctcgcttcgg tcgtatccgt gaccttgaag    1080
ctaagcactt caagaaaaac gttgaggaac aactcaacaa gcgcgtaggg cacgtctaca    1140
agaaagcatt tatgcaagtt gtcgaggctg acatgctctc taagggtcta ctcggtggcg    1200
aggcgtggtc ttcgtggcat aaggaagact ctattcatgt aggagtacgc tgcatcgaga    1260
tgctcattga gtcaaccgga atggttagct tacaccgcca aaatgctggc gtagtaggtc    1320
aagactctga gactatcgaa ctcgcacctg aatacgctga ggctatcgca acccgtgcag    1380
gtgcgctggc tggcatctct ccgatgttcc aaccttgcgt agttcctcct aagccgtgga    1440
ctggcattac tggtggtggc tattgggcta acggtcgtcg tcctctggcg ctggtgcgta    1500
ctcacagtaa gaaagcactg atgcgctacg aagacgttta catgcctgag gtgtacaaag    1560
cgattaacat tgcgcaaaac accgcatgga aaatcaacaa gaaagtccta gcggtcgcca    1620
acgtaatcac caagtggaag cattgtccgg tcgaggacat ccctgcgatt gagcgtgaag    1680
aactcccgat gaaaccggaa gacatcgaca tgaatcctga ggctctcacc gcgtggaaac    1740
gtgctgccgc tgctgtgtac cgcaaggaca aggctcgcaa gtctcgccgt atcagccttg    1800
agttcatgct tgagcaagcc aataagtttg ctaaccataa ggccatctgg ttcccttaca    1860
acatggactg gcgcggtcgt gtttacgctg tgtcaatgtt caacccgcaa ggtaacgata    1920
tgaccaaagg actgcttacg ctggcgaaag gtaaaccaat cggtaaggaa ggttactact    1980
ggctgaaaat ccacggtgca aactgtgcgg gtgtcgataa ggttccgttc cctgagcgca    2040
tcaagttcat tgaggaaaac cacgagaaca tcatggcttg cgctaagtct ccactggaga    2100
acacttggtg ggctgagcaa gattctccgt tctgcttcct tgcgttctgc tttgagtacg    2160
ctggggtaca gcaccacggc ctgagctata actgctccct tccgctggcg tttgacgggt    2220
cttgctctgg catccagcac ttctccgcga tgctccgaga tgaggtaggt ggtcgcgcgg    2280
ttaacttgct tcctagtgaa accgttcagg acatctacgg gattgttgct aagaaagtca    2340
acgagattct acaagcagac gcaatcaatg ggaccgataa cgaagtagtt accgtgaccg    2400 atgaaacac tggtgaaatc tctgagaaag tcaagctggg cactaaggca ctggctggtc    2460
aatggctggc ttacggtgtt actcgcagtg tgactaagcg ttcagtcatg acgctggctt    2520
acgggtccaa agagttcggc ttccgtcaac aagtgctgga agataccatt cagccagcta    2580
ttgattccgg caagggtctg atgttcactc agccgaatca ggctgctgga tacatggcta    2640
agctgatttg ggaatctgtg agcgtgacgg tggtagctgc ggttgaagca atgaactggc    2700
ttaagtctgc tgctaagctg ctggctgctg aggtcaaaga taagaagact ggagagattc    2760
ttcgcaagcg ttgcgctgtg cattgggtaa ctcctgatgg tttccctgtg tggcaggaat    2820
acaagaagcc tattcagacg cgcttgaacc tgatgttcct cggtcagttc cgcttacagc    2880
ctaccattaa caccaacaaa gatagcgaga ttgatgcaca caaacaggag tctggtatcg    2940
ctcctaactt tgtacacagc caagacggta gccaccttcg taagactgta gtgtgggcac    3000
acgagaagta cggaatcgaa tcttttgcac tgattcacga ctccttcggt accattccgg    3060
ctgacgctgc gaacctgttc aaagcagtgc gcgaaactat ggttgacaca tatgagtctt    3120
gtgatgtact ggctgatttc tacgaccagt tcgctgacca gttgcacgag tctcaattgg    3180
acaaaatgcc agcacttccg gctaaaggta acttgaacct ccgtgacatc ttagagtcgg    3240
acttcgcgtt cgcgtaa                                                  3257
```

<210> SEQ ID NO 84

<211> LENGTH: 3257
<212> TYPE: DNA
<213> ORGANISM: Artificial Sequence
<220> FEATURE:
<223> OTHER INFORMATION: Synthetic sequence

<400> SEQUENCE: 84

| | | | | |
|---|---|---|---|---|
| tgagcgcaac | gcaattaatg | tgagttagct | cactcattag | gcaccccagg | ctttacactt | 60 |
| tatgcttccg | gctcgtatgt | tgtgtgaaat | tgtgagcgga | taacaatttc | acacaggaaa | 120 |
| cagctatgac | catgattacg | gattcactgg | ccgtcgtttt | acaacgtcgt | gactgggaaa | 180 |
| accctggcgt | tacccaactt | aatcgccttg | cagcacatcc | ccctttcgcc | agctggcgta | 240 |
| atagcgaaga | ggcccgcacc | gatcgccctt | cccaacagtt | gcgcagcctg | aatggcgaat | 300 |
| ggcgctttgc | ctggtttccg | gcaccagaag | cggtgccgga | aagctggctg | gagtgcgatc | 360 |
| ttcctgaggc | cgatactgtc | gtcgtcccct | caaactggca | gatgcacggt | tacgatgcgc | 420 |
| ccatctacac | caacgtgacc | tatcccatta | cggtcaatcc | gccgtttgtt | cccacggaga | 480 |
| atccgacggg | ttgttactcg | ctcacattta | atgttgatga | aagctggcta | caggaaggcc | 540 |
| agacgcgaat | tatttttgat | ggcgtcggga | tctgatccgg | atttactaac | tggaagaggc | 600 |
| actaaatgaa | cacgattaac | atcgctaaga | acgacttctc | tgacatcgaa | ctggctgcta | 660 |
| tcccgttcaa | cactctggct | gaccattacg | gtgagcgttt | agctcgcgaa | cagttggccc | 720 |
| ttgagcatga | gtcttacgag | atgggtgaag | cacgcttccg | caagatgttt | gagcgtcaac | 780 |
| ttaaagctgg | tgaggttgcg | gataacgctg | ccgccaagcc | tctcatcact | accctactcc | 840 |
| ctaagatgat | tgcacgcatc | aacgactggt | tgaggaagt | gaaagctaag | cgcggcaagc | 900 |
| gcccgacaac | cttccagttc | ctgcaagaaa | tcaagccgga | agccgtagcg | tacatcacca | 960 |
| ttaagaccac | tctggcttgc | ctaaccagtg | ctgacaatac | aaccgttcag | gctgtagcaa | 1020 |
| gcgcaatcgg | tcgggccatt | gaggacgagg | ctcgcttcgg | tcgtatccgt | gaccttgaag | 1080 |
| ctaagcactt | caagaaaaac | gttgaggaac | aactcaacaa | gcgcgtaggg | cacgtctaca | 1140 |
| agaaagcatt | tatgcaagtt | gtcgaggctg | acatgctctc | taagggtcta | ctcggtggcg | 1200 |
| aggcgtggtc | ttcgtggcat | aaggaagact | ctattcatgt | aggagtacgc | tgcatcgaga | 1260 |
| tgctcattga | gtcaaccgga | atggttagct | tacaccgcca | aaatgctggc | gtagtaggtc | 1320 |
| aagactctga | gactatcgaa | ctcgcacctg | aatacgctga | ggctatcgca | acccgtgcag | 1380 |
| gtgcgctggc | tggcatctct | ccgatgttcc | aaccttgcgt | agttcctcct | aagccgtgga | 1440 |
| ctggcattac | tggtggtggc | tattgggcta | acggtcgtcg | tcctctggcg | ctggtgcgta | 1500 |
| ctcacagtaa | gaaagcactg | atgcgctacg | aagacgttta | catgcctgag | gtgtacaaag | 1560 |
| cgattaacat | tgcgcaaaac | accgcatgga | aaatcaacaa | gaaagtccta | gcggtcgcca | 1620 |
| acgtaatcac | caagtggaag | cattgtccgg | tcgaggacat | ccctgcgatt | gagcgtgaag | 1680 |
| aactcccgat | gaaaccggaa | gacatcgaca | tgaatcctga | ggctctcacc | gcgtggaaac | 1740 |
| gtgctgccgc | tgctgtgtac | cgcaaggaca | aggctcgcaa | gtctcgccgt | atcagccttg | 1800 |
| agttcatgct | tgagcaagcc | aataagtttg | ctaaccataa | ggccatctgg | ttcccttaca | 1860 |
| acatggactg | gcgcggtcgt | gtttacgctg | tgtcaatgtt | caacccgcaa | ggtaacgata | 1920 |
| tgaccaaagg | actgcttacg | ctggcgaaag | gtaaaccaat | cggtaaggaa | ggttactact | 1980 |
| ggctgaaaat | ccacggtgca | aactgtgcgg | gtgtcgataa | ggttccgttc | cctgagcgca | 2040 |
| tcaagttcat | tgaggaaaac | cacgagaaca | tcatggcttg | cgctaagtct | ccactggaga | 2100 |
| acacttggtg | ggctgagcaa | gattctccgt | tctgcttcct | tgcgttctgc | tttgagtacg | 2160 |

```
ctggggtaca gcaccacggc ctgagctata actgctccct tccgctggcg tttgacgggt    2220
cttgctctgg catccagcac ttctccgcga tgctccgaga tgaggtaggt ggtcgcgcgg    2280
ttaacttgct tcctagtgaa accgttcagg acatctacgg gattgttgct aagaaagtca    2340
acgagattct acaagcagac gcaatcaatg ggaccgataa cgaagtagtt accgtgaccg    2400
atgagaacac tggtgaaatc tctgagaaag tcaagctggg cactaaggca ctggctggtc    2460
aatggctggc ttacggtgtt actcgcagtg tgactaagcg ttcagtcatg acgctggctt    2520
acgggtccaa agagttcggc ttccgtcaac aagtgctgga agataccatt cagccagcta    2580
ttgattccgg caagggtctg atgttcactc agccgaatca ggctgctgga tacatggcta    2640
agctgatttg ggaatctgtg agcgtgacgg tggtagctgc ggttgaagca atgaactggc    2700
ttaagtctgc tgctaagctg ctggctgctg aggtcaaaga taagaagact ggagagattc    2760
ttcgcaagcg ttgcgctgtg cattgggtaa ctcctgatgg tttccctgtg tggcaggaat    2820
acaagaagcc tattcagacg cgcttgaacc tgatgttcct cggtcagttc cgcttacagc    2880
ctaccattaa caccaacaaa gatagcgaga ttgatgcaca caaacaggag tctggtatcg    2940
ctcctaactt tgtacacagc caagacggta gccaccttcg taagactgta gtgtgggcac    3000
acgagaagta cggaatcgaa tcttttgcac tgattcacga ctccttcggt accattccgg    3060
ctgacgctgc gaacctgttc aaagcagtgc gcgaaactat ggttgacaca tatgagtctt    3120
gtgatgtact ggctgatttc tacgaccagt tcgctgacca gttgcacgag tctcaattgg    3180
acaaaatgcc agcacttccg gctaaaggta acttgaacct ccgtgacatc ttagagtcgg    3240
acttcgcgtt cgcgtaa                                                   3257

<210> SEQ ID NO 85
<211> LENGTH: 3257
<212> TYPE: DNA
<213> ORGANISM: Artificial Sequence
<220> FEATURE:
<223> OTHER INFORMATION: Synthetic sequence

<400> SEQUENCE: 85
tgagcgcaac gcaattaatg taagttagct cactcattag gcaccccagg ctttacactt      60
tatgcttccg gctcgtataa tgtgtggaat tgtgagcgga taacaatttc acacaggaaa     120
cagctatgac catgattacg gattcactgg ccgtcgtttt acaacgtcgt gactgggaaa     180
accctggcgt tacccaactt aatcgccttg cagcacatcc cccttcgcc agctggcgta     240 atagcgaaga ggcccgcacc gatcgccctt cccaacagtt gcgcagcctg aatggcgaat     300
ggcgctttgc ctggtttccg gcaccagaag cggtgccgga agctggctg gagtgcgatc     360 ttcctgaggc cgatactgtc gtcgtcccct caaactggca gatgcacggt tacgatgcgc     420
ccatctacac caacgtgacc tatcccatta cggtcaatcc gccgtttgtt cccacggaga     480
atccgacggg ttgttactcg ctcacattta atgttgatga agctggcta caggaaggcc     540 agacgcgaat tatttttgat ggcgtcggga tctgatccgg atttactaac tggaagaggc     600
actaaatgaa cacgattaac atcgctaaga acgacttctc tgacatcgaa ctggctgcta     660
tcccgttcaa cactctggct gaccattacg gtgagcgttt agctcgcgaa cagttggccc     720
ttgagcatga gtcttacgag atgggtgaag cacgcttccg caagatgttt gagcgtcaac     780
ttaaagctgg tgaggttgcg gataacgctg ccgccaagcc tctcatcact accctactcc     840
ctaagatgat tgcacgcatc aacgactggt ttgaggaagt gaaagctaag cgcggcaagc     900
```

-continued

```
gcccgacagc cttccagttc ctgcaagaaa tcaagccgga agccgtagcg tacatcacca    960
ttaagaccac tctggcttgc ctaaccagtg ctgacaatac aaccgttcag gctgtagcaa   1020
gcgcaatcgg tcgggccatt gaggacgagg ctcgcttcgg tcgtatccgt gaccttgaag   1080
ctaagcactt caagaaaaac gttgaggaac aactcaacaa gcgcgtaggg cacgtctaca   1140
agaaagcatt tatgcaagtt gtcgaggctg acatgctctc taagggtcta ctcggtggcg   1200
aggcgtggtc ttcgtggcat aaggaagact ctattcatgt aggagtacgc tgcatcgaga   1260
tgctcattga gtcaaccgga atggttagct tacaccgcca aaatgctggc gtagtaggtc   1320
aagactctga gactatcgaa ctcgcacctg aatacgctga ggctatcgca acccgtgcag   1380
gtgcgctggc tggcatctct ccgatgttcc aaccttgcgt agttcctcct aagccgtgga   1440
ctggcattac tggtggtggc tattgggcta acggtcgtcg tcctctgcg ctggtgcgta    1500
ctcacagtaa gaaagcactg atgcgctacg aagacgttta catgcctgag gtgtacaaag   1560
cgattaacat tgcgcaaaac accgcatgga aaatcaacaa gaaagtccta gcggtcgcca   1620
acgtaatcac caagtggaag cattgtccgg tcgaggacat ccctgcgatt gagcgtgaag   1680
aactcccgat gaaaccggaa gacatcgaca tgaatcctga ggctctcacc gcgtggaaac   1740
gtgctgccgc tgctgtgtac cgcaaggaca aggctcgcaa gtctcgccgt atcagccttg   1800
agttcatgct tgagcaagcc aataagtttg ctaaccataa ggccatctgg ttcccttaca   1860
acatggactg gcgcggtcgt gtttacgctg tgtcaatgtt caacccgcaa ggtaacgata   1920
tgaccaaagg actgcttacg ctggcgaaag gtaaaccaat cggtaaggaa ggttactact   1980
ggctgaaaat ccacggtgca aactgtgcgg tgtcgataa ggttccgttc cctgagcgca    2040
tcaagttcat tgaggaaaac cacgagaaca tcatggcttg cgctaagtct ccactggaga   2100
acacttggtg ggctgagcaa gattctccgt tctgcttcct tgcgttctgc tttgagtacg   2160
ctggggtaca gcaccacggc ctgagctata actgctccct tccgctggcg tttgacgggt   2220
cttgctctgg catccagcac ttctccgcga tgctccgaga tgaggtaggt ggtcgcgcgg   2280
ttaacttgct tcctagtgaa accgttcagg acatctacgg gattgttgct aagaaagtca   2340
acgagattct acaagcagac gcaatcaatg ggaccgataa cgaagtagtt accgtgaccg   2400
atgagaacac tggtgaaatc tctgagaaag tcaagctggg cactaaggca ctggctggtc   2460
aatggctggc ttacggtgtt actcgcagtg tgactaagcg ttcagtcatg acgctggctt   2520
acgggtccaa agagttcggc ttccgtcaac aagtgctgga agataccatt cagccagcta   2580
ttgattccgg caagggtctg atgttcactc agccgaatca ggctgctgga tacatggcta   2640
agctgatttg ggaatctgtg agcgtgacgg tggtagctgc ggttgaagca atgaactggc   2700
ttaagtctgc tgctaagctg ctggctgctg aggtcaaaga taagaagact ggagagattc   2760
ttcgcaagcg ttgcgctgtg cattgggtaa ctcctgatgg tttccctgtg tggcaggaat   2820
acaagaagcc tattcagacg cgcttgaacc tgatgttcct cggtcagttc cgcttacagc   2880
ctaccattaa caccaacaaa gatagcgaga ttgatgcaca caaacaggag tctggtatcg   2940
ctcctaactt tgtacacagc caagacggta gccaccttcg taagactgta gtgtgggcac   3000
acgagaagta cggaatcgaa tcttttgcac tgattcacga ctccttcggt accattcagg   3060
ctgacgctgc gaacctgttc aaagcagtgc gcgaaactat ggttgacaca tatgagtctt   3120
gtgatgtact ggctgatttc tacgaccagt tcgctgacca gttgcacgag tctcaattgg   3180
acaaaatgcc agcacttccg gctaaaggta acttgaacct ccgtgacatc ttagagtcgg   3240
acttcgcgtt cgcgtaa                                                 3257
```

<210> SEQ ID NO 86
<211> LENGTH: 88
<212> TYPE: DNA
<213> ORGANISM: Artificial Sequence
<220> FEATURE:
<223> OTHER INFORMATION: Synthetic sequence

<400> SEQUENCE: 86
cgtaccgcgg ttgtgtggaa ttgtgagcgg ataacaattt cacacagaaa cagctccctc    60
gtacgaaatt aatacgactc actatagg                                       88

<210> SEQ ID NO 87
<211> LENGTH: 43
<212> TYPE: DNA
<213> ORGANISM: Artificial Sequence
<220> FEATURE:
<223> OTHER INFORMATION: Synthetic sequence

<400> SEQUENCE: 87
ctagaaataa ttttgtttaa ctttaagaag gagatatacc atg                      43

<210> SEQ ID NO 88
<211> LENGTH: 44
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(6)
<223> OTHER INFORMATION: n is a, c, g, or t

<400> SEQUENCE: 88
nnnnnnaata ttttgttta actttaagaa ggagatatac catg                      44

<210> SEQ ID NO 89
<211> LENGTH: 43
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(5)
<223> OTHER INFORMATION: n is a, c, g, or t

<400> SEQUENCE: 89
nnnnnaataa ttttgtttaa ctttaagaag gagatatacc atg                      43

<210> SEQ ID NO 90
<211> LENGTH: 45
<212> TYPE: DNA
<213> ORGANISM: Artificial Sequence
<220> FEATURE:
<223> OTHER INFORMATION: Synthetic sequence

<400> SEQUENCE: 90
tctagaaata attttgttta actttaagaa ggagatatac atatg                    45

<210> SEQ ID NO 91

<211> LENGTH: 44
<212> TYPE: DNA
<213> ORGANISM: Artificial Sequence
<220> FEATURE:
<223> OTHER INFORMATION: Synthetic sequence

<400> SEQUENCE: 91
ctagaaataa ttttgtttaa ctttaagaag gagatataca tatg        44

<210> SEQ ID NO 92
<211> LENGTH: 45
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(6)
<223> OTHER INFORMATION: n is a, c, g, or t

<400> SEQUENCE: 92
nnnnnnaata attttgttta actttaagaa ggagatatac atatg        45

<210> SEQ ID NO 93
<211> LENGTH: 44
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(5)
<223> OTHER INFORMATION: n is a, c, g, or t

<400> SEQUENCE: 93
nnnnnaataa ttttgtttaa ctttaagaag gagatataca tatg        44

<210> SEQ ID NO 94
<211> LENGTH: 41
<212> TYPE: DNA
<213> ORGANISM: Artificial Sequence
<220> FEATURE:
<223> OTHER INFORMATION: Synthetic sequence

<400> SEQUENCE: 94
taatacgact cactataggg gaattgtgag cgctcacaat t        41

<210> SEQ ID NO 95
<211> LENGTH: 40
<212> TYPE: DNA
<213> ORGANISM: Artificial Sequence
<220> FEATURE:
<223> OTHER INFORMATION: Synthetic sequence

<400> SEQUENCE: 95
taatacgact cactataggg aattgtgagc gctcacaatt        40

<210> SEQ ID NO 96
<211> LENGTH: 39
<212> TYPE: DNA
<213> ORGANISM: Artificial Sequence
<220> FEATURE:
<223> OTHER INFORMATION: Synthetic sequence -continued

<400> SEQUENCE: 96
taatacgact cactatagga attgtgagcg ctcacaatt        39

<210> SEQ ID NO 97
<211> LENGTH: 38
<212> TYPE: DNA
<213> ORGANISM: Artificial Sequence
<220> FEATURE:
<223> OTHER INFORMATION: Synthetic sequence

<400> SEQUENCE: 97
taatacgact cactatagaa ttgtgagcgc tcacaatt        38

<210> SEQ ID NO 98
<211> LENGTH: 41
<212> TYPE: DNA
<213> ORGANISM: Artificial Sequence
<220> FEATURE:
<223> OTHER INFORMATION: Synthetic sequence

<400> SEQUENCE: 98
taatacgact cactatagga gaattgtgag cgctcacaat t        41

<210> SEQ ID NO 99
<211> LENGTH: 41
<212> TYPE: DNA
<213> ORGANISM: Artificial Sequence
<220> FEATURE:
<223> OTHER INFORMATION: Synthetic sequence

<400> SEQUENCE: 99
taatacgact cactatagag gaattgtgag cgctcacaat t        41

<210> SEQ ID NO 100
<211> LENGTH: 40
<212> TYPE: DNA
<213> ORGANISM: Artificial Sequence
<220> FEATURE:
<223> OTHER INFORMATION: Synthetic sequence

<400> SEQUENCE: 100
taatacgact cactatagag aattgtgagc gctcacaatt        40

<210> SEQ ID NO 101
<211> LENGTH: 40
<212> TYPE: DNA
<213> ORGANISM: Artificial Sequence
<220> FEATURE:
<223> OTHER INFORMATION: Synthetic sequence

<400> SEQUENCE: 101
taatacgact cactataagg aattgtgagc gctcacaatt        40

<210> SEQ ID NO 102
<211> LENGTH: 41
<212> TYPE: DNA
<213> ORGANISM: Artificial Sequence
<220> FEATURE:
<223> OTHER INFORMATION: Synthetic sequence

<400> SEQUENCE: 102
taatacgact cactataagg gaattgtgag cgctcacaat t        41